(12) United States Patent
Kem et al.

(10) Patent No.: US 7,348,305 B2
(45) Date of Patent: Mar. 25, 2008

(54) INHIBITOR OF CARDIAC TACHYARRHYTHMIAS

(75) Inventors: David C. Kem, Edmond, OK (US); Eugene Patterson, Oklahoma City, OK (US)

(73) Assignee: Department of Veterans Affairs, Rehabilitation, Washington, DC (US)

( * ) Notice: Subject to any disclaimer, the term of this patent is extended or adjusted under 35 U.S.C. 154(b) by 0 days.

(21) Appl. No.: 10/927,616

(22) Filed: Aug. 26, 2004

(65) Prior Publication Data

US 2005/0079178 A1   Apr. 14, 2005

Related U.S. Application Data

(60) Provisional application No. 60/498,434, filed on Aug. 28, 2003.

(51) Int. Cl.
*A61K 38/00* (2006.01)
(52) U.S. Cl. .......................................... 514/2
(58) Field of Classification Search ...................... None
See application file for complete search history.

(56) References Cited

U.S. PATENT DOCUMENTS

| | | | |
|---|---|---|---|
| 6,015,557 A | | 1/2000 | Tobinick |
| 6,096,711 A | * | 8/2000 | Sherman et al. ............... 514/18 |
| 6,177,077 B1 | | 1/2001 | Tobinick |
| 6,271,199 B2 | | 8/2001 | Brand et al. |
| 6,379,666 B1 | | 4/2002 | Tobinick |
| 6,419,934 B1 | | 7/2002 | Tobinick |
| 6,423,321 B2 | | 7/2002 | Tobinick |
| 6,428,787 B1 | | 8/2002 | Tobinick |
| 6,531,128 B1 | | 3/2003 | Wax et al. |
| 6,537,549 B2 | | 3/2003 | Tobinick |
| 6,548,527 B2 | | 4/2003 | Rahman et al. |

OTHER PUBLICATIONS

Jaber M et al "Essential Role of Beta-Adrenergic Receptor Kinase I in Cardiac Development and Function", Nov. 1, 1996, Proc. Natl. Acad. Sci. vol. 93, pp. 12974-12979.*
Brendel J et al "Blockers of the Kv1.5 Channel For The Treatment of Atrial Arrhythmias", Nov. 2002, Expert Opin. Ther. Patents vol. 12. pp. 1589-1598.*
Cross et al., "Overexpression of the cardiac beta2-adrenergic receptor and expression of a beta-adrenergic receptor kinase (BARK1) inhibitor both increase myocardial contractility but have differential effects on suspectibility to ischemic injury". Circulation Research, 85:1077-1085 (1999), especially abstract and especially pp. 1079 and 1081.
Ungerer, M. et al., Activation of B-Adrenergic Receptor Kinase During Myocardial Ischemia. Circulation Research 79:455-460 (1996), see entire document.
White et al., "Preservation of myocardial beta-adrenergic receptor signaling delays the development of heart failure after myocardial infarction". Proc. Natl. Acad. Sci. USA 97:5428-5433 (2000), especially p. 5429, Figure 1.

\* cited by examiner

*Primary Examiner*—Cecilia J. Tsang
*Assistant Examiner*—Maury Audet
(74) *Attorney, Agent, or Firm*—Dunlap, Codding & Rogers, P.C.

(57) ABSTRACT

Methods of preventing sustained monomorphic ventricular tachycardia following myocardial ischemia, decreasing infarct size and/or decreasing the incidence and/or maximum intrinsic rate of very rapid ventricular triplets following myocardial ischemia is disclosed. The methods involve administering an effective amount of a composition that inhibits substantial loss of beta-adrenergic receptor kinase (β-ARK) activity and/or β-ARK expression.

7 Claims, 29 Drawing Sheets

RECURRENT SUSTAINED MONOMORPHIC VT

4 HRS 16 MINUTES

12 HRS 46 MINUTES            ⊢ 5 SEC ⊣

13 HRS 25 MINUTES

15 HRS 34 MINUTES

⊢ 1 SEC ⊣

Stimulation of Ikk, Phosphorylation of IkB

Non-Stimulated State

Proteasome degradation of IkB, NFkB initiated transcription

Ubiquination of phosphorylated IkB, Translocation of NFkB

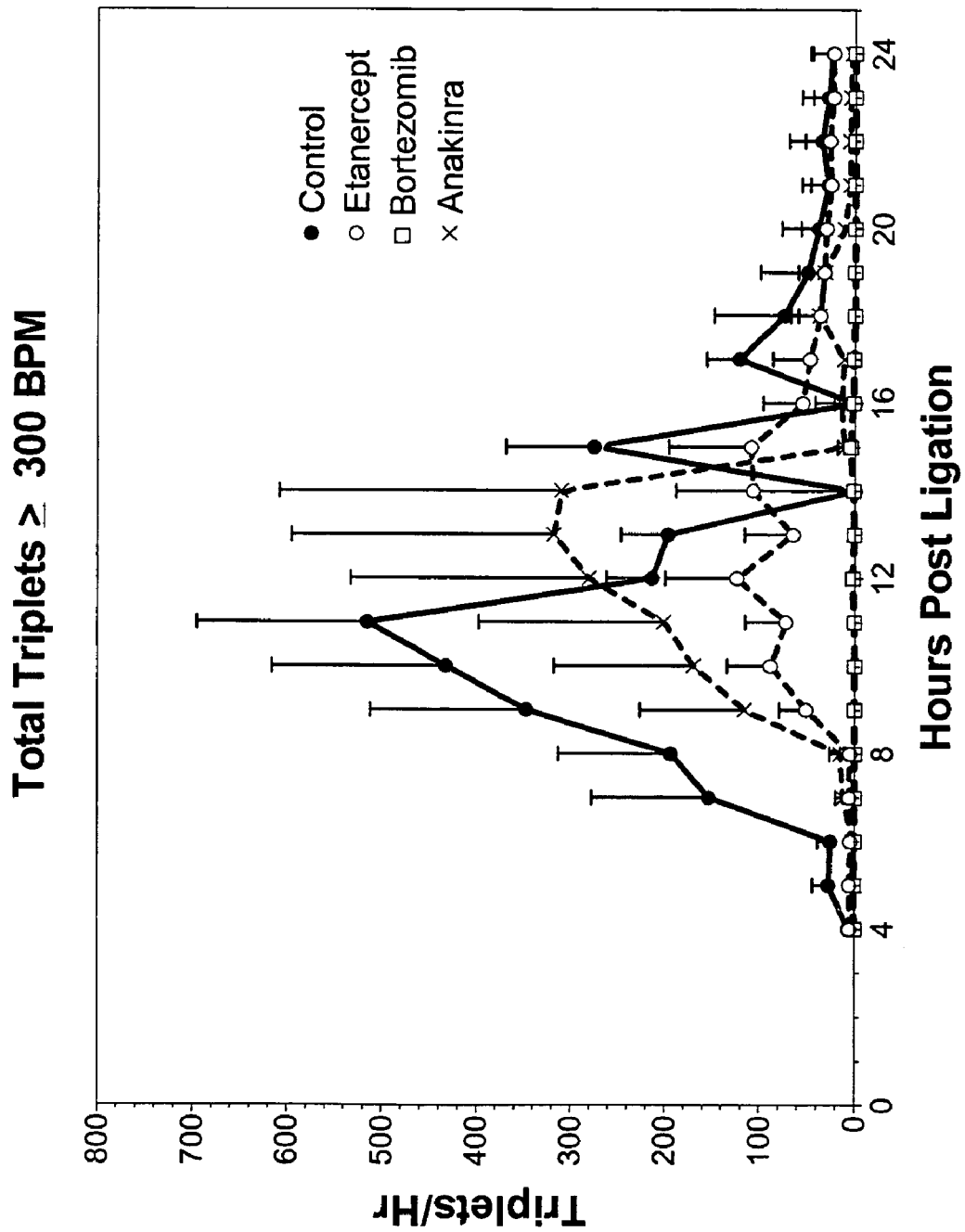

INHIBITOR OF CARDIAC TACHYARRHYTHMIAS

CROSS-REFERENCE TO RELATED APPLICATIONS

This application claims benefit under 35 U.S.C. 119(e) of U.S. provisional patent application Ser. No. 60/498,434, filed Aug. 28, 2003, entitled "INHIBITOR OF CARDIAC TACHYARRHYTHMIAS", which is hereby expressly incorporated herein by reference in its entirety.

STATEMENT REGARDING FEDERALLY SPONSORED RESEARCH OR DEVELOPMENT

At least a portion of the invention was developed under funding from the VA Veterans Foundation under contract No. 8563. As such, the Government may own certain rights in and to this application.

BACKGROUND OF THE INVENTION

1. Field of the Invention

The invention relates to the prevention and/or termination of malignant sustained ventricular tachyarrhythmia. Ventricular tachyarrhythmia can be followed by ventricular fibrillation, which can lead to sudden death, and occurs primarily in patients having cardiomyopathies, such as myocardial ischemia, myocardial infarction, or other conditions which cause ischemia of cardiac tissue. The high incidence of recurrent ventricular fibrillation and sudden death in survivors of cardiac arrest underscores the need for an effective approach to prophylactic treatment in these patients.

2. Brief Description of the Art

Ventricular tachyarrhythmias arising from myocardial ischemia and infarction are a leading cause of sudden cardiac death (SCD) in the United States. Malignant ventricular tachyarrhythmias occur in patients with coronary artery disease commonly in association with acute coronary artery occlusion and a previously healed myocardial infarction (Gillum, 1989; Liberthson et al., 1974). Identifiable risk factors include but are not limited to: a) an underlying substrate capable of sustaining a reentrant ventricular arrhythmia (Kleiman et al., 1988; Iesaka, 1990); b) an increased sympathetic nervous system tone (Kleiger et al., 1987); and c) reduced ventricular function and frequent ventricular ectopy (Bigger et al., 1984; Moss et al., 1979).

The importance of increased sympathetic tone (increased sympathetic nervous system activity, increased circulating catecholamines, and/or increased β-adrenergic receptor sensitivity) as a risk factor for sudden death is underscored by the efficacy of β-adrenergic receptor antagonists in reducing mortality during acute myocardial ischemia (Hjalmarsson et al., 1981) and during the recovery phase of myocardial infarction (β-Blocker Heart Attack Trial Research Group, 1982; Olsson et al., 1985). Although β-adrenergic receptor blockade is the accepted pharmacologic basis for their protective actions, the electrophysiologic bases for their protective actions are less well-defined.

Both increased sympathetic nervous system tone (Malliani et al., 1980) and increased βAR sensitivity (Cameron et al., 1982) have been documented during the first 24 hours in canine models of myocardial infarction. An altered responsiveness of the myocardium to adrenergic stimuli under conditions of ischemia is an important mediator of triggered beats and/or delayed reentry resulting in ventricular tachyarrhythmias and sudden cardiac death. Epicardial border zone (EBZ) tissue is recognized as the substrate for development of recurrent ventricular arrhythmias, including ventricular tachycardia and subsequent propagation to ventricular fibrillation and SCD (Steinberg et al., 1995; Yamada et al., 1992; Dangman et al., 1988). Triggered beats in the EBZ overlying the infarct after 24 hours have been studied in detail (Dangman et al., 1988). It has been demonstrated that abnormal electro-physiological activity is obtained upon exposure to a β-agonist indicating enhanced tissue sensitivity to β-agonists during the first 24 hours after ischemia.

Increased sympathetic nervous system activity augments ventricular arrhythmia development during the first 30 minutes following coronary artery occlusion. The facilitatory role of the sympathetic nervous system can be established by the increased incidence of ventricular arrhythmia and increased incidence of ventricular fibrillation observed during cardiac sympathetic nerve stimulation (Schwartz et al., 1981; Euler et al., 1985), and a decreased incidence and severity of ventricular arrhythmias observed following β-adrenergic receptor blockade (9,10) or transection of sympathetic nerves innervating the heart (Harris et al., 1951; Milch et al., 1955). An even more critical role for the sympathetic nervous system is suggested for experimental arrhythmia models wherein acute ischemia is interposed upon previous myocardial infarction. The presence of high sympathetic nervous system tone is crucial for the initiation of lethal ventricular arrhythmia in the dog when an acute ischemic episode is superimposed upon previous myocardial infarction (Schwartz et al., 1980; Patterson et al., 1982), and lethal arrhythmias were markedly suppressed with the administration of β-adrenergic receptor antagonists (Patterson et al., 1983; DeFerrari et al., 1993).

Although there is a clear association between increased sympathetic nervous system tone and an increased incidence of lethal ventricular arrhythmia during an acute episode of myocardial ischemia in animal models, the importance and mechanism(s) of increased sympathetic tone as a risk factor for lethal arrhythmia observed during subacute recovery phase from myocardial infarction is less well established.

Electrocardiographic recordings obtained from ambulatory patients at the time of sudden death demonstrate an increase in rapid ventricular ectopy preceding either sustained monomorphic, or less commonly, polymorphic tachycardia consistent with triggering of an underlying reentrant substrate by ventricular premature beats (Kempf et al., 1984; Panidis et al., 1983). In the experimental model of the present invention described herein below, a canine model of sudden arrhythmic death is utilized, occurring during a 2 to 24 hr period following two stage left anterior descending (LAD) coronary artery occlusion, which incorporates several of those features observed in man (Patterson et al., 1986; Patterson et al., 1991; Patterson et al., 1991).

Tissue TNFα increases in myocardial infarction (Gurevitch et al., 1996; Frangogiannis et al., 1998; Irwin et al., 1999; Torre-Amione et al., 1996). This serves as one of several cytokine-mediated attractants for neutrophil migration into the ischemic region and enhances the inflammatory reaction that is related to progressive tissue destruction (Entman et al., 1994; Youker et al., 1994). These mediators of inflammation result in loss of cellular function, widespread destruction, proteolysis and apoptosis in the infarct region. These events are also observed to a lesser and variable extent in adjacent regions such as the EBZ.

β-Adrenergic receptor kinase 1 (βARK), a member of the G-protein receptor kinase (GRK) superfamily, diminishes β-AR sensitivity by phosphorylation of the target receptors (Krupnick et al., 1998; Pitcher et al., 1998; Bunemann et al., 1999). Changes of the endogenous β-AR modulator also have been shown to modulate tissue-specific β-AR changes in sensitivity to agonist stimulation (Koch et al., 1995; Ungerer et al., 1996; Ping et al., 1997). A rapid decrease in βARK expression and activity in EBZ tissue following LAD ligation has been previously reported by the inventors (Yu et al., 2000). This was associated with a decreased ability of the affected cardiac tissue to desensitize to β-AR agonist-induced signal transduction during a period extending at least from 6 to 24 hours after coronary artery ligation in the dog. This EBZ tissue therefore becomes more vulnerable to β-AR-induced arrhythmias.

Therefore, there exists a need in the art for new and improved compositions for treating and/or preventing ventricular tachyarrhythmias, including sustained monomorphic ventricular tachyarrhythmias, in response to mycordial ischemia and/or infarction, as well as methods of using same, that overcome the disadvantages and defects of the prior art. It is to such compositions and methods of treatment, wherein the composition inhibits substantial loss of β-ARK activity and/or expression, that the present invention is directed.

BRIEF DESCRIPTION OF THE SEVERAL VIEWS OF THE DRAWINGS

In FIG. 11, tissue immunoblots of $G_{i\alpha}$ (A) and $G_{S\alpha}$ (B) in cardiac membranes from normal and 24-hour CAL tissue are illustrated. Lane 1, normal RS; lane 2, EBZ; lane 3, RS; lane 4, EBZ; lane 5, infarct. Relative density of $G_{i\alpha}$ and $G_{S\alpha}$ in EBZ (n=4) is expressed as a percentage of RS (100%), and mean values are shown in bar graphs. There was no significant difference in $G_{i\alpha}$ and $G_{S\alpha}$ levels in this study (NS).

FIG. 17 illustrates rapid ventricular triplets in control and etanercept treatment groups.

FIG. 31 illustrates rapid ventricular triplets in control and treatment groups, wherein the treatment groups were treated with etanercept, bortezomib, or anakinra. FIG. 31A shows the incidence (mean±SEM) of rapid ventricular triplets (all ≧300 bpm) per hour for control (●, n=10), etanercept-treated (○, n=8), bortezomib (□, n=6) and anakinra (x, n=6). The deaths of four dogs in the control group all occurred prior to 16 hours.

DETAILED DESCRIPTION OF THE INVENTION

Figure 1:
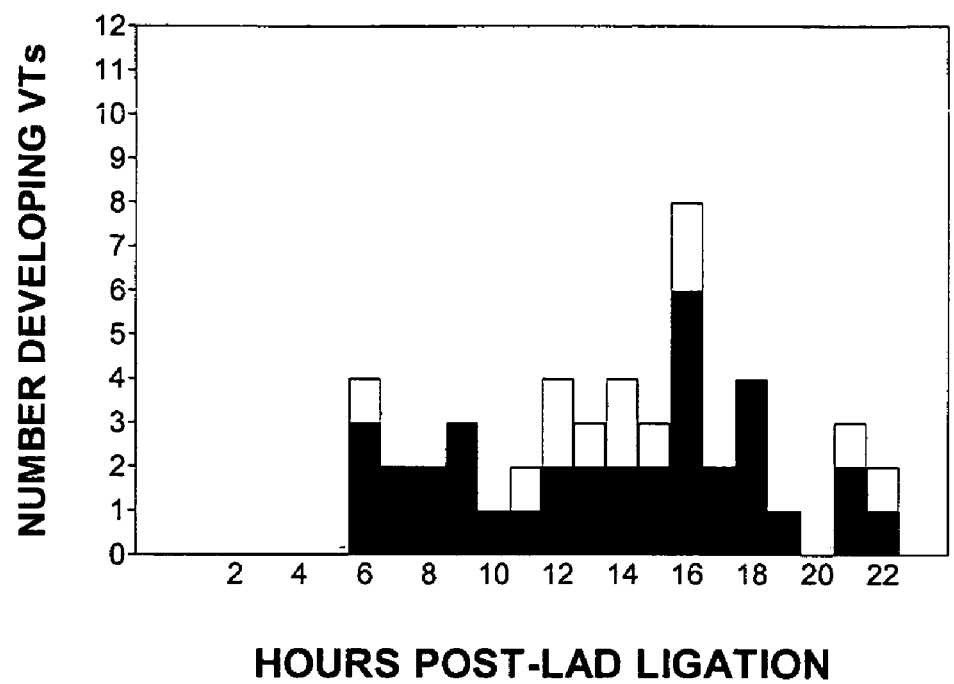
FIG. 1 illustrates sustained ventricular tachycardia following two-stage coronary artery occlusion in the dog. The closed bars represent those animals which developed sustained ventricular tachycardia leading to fatal ventricular fibrillation. The open bars represent animals developing similar rapid tachycardias which were self-terminating, and the animals survived.

Before explaining at least one embodiment of the invention in detail by way of exemplary drawings, experimentation, results, and laboratory procedures, it is to be understood that the invention is not limited in its application to the details of construction and the arrangement of the components set forth in the following description or illustrated in the drawings, experimentation and/or results. The invention is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Coronary artery circulation normally supplies sufficient blood flow to the heart to meet the demands of the heart muscle (myocardium) as it labors under a widely varying workload. An imbalance that arises between this supply and demand usually precipitates angina pectoris (pain). When the imbalance becomes excessive, myocardial infarction results. Myocardial infarction is necrosis or death of cardiac tissue resulting from the lack of blood flow to the heart. For example, the narrowing of a major coronary artery by more than fifty percent (50%) impairs nutrient blood flow under conditions of increased myocardial demand.

By far the most common underlying pathologic process that gives rise to the narrowing of a major coronary artery is atherosclerosis. In most patients suffering from atherosclerosis, plaque develops in the proximal segments of the coronary arteries. In other patients, this condition may be diffuse and may occur in both proximal and distal vessels.

Increases in oxygen consumption (also referred to herein as oxygen requirement) cause ischemia if coronary artery blood flow cannot rise to meet a higher demand. The clinical manifestations of ischemia are angina, myocardial infarction, congestive heart failure, and electrical instability (arrhythmia). The last menentioned symptom is assumed to account for most of the sudden cardiac death syndrome patients.

In treating ischemia, the primary goal of medical therapy is to reduce oxygen consumption and increase blood supply by reducing vascular tone (improving collateral flow) preventing thrombosis and opening or bypassing the blockage in the artery or arteries affected If a clot is causing the blockage, a thrombolytic drug may be used to open the occluded artery. The most direct way to increase blood supply is to revascularize by coronary artery bypass surgery or angioplasty.

Cardiac electrical instability (arrhythmia) may occur during ischemic events and is also a common condition after a myocardial infarction. Since cardiac arrhythmias such as ventricular tachycardia can degenerate into ventricular fibrillation which generally is life terminating, these arrhythmias are of great concern to the physician or cardiologist. To control such arrhythmias, the cardiologist may choose to treat the patient with antiarrhythmic drugs.

The present invention is related to the prevention and/or termination of malignant ventricular tachyarrhythmia, particularly sustained monomorphic ventricular tachycardia. The methods of the present invention comprise administering to a patient a pharmaceutically effective amount of a composition that inhibits substantial loss of at least one of beta-adrenergic receptor kinase (β-ARK) activity and β-ARK expression.

As used herein, the term "substantial loss of at least one of β-ARK activity and β-ARK expression" refers to loss of at least about 95% of β-ARK activity and/or β-ARK expression under non-ischemic conditions. Preferably, the methods of the present invention result in a retention of at least about 10% of β-ARK activity and/or expression under non-ischemic conditions. In another preferred embodiment, the methods of the present invention result in a retention of at least about 15% of β-ARK activity and/or expression under non-ischemic conditions. In yet another preferred embodiment, the methods of the present invention result in a retention of at least about 20% of β-ARK activity and/or expression under non-ischemic conditions. In yet another preferred embodiment, the methods of the present invention result in a retention of at least about 25% of β-ARK activity and/or expression under non-ischemic conditions. In a further preferred embodiment, the methods of the present invention result in a retention of at least about 30% of β-ARK activity and/or expression under non-ischemic conditions. In yet another preferred embodiment, the methods of the present invention result in a retention of at least about 35% of β-ARK activity and/or expression under non-ischemic conditions. In yet a further preferred embodiment, the methods of the present invention result in a retention of at least about 40% of β-ARK activity and/or expression under non-ischemic conditions. In yet another preferred embodiment, the methods of the present invention result in a retention of at least about 45% of β-ARK activity and/or expression under non-ischemic conditions. In another preferred embodiment, the methods of the present invention result in a retention of at least about 50% of β-ARK activity and/or expression under non-ischemic conditions.

The composition that inhibits substantial loss of at least one of β-ARK activity and β-ARK expression is preferably selected from the group consisting of a cytokine inhibitor, a proteasome inhibitor, and combinations thereof. When the composition comprises two or more inhibitors, the inhibitors may be administered sequentially or simultaneously. Preferred examples of cytokine inhibitors to be used in accordance with the present invention include but are not limited to, an inhibitor of tumor necrosis factor, such as but not limited to, etanercept; and an interleukin-1 inhibitor, such as but not limited to, anakinra. A preferred example of a proteasome inhibitor that can be used in accordance with the present invention includes but is not limited to, bortezomib. While preferred examples of cytokine inhibitors and proteasome inhibitors have been described herein, it is to be understood that other cytokine inhibitors and proteasome inhibitors are known to one of ordinary skill in the art, and thus such cytokine inhibitors and proteasome inhibitors also fall within the scope of the present invention.

The terms "therapeutically effective amount" and "pharmaceutically effective amount" are used interchangeably herein and refer to a substantially nontoxic but sufficient amount of an active agent to provide the desired therapeutic effect. The compositions utilized in the methods of the present invention are administered in an amount that is sufficient to prevent, cure and/or treat a condition for a desired period of time for which the composition of this invention is to be administered, and such an amount is referred herein as "a pharmaceutically effective amount." As is well known, particularly in the medicinal arts, effective amounts of medicinal agents vary with the particular agent involved, the condition being treated and the rate at which the composition containing the medicinal agent is eliminated from the body, as well as varying with the animal in which it is being used, and the body weight of that animal. Consequently, effective amounts of treating agents may not be defined for each agent. Thus, an effective amount is that amount which in a composition of the present invention provides a sufficient amount of the treating agent to provide the requisite activity of treating agent in the treated animal for the desired period of time, and is typically less than that amount usually used.

In one embodiment of the present invention, the composition is etanercept (ENBREL™), and the pharmaceutically effective amount of etanercept may vary and thus may be any dosage of etanercept that allows the composition to function in accordance with the methods of the present invention. In a preferred embodiment, the pharmaceutically effective amount of etanercept is in a range of from about 0.5 mg/kg to about 10 mg/kg, and preferably in a range of from about 1 mg/kg to about 6 mg/kg, and more preferably in a range of from about 2 mg/kg to about 4 mg/kg.

In another embodiment of the present invention, the composition is anakinra (KINERET™), and the pharmaceutically effective amount of anakinra may vary and thus may be any dosage of anakinra that allows the composition to function in accordance with the methods of the present invention. In a preferred embodiment, the pharmaceutically effective amount of anakinra is in a range of from about 1 mg/kg to about 30 mg/kg, and preferably in a range of from about 5 mg/kg to about 20 mg/kg, and more preferably in a range of from about 10 mg/kg to about 15 mg/kg.

In yet another embodiment of the present invention, the composition is bortezomib (VELCADE™), and the pharmaceutically effective amount of bortezomib may vary and thus may be any dosage of bortezomib that allows the composition to function in accordance with the methods of the present invention. In a preferred embodiment, the pharmaceutically effective amount of bortezomib is in a range of from about 0.01 mg/kg to about 0.2 mg/kg, and preferably in a range of from about 0.05 mg/kg to about 0.2 mg/kg, and more preferably in a range of from about 0.085 mg/kg to about 0.175 mg/kg. In another preferred embodiment, the pharmaceutically effective amount of bortezomib is in a range of from about 0.7 mg/m$^2$ to about 1.3 mg/m$^2$.

The methods of the present invention may further include administering to a patient a pharmaceutically effective amount of a composition that inhibits substantial loss of at least one of beta-adrenergic receptor kinase (β-ARK) activity and β-ARK expression such that a decrease in infarct size is seen following myocardial ischemia.

In addition, the methods of the present invention may result in a decrease in at least one of the incidence and maximum intrinsic rate of very rapid ventricular triplets or episodes of non-sustained ventricular tachycardia.

The methods of the present invention may further result in the prevention of the degradation of β-ARK in response to myocardial ischemia.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989) and Coligan et al. Current Protocols in Immunology (Current Protocols, Wiley Interscience (1994)), which are expressly incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The terms "ventricular tachyarrhythmia" or "malignant ventricular tachyarrhythmia" as used herein refer to an abnormally rapid ventricular rhythm with aberrant ventricular excitation, usually in excess of 150 per minute in a human, which is generated within the ventricle and is most commonly associated with atrioventricular dissociation. Minor irregularities of heart rate may also occur. The rapid beating associated with ventricular tachyarrhythmia renders the heart ineffectual as a pump.

The term "ventricular fibrillation" as used herein refers to a type of ventricular tachyarrhythmia characterized by rapid, tremulous and ineffectual contractions of the ventricles. Ventricular fibrillation may result from mechanical injury to the heart, occlusion of coronary vessels, effects of certain drugs (such as excess of digitalis, cocaine or chloroform), anaphylactic reactions, electrical stimuli, or ionic imbalance (e.g. calcium, potassium, or sodium).

Ventricular fibrillation may be described as two types. Primary ventricular fibrillation occurs suddenly and unexpectedly in patients with otherwise stable cardiac function. This type of fibrillation is common in the early phase of acute myocardial infarction. Resuscitation of such individuals is highly successful if treated promptly. Secondary ventricular fibrillation occurs as the terminal event in a severely failing heart. At present, resuscitation of patients with secondary ventricular fibrillation is seldom successful.

The terms "imminent ventricular tachyarrhythmia" or "imminent ventricular fibrillation" as used herein refer to an emergency situation in which the patient may proceed from a medical condition involving the heart (e.g., intermittent tachyarrhythmia or heart attack symptoms) to subsequent ventricular fibrillation and cardiac arrest at any moment. Situations involving "imminent" ventricular fibrillation are generally those associated with an emergency room situation (i.e. the patient is at extremely high risk of onset of ventricular fibrillation within minutes to hours). Patients susceptible to "imminent" tachyarrhythmia include those individuals who have developed myocardial ischemia, but may not present with clinical symptoms associated with susceptibility to a heart attack.

The term "termination" of ventricular tachyarrhythmia or ventricular fibrillation refers to cessation of arrhythmia associated with ventricular tachyarrhythmia or ventricular fibrillation, and restoration of normal or near normal heart function, such that the patient is no longer at high to extremely high risk of cardiac arrest.

The term "ischemia" as used herein refers to local and temporary reduction of blood flow due to obstruction of the circulation. The term "myocardial ischemic event" refers to an event associated with local and temporary reduction of blood flow due to obstruction of the circulation to the heart. Examples include but are not limited to events associated with induction of myocardial ischemia, anaphylactic shock, myocardial infarction, and myocardial disease. Myocardial ischemia usually occurs from the narrowing of the coronary arteries as a result of atherosclerosis. Clinically, myocardial ischemia involves decreased oxygen and nutrient delivery to the myocardium resulting from diminished coronary artery blood flow, which in turn leads primarily to abnormalities of left ventricular function and cardiac rhythm and the consequences thereof. Myocardial ischemia occurs when the demands of the heart for oxygen and nutrients are not met commensurately by available blood supply. The physiological effects of myocardial ischemia range from minimal to a complete failure of cardiac pumping function depending upon the degree of myocardial involvement and/or associated cardiac rhythm abnormalities. Clinical manifestations of myocardial ischemia include but are not limited to chest pain or discomfort (angina); respiratory distress, including shortness of breath; fatigue; reduced exercise capacity or tolerance; and nausea.

The term "ischemia-induced ventricular tachyarrhythmia" or "ischemia-induced ventricular fibrillation" refers to ventricular tachyarrhythmia or ventricular fibrillation which results from local and temporary obstruction of circulation to the heart.

The term "myocardial infarction" refers to an area of dying or dead heart tissue resulting from obstruction of blood flow to the heart muscle or some portion of the heart muscle that results from a relative or absolute insufficiency of blood supply.

The terms "patient susceptible to ventricular tachyarrhythmia" and "patient susceptible to ventricular fibrillation" refer to an individual who presents with the conditions described above which may lead to myocardial ischemia.

The term "ventricular triplet" as used herein refers to the occurrence of three consecutive ventricular beats with a heart rate of more than 95 beats per minute in a human. As described in more detail herein, malignant ventricular triplets frequently lead into ventricular fibrillation and sudden cardiac death (SCD) in the LAD dog model. Frequent premature ventricular contractions and periods of nonsustained ventricular tachycardia are characteristically observed in humans in a similar manner and thus may be comparable to the malignant ventricular triplets observed in the dog model.

The terms "active agent," "drug" and "pharmacologically active agent" are used interchangeably herein to refer to a compound or composition of matter which, when administered to an organism (human or other mammal), induces a desired pharmacologic and/or physiologic effect by local or systemic action.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method of "treating" a patient or individual, as the term is used herein, thus encompasses both prevention of a disorder in a predisposed individual and treatment of the disorder in a clinically symptomatic individual.

The term "injection" as used herein refers to administration of a solution, normally with a syringe and needle, directly into a selected site where the total volume of the solution is administered over a relatively short period of time (e.g. less than 5 to 10 minutes).

The term "intracardial injection" as used herein refers to injection of a solution directly into the heart or an artery of the heart.

The term "intravenous infusion" as used herein refers to gradual introduction of a solution directly into a vein, usually the cephalic or median basilic vein of the arm over an extended period of time (e.g. 30 minutes to several hours or days).

By "administered in combination" or "combination therapy" it is meant that a compound of the present invention and one or more additional therapeutic agents are administered concurrently to the mammal being treated. When administered in combination each component may be administered at the same time (simultaneously) or sequentially in any order at different points in time. Thus, each component may be administered separately but sufficiently closely in time so as to provide the desired therapeutic effect.

The terms "cytokine inhibitor", "cytokine antagonist" and "cytokine blocker" are used interchangeably herein to refer to compositions having anti-inflammatory activity related to inhibition of activity and/or expression of one or more cytokines. Cytokine antagonists can take several forms. They may be monoclonal antibodies as described herein below, or they may be in the form of a soluble receptor to that cytokine. Soluble receptors freely circulate in the body. When they encounter their target cytokine they bind to it, effectively inactivating the cytokine, since the cytokine is then no longer able to bind with its biologic target in the body. An even more potent antagonist consists of two soluble receptors fused together to a specific portion of an immunoglobulin molecule (Fc fragment). This produces a dimer composed of two soluble receptors which have a high affinity for the target, and a prolonged half-life.

Monoclonal antibodies with a high affinity for a specific cytokine tend to reduce the biological activity of that cytokine. Substances which reduce the biological effect of a cytokine can be described in any of the following ways: as a cytokine blocker; as a cytokine inhibitor; or as a cytokine antagonist. The terms blocker, inhibitor, and antagonist are used herein interchangeably with respect to interleukin-1 and tumor necrosis factor (TNF).

Cytokines play a central role in the inflammatory response and in immune injury. TNF is formed by the cleavage of a precursor transmembrane protein, forming soluble molecules, which aggregate to form trimolecular complexes. These complexes then bind to receptors found on a variety of cells. Binding produces an array of proinflammatory effects, including release of other pro-inflammatory cytokines, including interleukins IL-6, IL-8, and IL-1; release of matrix metalloproteinases; and up-regulation of the expression of endothelial adhesion molecules, further amplifying the inflammatory and immune cascade by attracting leukocytes into extravascular tissues. TNF is now well established as key in the pathogenesis of rheumatoid arthritis(RA) and Crohn's Disease, and new evidence of its involvement in other non-neurologic disorders and in other non-neurologic organ systems, such as the heart, is rapidly accumulating.

The terms "TNF antagonists", "TNF inhibitors" and "TNF blockers" may be used interchangeably herein and refer to compositions used for the immediate, short term and long term (acute and chronic) blockade of TNF. These compositions have been used as drugs in the treatment of neurological disorders, trauma, injuries or compression; demyelinating neurological disorders, including multiple sclerosis; neurodegenerative diseases, including Alzheimer's disease; muscular disorders; disorders of the optic nerve and retina; and immune-mediated ear disorders. Currently available TNF antagonists which are suitable for use in the present invention include but are not limited to, etanercept (ENBREL™, from Amgen Corporation), a recombinant fusion protein consisting of two soluble TNF receptors joined by the Fc fragment of a human IgG1 molecule, and infliximab (REMICADE™, from Centocor, Inc.), a chimeric anti-TNF monoclonal antibody (mAb). Other specific anti-TNF agents which are under development and which are further contemplated for use in the methods of the present invention include but are not limited to, D2E7 (a human anti-TNF mAb), CDP 571 (a chimeric, but 95% humanized, anti-TNF mAb), and a pegylated soluble TNF type 1 receptor. Additionally, thalidomide has been demonstrated to be a potent anti-TNF agent. Further, anti-TNF therapies may include gene therapy and the development of selective inhibitors of the TNF-alpha converting enzyme. Examples of the uses of TNF inhibitors to ameliorate the conditions described herein above can be found in U.S. Pat. No. 6,015,557, issued to Tobinick et al. on Jan. 18, 2000; U.S. Pat. No. 6,177,077, issued to Tobinick on Jan. 23, 2001; U.S. Pat. No. 6,379,666, issued to Tobinick on Apr. 30, 2002; U.S. Pat. No. 6,419,934, issued to Tobinick on Jul. 16, 2002; US 6,419,944, issued to Tobinick on Apr. 30, 2002; U.S. Pat. No. 6,423,321, issued to Tobinick on Jul. 23, 2002; U.S. Pat. No. 6,428,787, issued to Tobinick on Aug. 6, 2002; U.S. Pat. No. 6,531,128, issued to Wax et al. on Mar. 11, 2003; U.S. Pat. No. 6,537,549, issued to Tobinick on Feb. 25, 2003; and U.S. Pat. No. 6,548,527, issued to Rahman et al. on Apr. 15, 2003; the contents of each of which are hereby expressly incorporated herein by reference.

The terms "interleukin-1 antagonist", "Interleukin-1 inhibitor" and "interleukin-1 blocker" may be used interchangeably herein and refer to compositions used for the immediate, short term and long term (acute and chronic) blockade of interleukin-1. One example of an interleukin-1 antagonist that may be used in accordance with the present invention is anakinra (KINERET™). However, other interleukin-1 antagonists are known to one skilled in the art, and such IL-1 antagonists are also within the scope of the present invention.

The term "proteasome inhibitor" as used herein refers to which directly or indirectly inhibit proteasome activity and/or expression. U.S. Pat. No. 6,271,199, issued to Brand et al. on Aug. 7, 2001, the contents of which are hereby expressly incorporated herein by reference, discloses examples of proteasome inhibitors that maybe utilized in accordance with the present invention. The '199 patent discloses that proteasome inhibitors may be used to reduce the size or lessen the severity of an infarction. However, the ability of proteasome inhibitors to reduce ventricular tachycardia has not been observed prior to the present invention. In addition, one particular example of a proteasome inhibitor that may be utilized in accordance with the present invention is bortezomib (VELCADE™). However, as demonstrated by the '199 patent, other proteasome inhibitors are known to those of ordinary skill in the art, and thus the use of proteasome inhibitors other than bortezomib also falls within the scope of the present invention.

Antibody" or "antibody peptide(s)" refer to an intact antibody, or a binding fragment thereof that competes with the intact antibody for specific binding to an epitope. Binding fragments are produced by recombinant DNA techniques or by enzymatic or chemical cleavage of intact antibodies. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics.

The term "antibody" is used in the broadest sense, and specifically covers monoclonal antibodies (including full length monoclonal antibodies), polyclonal antibodies, multispecific antibodies (e.g., bispecific antibodies), and antibody fragments (e.g., Fab, F(ab').sub.2 and Fv) so long as they exhibit the desired biological activity. Antibodies (Abs) and immunoglobulins (Igs) are glycoproteins having the same structural characteristics.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" as used herein includes human and mammalian veterinary subjects. "Mammal" for purposes of treatment refers to any animal classified as a mammal, including human, domestic and farm animals, nonhuman primates, and zoo, sports, or pet animals, such as dogs, horses, cats, cows, and the like.

Demonstration of the Canine LAD Model of Sudden Cardiac Death (FIGS. 1-15)

Figure 2:
FIG. 2 illustrates recurrent ventricular tachycardia. Electrocardiograms recorded by Holter monitoring are shown for 4 hours 16 minutes, 12 hours 46 minutes, 13 hours 25 minutes and 15 hours 34 minutes after left anterior descending (LAD) coronary artery occlusion. At 4 hours 16 minutes normal sinus rhythm is present. At 12 hours 16 minutes numerous rapid ventricular triplets are present (circles). A 14 second episode of nonsustained ventricular tachycardia (320 beats/min) is present. A 27 second episode of nonsustained ventricular tachycardia was recorded 13 hours 26 minutes after coronary artery occlusion. At 15 hours 34 minutes, incessant ventricular tachycardia was present. The circle denotes a spontaneous ventricular triplet that initiated rapid monomorphic ventricular tachycardia.
Figure 2:
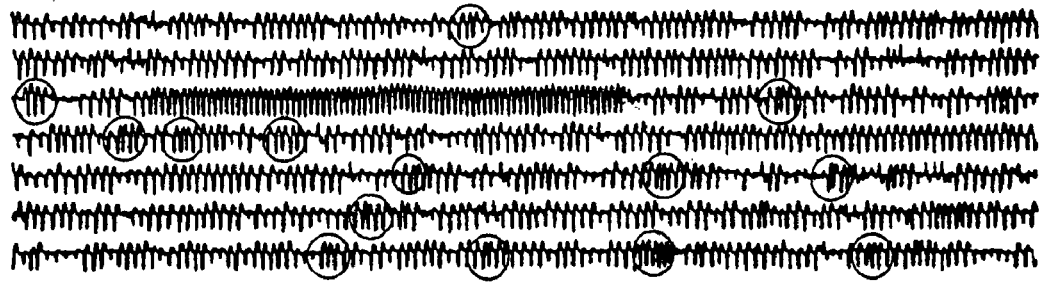
Figure 2:
Figure 2:
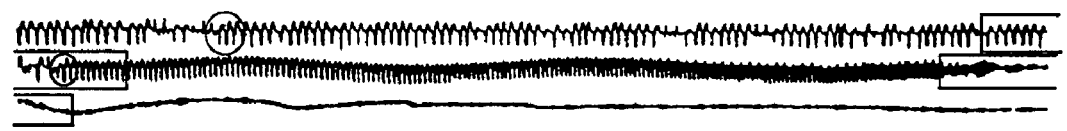
Figure 2:
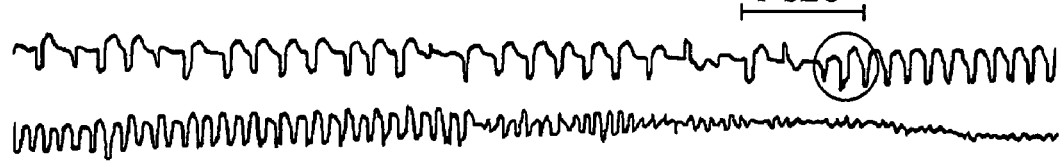
Figure 3:
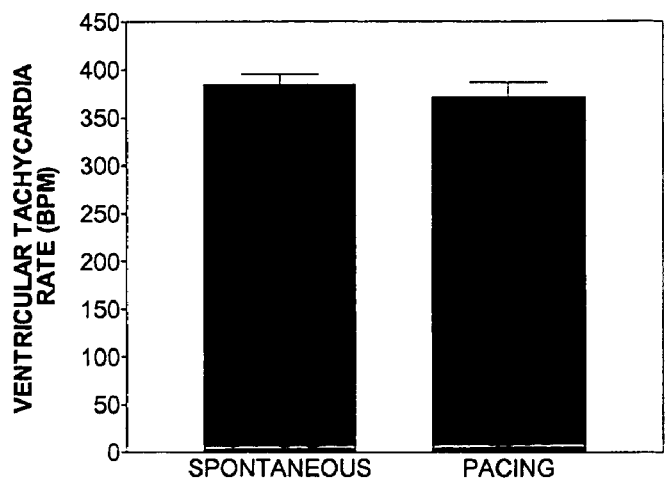
FIG. 3 illustrates spontaneous versus pacing-induced monomorphic ventricular tachycardia.

In the model used to demonstrate the effectiveness of the methods of the present invention, a two stage ligation of the left anterior descending (LAD) coronary artery was performed in the anesthetized dog. The two-stage ligation procedure results in a very low incidence of ventricular fibrillation (<5-10%) during the initial 6 hours following coronary artery occlusion (Harris et al., 1951). Almost all ventricular fibrillation occurs during the initial 30 minutes with a high proportion of successful defibrillation. Ambulatory EKG monitoring is performed over the 2-24 hr period following coronary artery ligation. During the 6-24 hr period, a 25-40% incidence of rapid monomorphic ventricular tachycardia (385±15/min) leading to ventricular fibrillation is observed at 13.3±0.8 hours post-LAD ligation (FIG. 1), with a mean duration of monomorphic ventricular tachycardia preceding ventricular fibrillation of 66±7 sec. An example of spontaneous sustained monomorphic ventricular tachycardia observed in this model is shown in FIG. 2. When provocative ventricular pacing is performed at 24 hours, however, the reentrant substrate supporting sustained ventricular tachycardia is present in more than 80% of the surviving dogs with no difference in rate between spontaneous and pacing-induced sustained monomorphic ventricular tachycardias (FIG. 3).

Figure 4:
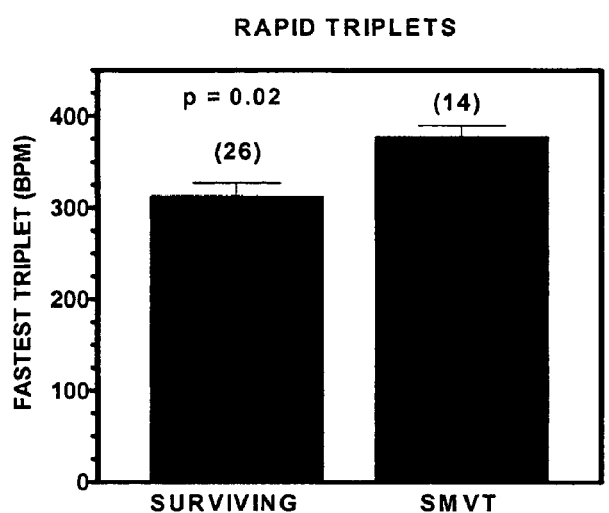
FIG. 4 illustrates the role of very rapid triplets (>360 bpm) in spontaneous sustained monomorphic ventricular tachycardia (SMVT). Both rapid triplets and an underlying reentrant substrate capable of supporting sustained ventricular tachycardia are needed for spontaneous SMVT and sudden death.
Figure 5:
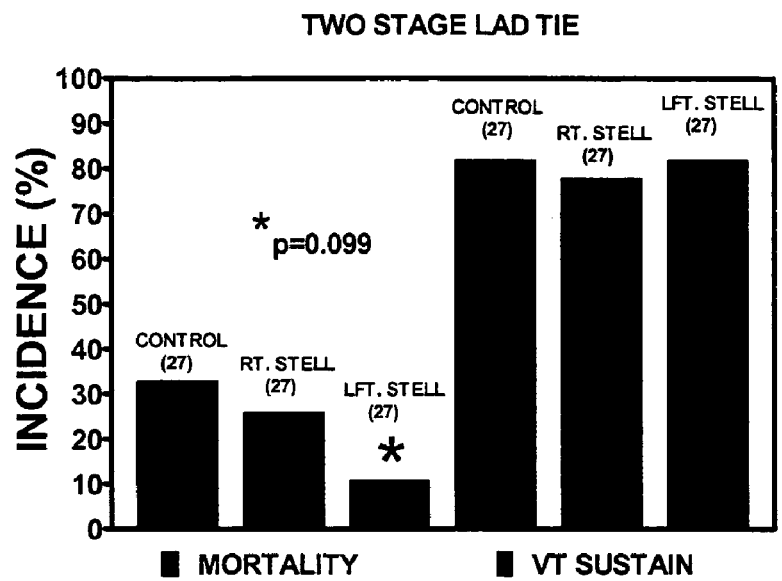
FIG. 5 illustrates the incidence of mortality and sustained ventricular tachycardia occurring spontaneously, plus pacing-induced sustained ventricular tachycardia, in control, acute right stellate ganglionectomy and acute left stellate ganglionectomy treated dogs following two stage LAD tie. Thus 80% of the animals have a subtrate capable of sustaining rapid ventricular tachycardias.
Figure 6:
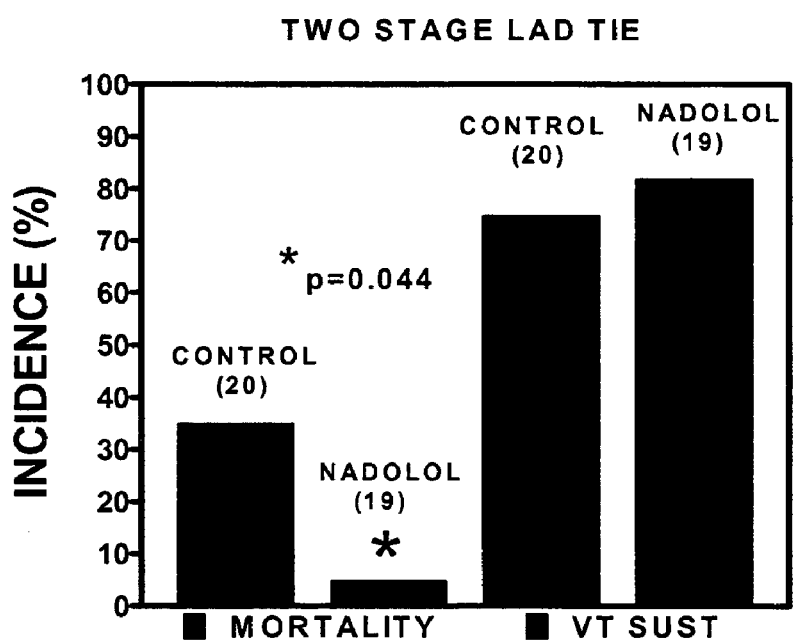
FIG. 6 illustrates the incidence of mortality and sustained ventricular tachycardia in control and nadolol-treated dogs following two stage LAD tie.

If a reentrant substrate capable of sustaining monomorphic ventricular tachycardia is uniformly present 24 hours after LAD coronary artery occlusion, it is interesting why some dogs develop lethal ventricular arrhythmia spontaneously while others survive the early post-infarct period. Survival during the 2-24 hr period following coronary artery occlusion is not determined solely by the presence/absence of a reentrant substrate capable of sustaining ventricular tachycardia, but is also dependent upon the presence/absence of rapid ventricular triplets, a form of non-sustained ventricular tachycardia, capable of triggering sustained monomorphic ventricular tachycardia. Examples of rapid ventricular triplets can be observed in the rapid EKG trace shown in the bottom panel of FIG. 2. Rapid ventricular triplets (at rates >330 bpm) have been circled in FIG. 2. The absence of rapid ventricular triplets is associated with the absence of spontaneous monomorphic ventricular tachycardia and ventricular fibrillation during the 2-24 hr period, despite the presence of an underlying reentrant substrate capable of sustaining monomorphic ventricular tachycardia at rates greater than 300 bpm (FIG. 4). Both the trigger (rapid ventricular triplets) and an underlying reentrant substrate capable of sustaining monomorphic ventricular tachycardia must be present for spontaneous arrhythmia and sudden death.

Figure 7:
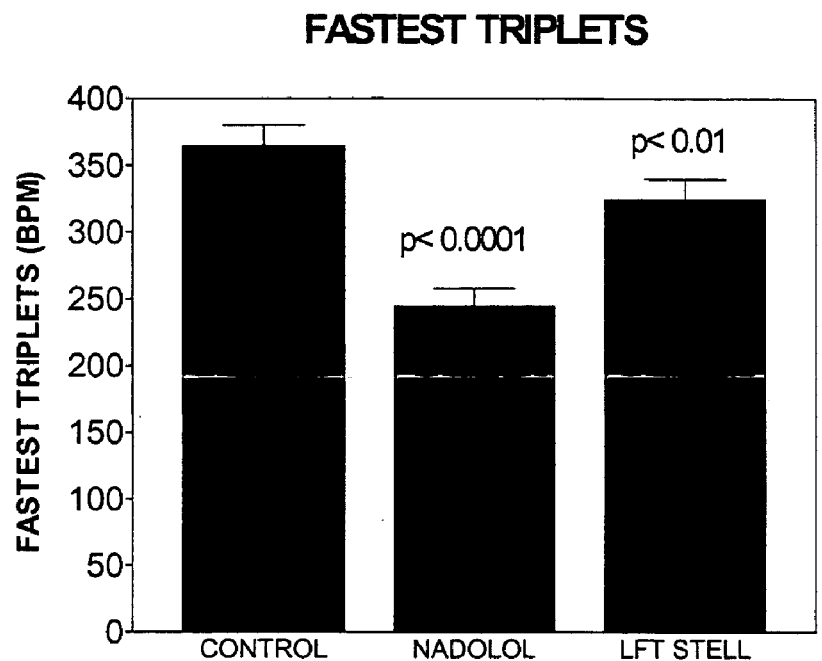
FIG. 7 illustrates the rate of the fastest triplets (BPM) in control, nadolol and acute left stellate ganglionectomy treated dogs following two stage LAD tie.
Figure 8:
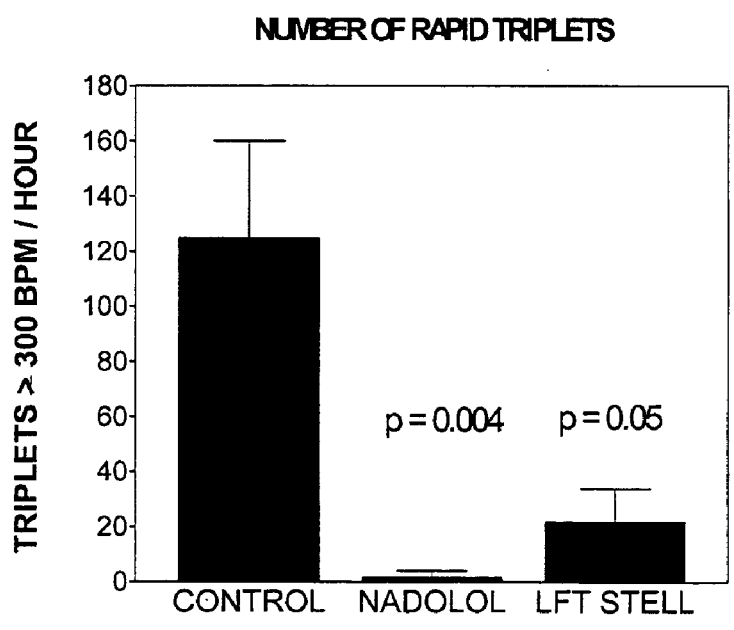
FIG. 8 illustrates the number of rapid triplets (>300 bpm/hour) in control, nadolol and left stell treated dogs following two stage LAD tie.

The sympathetic nervous system plays an important role in the generation of rapid ventricular triplets triggering sustained monomorphic ventricular tachycardia in the 2-24 hr period following coronary artery ligation. Both the non-selective β-adrenergic receptor antagonist, nadolol (Patterson et al., 1986), and acute left stellate ganglionectomy (but not right stellate ganglionectomy)(Patterson et al., 1991) reduce the incidence of sudden death and the incidence of rapid ventricular triplets observed during the 2-24 hr period following coronary artery ligation, without reducing the incidence of pacing-induced sustained monomorphic reentrant tachycardia present in the surviving animals at 24 hours and without altering infarct mass. The results are summarized in FIG. 5 and FIG. 6. Both interventions reduce both the rate and number of rapid ventricular triplets observed during the 2-24 hr period (FIGS. 7 and 8). The data are consistent with the hypotheses that 1) lethal ventricular arrhythmia during the 2-24 hr period following LAD coronary artery ligation can be prevented by selectively suppressing the trigger for the initiation of a potentially lethal reentrant ventricular rhythm, without altering the underlying substrate supporting the reentrant rhythm, and 2) the sympathetic nervous system plays a critical facilitatory role in the generation of the rapid ventricular triplets that initiate sustained monomorphic ventricular tachycardia in the present animal model of sudden coronary death.

The electrophysiologic bases for the rapid ventricular triplets present in vivo during the 2-24 hr period following two stage LAD coronary artery ligation have not yet been determined. The spontaneous evolution of rapid triplets is suppressed with general anesthesia (sodium pentobarbital, alpha-chloralose, or isoflurane anesthesia), preventing in vivo studies of spontaneous triplet formation in the anesthetized dog. Neither is it possible to reproduce rapid triplet formation in vivo, 24 hours post-LAD ligation in the sodium pentobarbital, alpha-chloralose, or isoflurane anesthetized dog with electrical stimulation of one or both stellate ganglia, despite increasing the underlying multifocal ventricular rhythm from a baseline of 180±20 to 271±18 bpm. It is also unknown as to whether the rapid triplets originate from EBZ alone or from both epicardial or endocardial border zone sites.

Despite a failure to reproduce rapid ventricular triplets in the anesthetized dog, it is however possible to initiate triggered firing in vitro, in superfused injured epicardium overlying anterior infarction at 24 hours following LAD coronary artery ligation. Delayed afterdepolarizations (DADs) and triggering are facilitated with both isoproterenol and norepinephrine administration (Dangman et al., 1988). The relatively slow rate of the triggered rhythms (180-240 bpm) observed in vitro is inconsistent with the more rapid triplet rates (300-450 bpm) observed in vivo. The high concentrations of norepinephrine and isoproterenol used to facilitate DAD formation and enhance triggered firing may exceed the extent of local β-adrenergic receptor stimulation achievable even during myocardial infarction. Triggered activity may also originate in ischemically-injured subendocardial tissues at 24 hours (El-Sherif et al., 1983; Le Marec et al., 1985). The same caveats applicable to DAD formation and triggered activity are also applicable to triggered activity elicited from subendocardium, 24 hours post LAD coronary artery ligation. Neither rapid triggered rhythms (>300 bpm) (El-Sherif et al., 1983; Le Marec et al., 1985) nor β-adrenergic sensitivity within the physiologic range have been demonstrated (El-Sherif et al., 1983).

Figure 9:
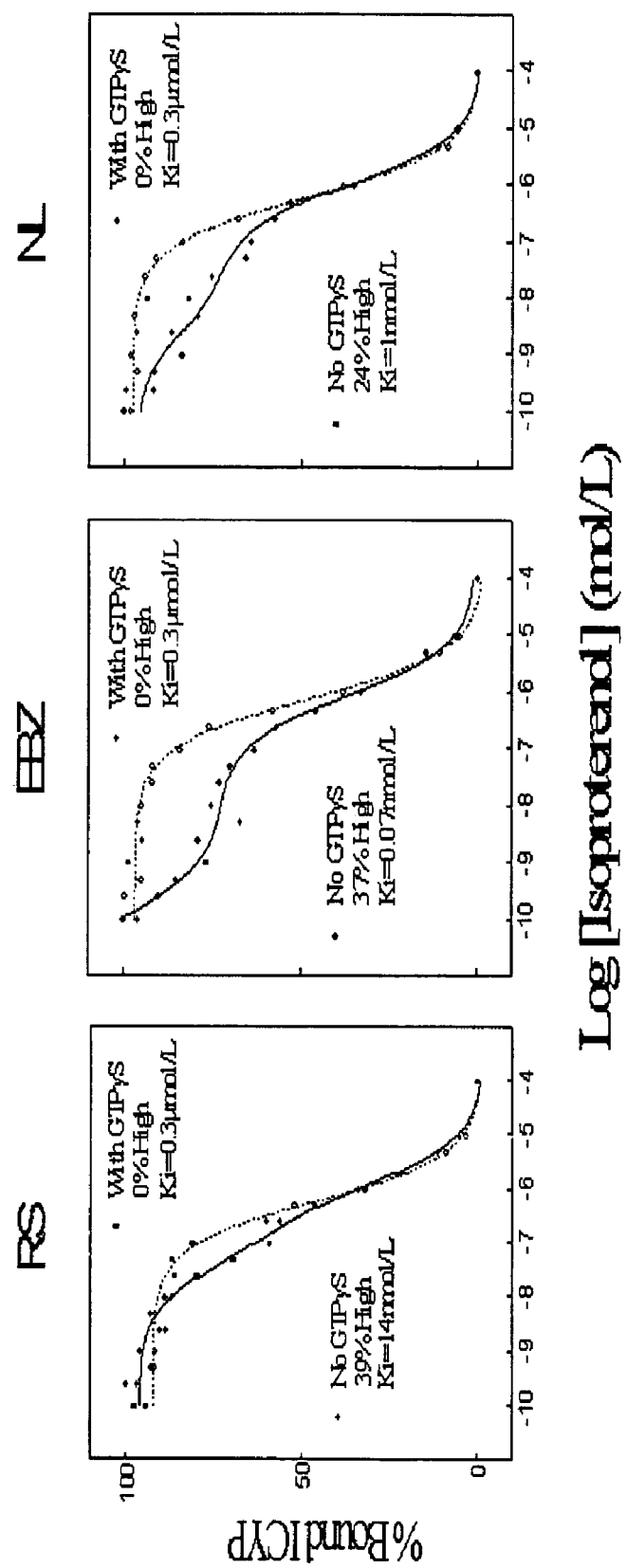
FIG. 9 illustrates composite competition curves (n=6, each point performed in triplicate) of isoproterenol with specific $^{125}$I-CYP binding to myocardial membranes from 24-hour normal surviving myocardium (RS) (left), epicardial border zone tissue (EBZ) (center), and pooled normal tissue (NL) (right). Each displayed similar proportions of receptors showing high affinity binding. There was a highly significant difference (P<0.001, n=6) between high affinity $K_i$ for RS and EBZ. There was no significant difference between $K_i$ for NL and EBZ tissues.

Despite the abbreviated duration of myocardial injury (24 hours) utilized in the present canine sudden death model, the model has important parallels to the lethal arrhythmias recorded from ambulatory patients with coronary artery disease and previous myocardial infarction (Panadis et al., 1983; Kempf et al., 1984). The model incorporates 1) an underlying reentrant substrate capable of sustaining monomorphic ventricular tachycardia, 2) spontaneous ventricular tachyarrhythmias, and 3) increased sympathetic nervous system tone. Experiments performed in the inventor's laboratory have documented increased β-adrenergic receptor sensitivity in injured epicardium overlying infarcted myocardium, 6-24 hours following left anterior descending coronary artery ligation in the dog (FIG. 9). This is in contrast to the surviving normal (RS) tissue which retains the ability to "desensitize" its β receptors. The increased β-adrenergic receptor sensitivity appears to play an important role in the initiation of spontaneous monomorphic ventricular tachycardia and sudden death in dog during the 6-24 hr period following LAD coronary artery ligation. The present invention is directed to potential therapeutic regimens which may help to reduce the high incidence of lethal ventricular arrhythmia observed in the population.

Both increased sympathetic nervous system tone (Malliani et al., 1980) and increased β-adrenergic receptor responsiveness (Cameron et al., 1982) have been documented in injured canine myocardium during the first 24 hours following coronary artery ligation. Although enhanced β-adrenergic receptor transduction within surviving injured tissue may play a role in increased β-adrenergic receptor sensitivity at 5 days post-infarction in the dog (Steinberg et al., 1995), it has been demonstrated by the inventors that increased β-adrenergic receptor sensitivity is present in injured epicardium overlying an anterior infarct. This was demonstrated using a β-adrenergic receptor binding assay ($^{125}$I-iodocyanopindolol) at 24 hours following coronary artery ligation in the dog (Yu et al., 2000). Examples of binding curves for normal surviving myocardium (RS), ischemically-injured epicardial border zone (EBZ), and tissue from a normal heart (NL) are shown in FIG. 9 at 24 hours, with numerical data shown in Table I.

TABLE I

| β-Adrenergic Receptor Binding | | |
|---|---|---|
| | Normal Zone | Remote Site |
| $B_{max}$ (fmol/mg) | 35 + 2 | 38 + 3 |
| K (low affinity) (nM) | 1.2 + 0.9 | 13.8 + 2.8* |
| K (high affinity) (nM) | 0.42 + 0.06 | 0.73 + 0.16+ |

*p < 0.01,
+p = 0.07 versus NZ

Figure 10:
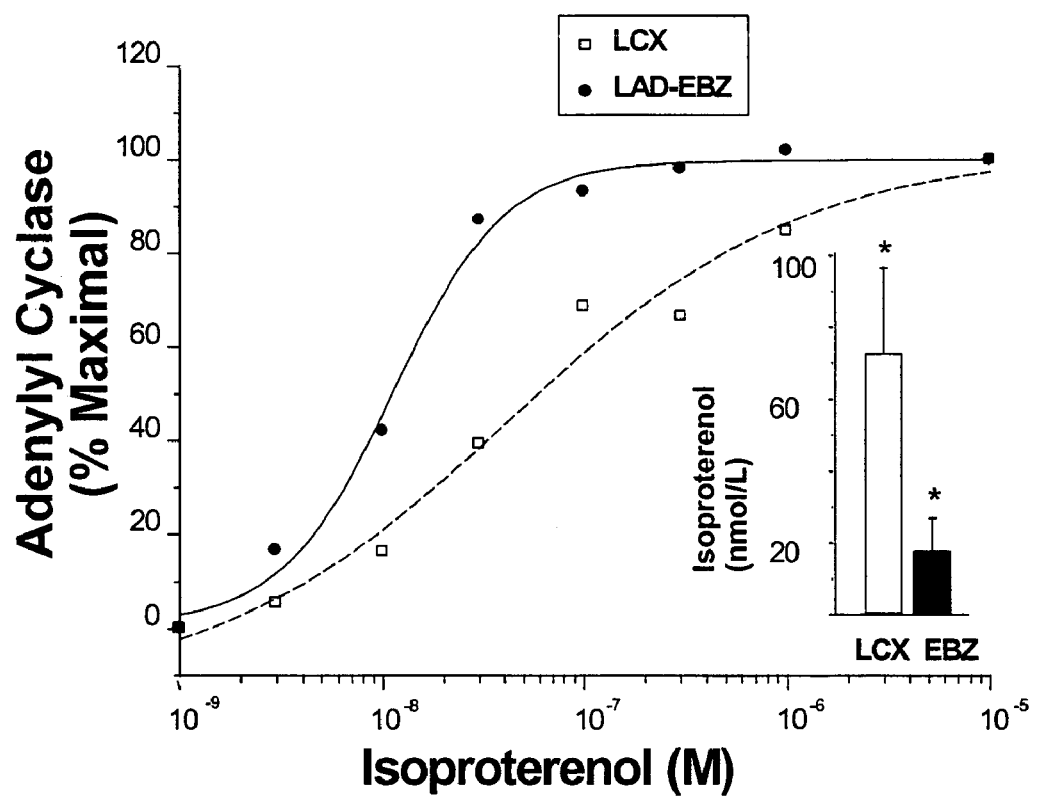
FIG. 10 illustrates an isoproterenol-AC activity dose-response curve in EBZ and RS tissue obtained 24 hours after LAD ligation. Data are shown for 1 of 4 experiments. Each point is mean of duplicate samples. RS dose-response curve was shifted to right. Mean $EC_{50}$ value for RS (inset) was significantly different from EBZ (73±22 vs 18.0±8.9 nmol/L [SEM]) (P<0.05, n=4).
Figure 11:
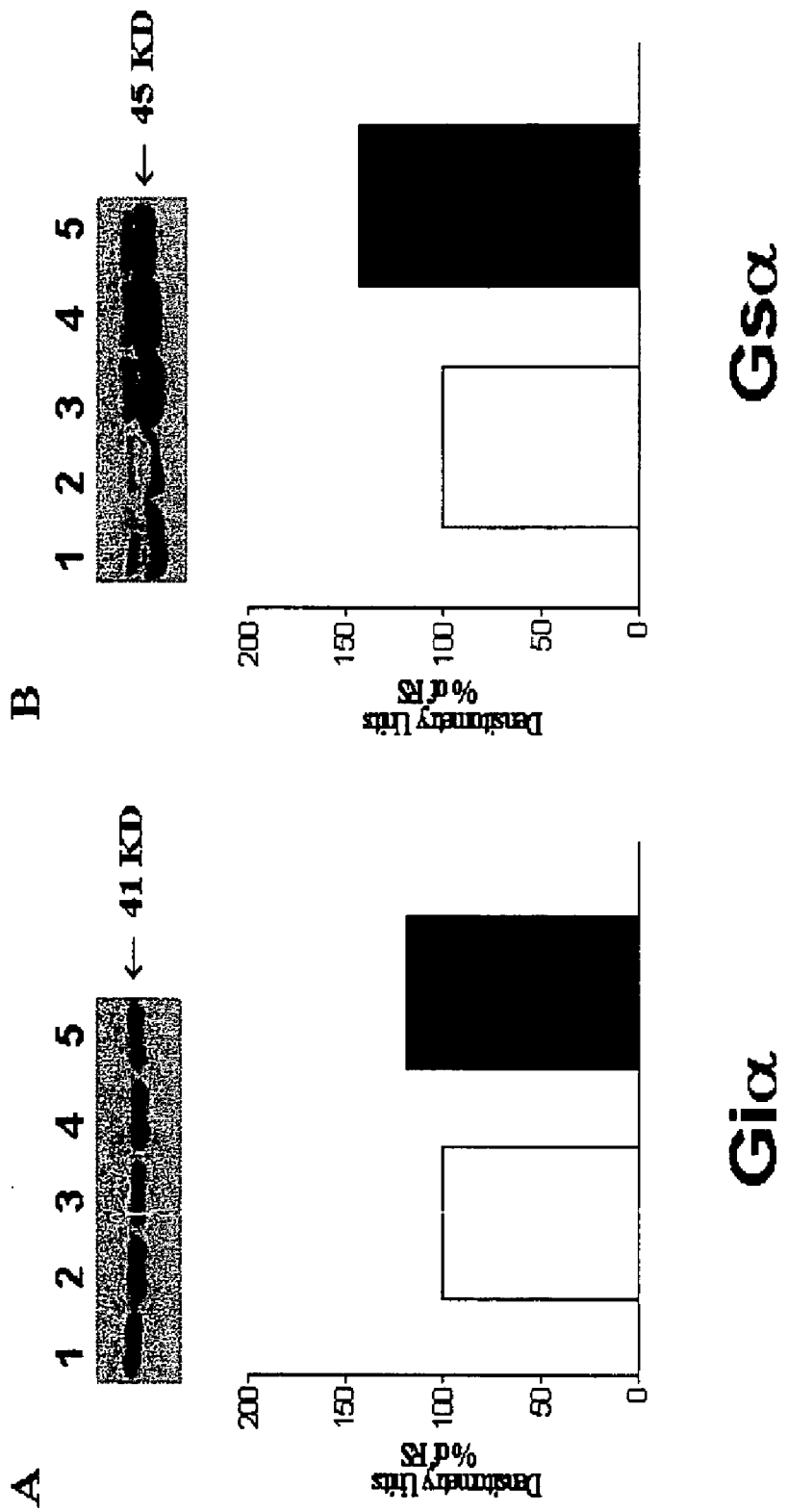
FIG. 11 illustrates GRK2 (β-ARK) activity in cytosolic and pellet fractions of the EBZ tissue expressed as % of (RS).
Figure 12:
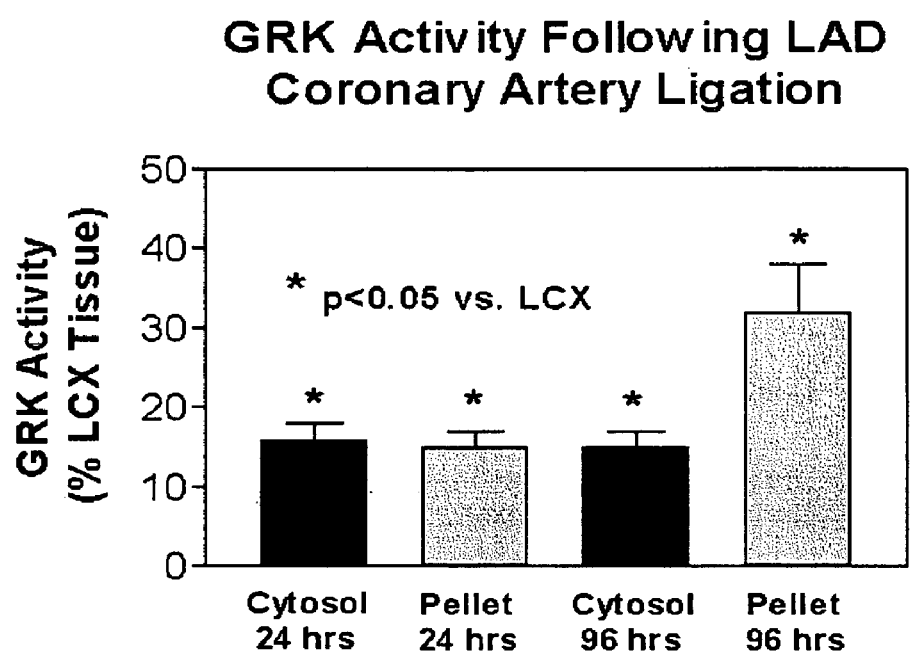
FIG. 12 illustrates GRK activity (as % left circumflex control tissue (LCX)) following LAD coronary artery ligation in the cytosol and pellet at 24 and 96 hours.

The increased β-adrenergic receptor sensitivity has important physiologic consequences and is translated into increased adenylate cyclase activity and c-AMP formation with isoproterenol administration (FIG. 10). The increased β-adrenergic responsiveness at 24 hours post LAD ligation cannot be attributed to significant changes in Gs or Gi proteins mediating G-protein receptor transduction (FIG. 11).

Figure 13A:
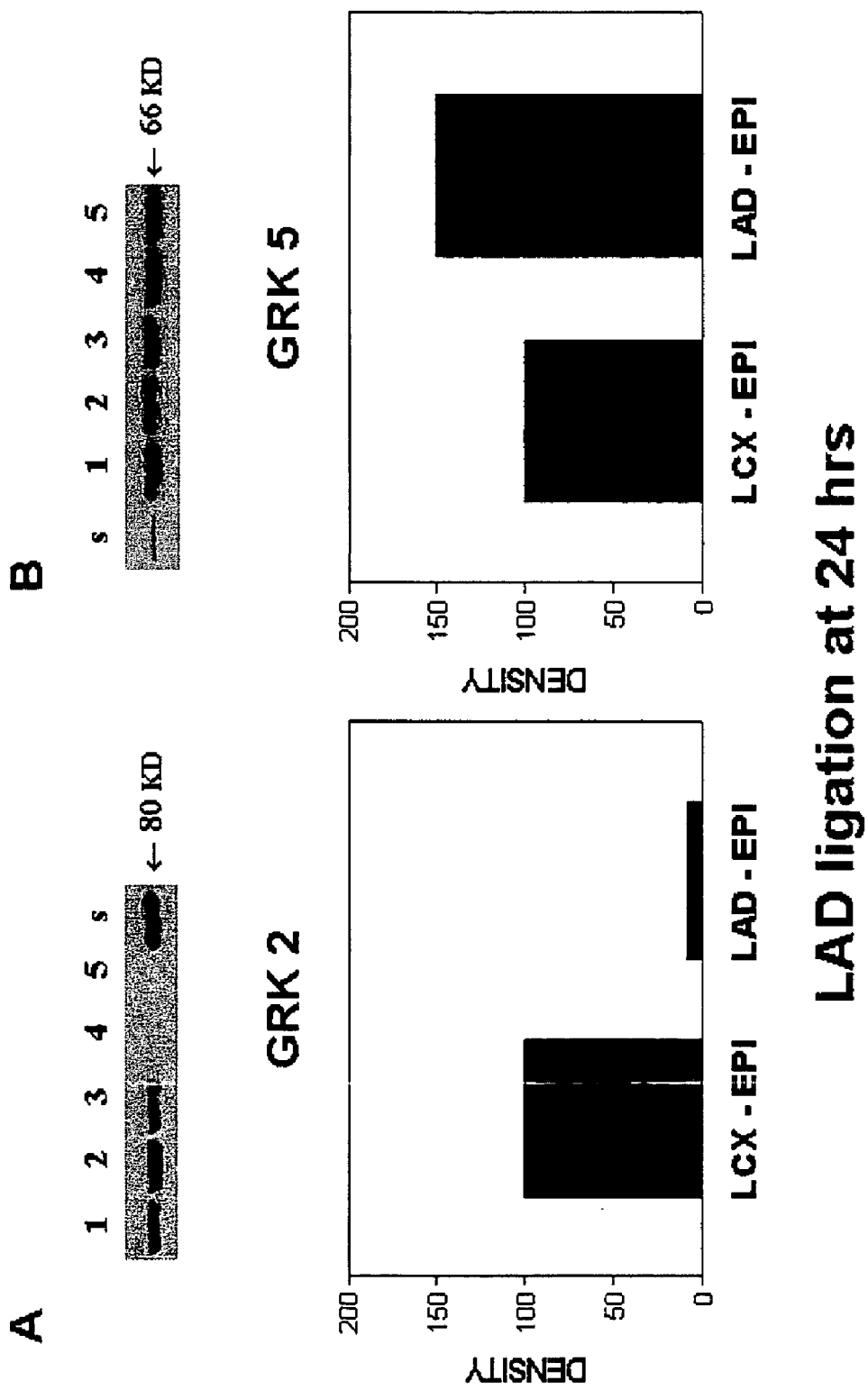
FIG. 13A illustrates representative immunoblots of (A) β-ARK (cytosol) and (B) GRK5 (membrane) from nonoperated normal animals and 24-hour CAL tissue. Lane 1, normal RS; lane 2, normal EBZ; lane 3, RS; lane 4, EBZ; lane 5, infarct; lane s, purified β-ARK (A) or GRK5 (B). Relative density of GRK for EBZ (n=6) is expressed as a percentage of RS (100%), and mean values are shown in bar graphs. The β-ARK level in EBZ was significantly decreased by use of a nonparametric sign test (*P=0.03, n=6). Rise in GRK5 did not reach significance (NS).
Figure 13B:
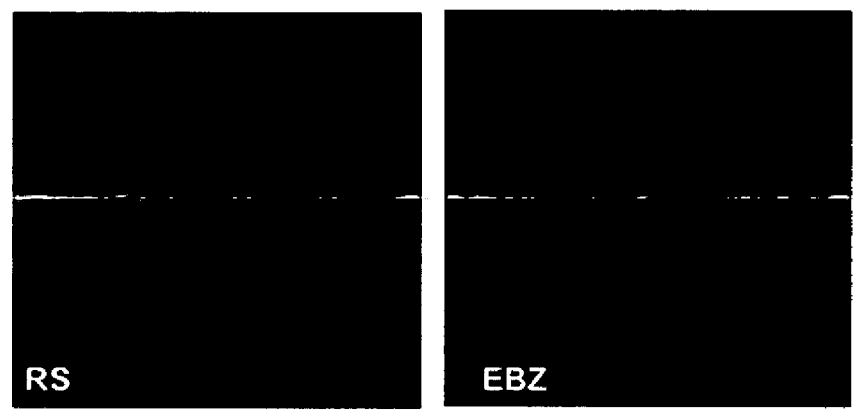
FIG. 13B illustrates immunofluorescence staining for β-ARK in frozen sections taken from the remote site (RS) and ischemic subepicardial border zone (EBZ) tissue of the 24-hour LAD-ligated dog. There is a >50% decrease in β-ARK FL in the EBZ compared to RS tissue (*P<0.01, n=30 cells). These parallel the significant decrease in β-ARK activity and protein content by immunoblot.
Figure 13B:
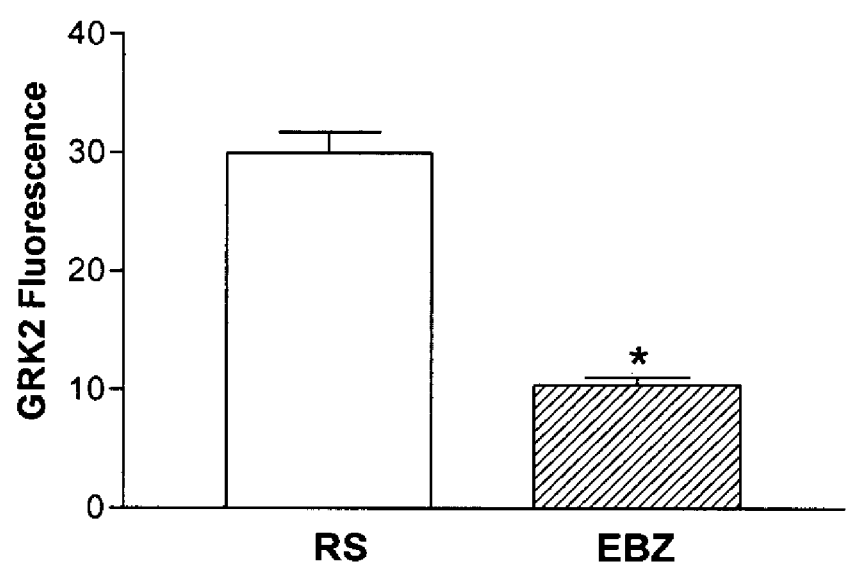
Figure 14:
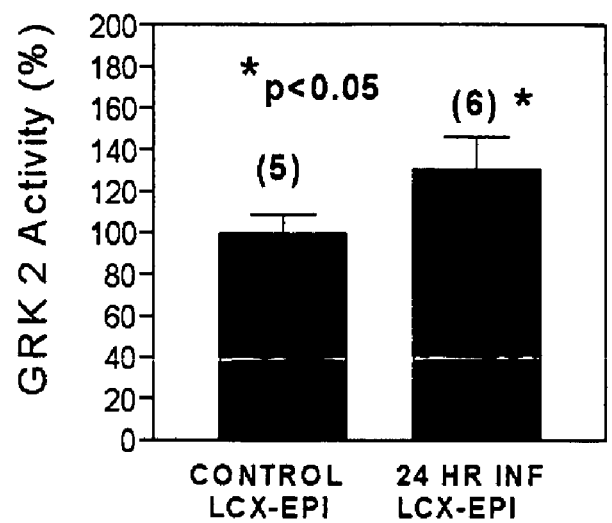
FIG. 14 illustrates that GRK2 (β-ARK 1) is increased in non-ischemic myocardium taken from an infarcted animal (24 hour infarct LCX) at 24 hours post LAD ligation compared to normal (control LCX) myocardium.

Desensitization of G-protein receptors, including β-adrenergic, adenosine, muscarinic, and angiotensin receptors, occurs by: 1) ligand-independent phosphorylation through protein kinase A and 2) ligand-dependent phosphorylation through β-adrenergic receptor kinase. It is proposed that increased β-adrenergic receptor sensitivity and increased isoproterenol-stimulated c-AMP formation results directly from decreased β-adrenergic receptor kinase-1 expression/activity (β-ARK-1) within injured epicardium. β-ARK-1, by phosphorylating ligand-activated β-adrenergic receptors, desensitizes the β-adrenergic receptor and precipitates its internalization from the cell membrane to the cell interior by an obligate transport protein, β-arrestin (Pitcher et al., 1998; Bunemann et al., 1999; Krupnick et al., 1998). βARK-1, a G-receptor kinase of the superfamily of G-receptor inactivating enzymes, is the principal mechanism providing for the desensitization and the termination of β-adrenergic receptor stimulation in myocardium and other tissues (Pitcher et al., 1998; Bunemann et al., 1999; Krupnick et al., 1998). The decrease of β-ARK-1 in injured myocardium has been determined by direct measurement of myocardial β-ARK-1 activity (FIG. 12), immunoblot of β-ARK-1 expression (FIG. 13A), and immunohistofluorescence of myocardial β-ARK-1 content. Only a partial recovery of β-ARK-1 activity was observed at 96 hours (FIG. 13B). It appears that the decrease in β-ARK-1 in ischemically-injured myocardium results from an increased degradation of β-ARK-1 in ischemically-injured epicardium.

The distribution of G-receptor kinase (GRK-5) is paradoxically-increased rather than decreased in ischemically-injured epicardial tissue and thus differs reciprocally in expression from β-ARK-1 (FIG. 13)(Yu et al., 2000). The increase in GRK-5 expression in the EBZ does not appear to play an important role (as opposed to β-ARK-1) in desensitizing β-adrenergic receptors within injured epicardium at 24 hours. The increase in GRK-5 may however alter desensitization of other G-protein coupled receptors in injured canine epicardium (Pitcher et al., 1998; Bunemann et al., 1999). In particular, increased GRK-5 may increase the desensitization of adenosine and muscarinic receptors within injured myocardium. Stimulation of these G-coupled receptors is capable of decreasing c-AMP formation initiated by intense β-adrenergic receptor stimulation and may thereby reduce the electrophysiologic actions mediated via the β-adrenergic receptor (Isenberg et al., 1984; Hartzell, 1988). The roles played by both of these receptors in the setting of ischemic-injury are largely unknown, although cholinergic agonists and vagus nerve stimulation reduce the development of lethal ventricular arrhythmias in another model of sudden death associated with high sympathetic nervous system tone (De Ferrari et al., 1993; Vanoli et al., 1991). Therefore, it is considered likely that the increase in GRK5 will desensitize muscarinic and adenosine receptors and may further lead to a substrate with increased susceptibility to β receptor stimulation.

The decrease in β-ARK-1 in injured myocardium must be clearly differentiated from the increase in β-ARK-1 observed in normal tissues as a result of increased β-adrenergic receptor stimulation, a direct result of chronic high sympathetic nervous system tone and exposure to increased catecholamine concentrations. β-adrenergic receptors in control epicardium within the LCX coronary artery distribution at 24 hours are desensitized, associated with a significant increase in β-ARK-1 activity (FIG. 14) and a reduced sensitivity to action potential shortening with isoproterenol administration ($EC_{50}$=0.47+0.15 vs. 14.3+5.0 nM, control normal tissue vs. remote site normal tissue, 24 hours post LAD ligation, respectively, p<0.01)(Rockman et al., 1998). This information is consistent with increased β-ARK-1 activity and decreased β-adrenergic receptor sensitivity in ventricular myocardium with chronic catecholamine administration or the converse, a decrease in β-ARK-1 with prolonged β-adrenergic receptor blockade (Pye et al., 2003).

Desensitization of PAR occurs by: 1) ligand-independent phosphorylation through PKA (and PKC), and 2) ligand-dependent phosphorylation through G-protein coupled receptor kinases (Benovic et al., 1986). β-ARK and its homologue GRK5 are expressed in canine cardiac tissue. Members of the β-arrestin protein family are necessary co-factors for βAR desensitization by β-ARK and GRK5. These kinases and their regulation have been extensively reviewed (Pitcher et al., 1986; Krupnick et al., 1998; Bunemann et al., 1999). β-ARK and GRK5 interact with both $β_1$ and $β_2$AR, diminish the affinity of βAR for their agonist (desensitization), and with β-arrestin inhibit receptor interaction with the Gsα subunit, and initiate internalization of the β-ARK and βAR into endosomes. This cycle is completed by dephosphorylation and either proteolysis or reconstitution with the cytoplasmic membrane and re-sensitization.

Changes in GRK activity are inversely reflected by βAR sensitivity. Models of congestive heart failure, ischemic myocardopathy (Hammond et al., 1992; Bristow et al., 1989) or mice overexpressing β-ARK or GRK5 have a decreased responsiveness to βAR agonists (Koch et al., 1995; Rockman et al., 1998). Conversely, when β-ARK translocation to the cell membrane is suppressed in transgenic mice by overexpression of the β-ARK carboxyl terminus (β-ARKct), the tissue becomes more responsive to βAR stimulation (Koch et al., 1995; Rockman et al., 1998; Rockman et al., 1997). The inventors have reported that a rapid decrease in EBZ β-ARK occurs by 6 hours and continues through 96 hours; and is associated with increased βAR sensitivity when measured at 24 hours. This was demonstrated using a βAR binding assay ($^{125}$I-iodocyanopindolol) and by an increased adenylate cyclase activity responsiveness to the β-agonist isoproterenol (Yu et al., 2000). This increased βAR sensitivity has important pathophysiologic consequences and cannot be attributed to significant changes in Gs or Gi proteins mediating G-protein receptor transduction (Yu et al., 2000).

There are important differences in control of β-ARK and GRK5 (Pitcher et al., 1998; Krupnick et al., 1998; Bunemann et al., 1999). β-ARK is primarily located in the cytosol and is translocated to the membrane upon activation. β-ARK contains a (~100 aa) C terminal (ct) pleckstrin homology (PH) domain that interacts with PKC isoforms, βγ subunits of G proteins, phosphatidylinositol4,5-bisphosphate (PIP2), and other phospholipids. This PH domain is critical for targeting of β-ARK to the membrane-bound βγ subunit for interaction with βAR. Transgenic overexpression of the PH peptide will block β-ARK translocation to the membrane and inhibit activation of β-ARK. An ischemia-mediated diminution of the phospholipids PIP2 and phosphatidylserine (PS) also decrease β-ARK activity.

PKC phosphorylation of β-ARK increases its activity (Pitcher et al., 1998; Krupnick et al., 1998; Chuang et al., 1995). This occurs after stimulation of G-protein receptors such as $α_1$AR which activate the phospholipase C transduction system and increase β-ARK activity (Akhter et al., 1997). GRK5 contains a PKC-sensitive domain (565-572) that when phosphorylated inhibits GRK5 activity. This differential effect of PKC regarding β-ARK and GRK5 may be of importance in cardiomyocytes under conditions that activate PKC such as ischemia (Joyeux et al., 1997; Yamashita et al., 1997; Arnaud et al., 2003). Several PKC isoforms are increased during myocardial ischemia. This occurs after brief periods of ischemia and is closely related to myocardial protection (ischemic preconditioning). Although several isoforms are increased, the protective effects appear to be most closely related to changes in $PKC_ε$ (Ping et al., 1999; Dorn et al., 1999; Liu et al., 1999). These are usually associated with brief periods of ischemia lasting only 4-30 minutes and are studied after a subsequent period of 90-120 minutes ischemia leading to infarction. GRK5 is membrane-bound but has not been reported to affect βAR sensitivity unless markedly overexpressed in transgenic myocardial cells (Oppermann et al., 1996; Choi et al., 1997). Evidence supports a role for GRK5 modulation of muscarinic signaling of parasympathetic pathways (Gainetdinov et al., 1999) and for thrombin-activated signaling in endothelial cells (Tiruppathi et al., 2000).

Expression of the β-ARK inhibitor adeno-β-ARKct in isolated cardiomyocytes markedly diminished $β_1$AR and $β_2$AR desensitization within 36 hours (Drazner et al., 1997). Conversely, overexpression of β-ARK by an adeno-β-ARK transgene increased βAR desensitization and diminished responsiveness to β-agonists. These changes in β-ARK activity with inversely related changes in β-agonist responsiveness of the cardiac tissue demonstrate an important role for β-ARK in modulating βAR responsiveness in vivo. Changes of GRK activity may produce an altered cellular EP response to βAR agonists. Several studies have reported that β-ARK, β-ARK mRNA and GRK activity are upregulated by increased catecholamines and diminished by β-blockade (Iaccarino et al., 1998; Ping et al., 1995).

GRK degradation is not clearly understood (Pitcher et al., 1998; Krupnick et al., 1998; Bunemann et al., 1999). Internalization of the βAR-β-ARK -β-arrestin complex leads to endosomal degradation of βARK and/or recycling to the cytosol. The proteasome degradation pathway has been proposed as an important alternative mechanism for β-ARK degradation and modulation of desensitization of βAR-mediated signal transduction (Penela et al., 1998; Li et al., 2000; Penela et al., 2001; Elorza et al., 2003; Luo et al, 2003). β-ARK is subject to ubiquination, a necessary step directing proteins to proteasome degradation. There is no evidence that proteasome degradation holds for GRK5. The ubiquitin-proteasome pathway is also involved in transcription control. When eukaryotic cells are exposed to DNA-damaging agents, one of their first priorities is to repair transcriptionally active genes (Svejstrup, 2002). This mandate is achieved, in part, when active RNA polymerase II (having stalled at a DNA lesion) is ubiquitinated and presumably destroyed by the proteasome (Lee et al., 2002). The ubiquitin-proteasome pathway can regulate transcription by controlling transcription factor location (e.g. NF-κB (Palombella et al., 1994) and Spt23 (Rape et al., 2001)), thereby controlling the association of transcription factor with its partner protein (Ostendorff et al., 2002), and controlling transcription factor levels by destroying them (Polakis, 2000; Aberle et al., 1997; Haupt et al., 1997; Maxwell et al., 1999). These mechanisms may also co-exist with ischemia-induced decreases of β-ARK.

In experimental models of myocardial infarction, there are two periods at highest risk for SCD during the first 24-hr after induction of ischemia (Patterson et al., 1991; Patterson et al., 1991; Opitz et al., 1995; Zehender et al., 1991). The first peak is within thirty minutes and the second peak between 5-24 hours after coronary artery ligation (CAL). Human studies indicate the risk of SCD from reperfusion-induced ventricular arrhythmias is highest during the first 24-hr (Zehender et al., 1991). Human and animal studies demonstrate that β-blockade markedly diminishes SCD. These data suggest that additional studies of βAR sensitivity and its relationship to changes in β-ARK activity are needed during the acute and subacute (0.05-6 hours) following induction of cardiac ischemia.

It has been shown herein above that β-ARK expression and activity is significantly decreased in EBZ tissue (Yu et al., 2000). This was observed using direct measurements of β-ARK activity (FIG. 11), by immunoblot analysis of β-ARK expression and by semiquantitative immunofluorescence of β-ARK in myocardial sections (Yu et al., 2003; Yu et al., 2004; Yu et al., 2001). It has been demonstrated that increased βAR sensitivity and isoproterenol-induced c-AMP formation was related to decreased EBZ β-ARK expression/activity (Yu et al., 2000).

Figure 15:
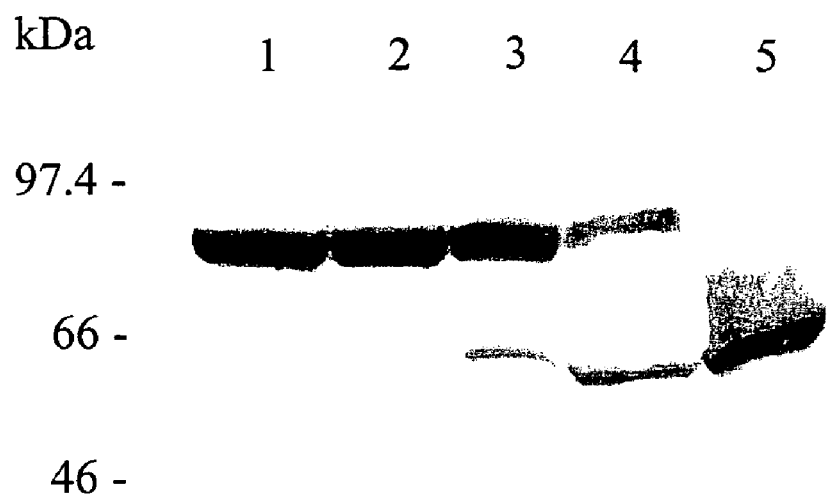
FIG. 15 illustrates an immunoblot showing β-ARK degradation after 24-hour LAD ligation using anti- β-ARK antibody. Protein (150 μg/lane) was subjected to SDS-PAGE. Lane 1: Control (Remote Site) from non-infarcted control dog; Lane 2: Control (EBZ) from non-infarcted dog; Lane 3: RS tissue from 24-hr infarcted dog; Lane 4: EBZ tissue from 24-hr infarcted dog; Lane 5: INF tissue from 24-hr infarcted dog.

This decrease of β-ARK expression/activity in EBZ tissue could be caused by decreased transcription, increased degradation by the proteasome pathway or by other proteolytic pathways. FIG. 15 demonstrates an immunoblot using anti-β-ARK antisera on tissues obtained just 24-hr after ligation in cardiac tissues taken from a sham-operated control dog (lanes 1&2) and from an infarcted dog (lanes 3-5). The tail is inversely proportional to the relative destruction of the β-ARKS and is equivalent to laddering seen with other blots involving degradation of a protein or RNA. These changes were not always apparent at 24-hr indicating that this process occurs rapidly after onset of ischemia.

Effect of Inhibition of Tumor Necrosis Factor α in Dog Models of Rapid Ventricular Tachycardia (FIGS. 16-21)

TNFα increases in myocardial infarction (Vaddi et al., 1994; Kukeilka et al., 1995; Herskowitz et al., 1995; Chandrasekar et al., 1997) and may have an important role in modifying the EP events and signal transduction following LAD ligation. The following figures and description demonstrate a significant increase of β-ARK expression in EBZ tissue in etanercept-treated dogs compared with control dogs. This was associated with a significant reduction in infarct size. There was a significantly decreased frequency of rapid monomorphic triplets during continual Holter monitoring of the etanercept-pretreated infarcted dogs.

Two different dog models were selected for their unique abilities to best demonstrate these diverse effects following induced acute myocardial infarction. These data together demonstrate that TNFα sequestration by etanercept prior to induction of myocardial ischemia has the capacity to substantially reduce ventricular tachyarrhythmias known to predispose to ventricular fibrillation and SCD; and to markedly decrease infarct size. In addition, TNFα sequestration significantly attenuates the expected loss of tissue βARK in susceptible ischemic ventricular tissue and may exert a β-AR agonist protective effect.

Etanercept (2 mg/kg), a TNFα sequestrant was administered 24- and 1-hr prior to LAD coronary artery ligation to examine the role of TNFα on lethal ventricular tachyarrhythmias and myocardial necrosis. Dogs treated with etanercept had decreased very-rapid (>360 bpm) ventricular triplets (6±1/hr, n=8) 2 to 24 hr following coronary artery ligation compared to saline (21±6/hr, n=10, P<0.05). This was concordant with 8-fold salvage of β-adrenergic receptor kinase 1 (βARK) activity compared to control (33.8±7.2% vs 4.3±2.2% of unoperated control tissue, P<0.01, n=5). Salvage of βARK occurred without change in the thickness of the epicardial tissue overlying the infarct. In dogs pretreated with etanercept prior to 2-hr occlusion/4-hr reperfusion of the LAD coronary artery, infarct mass decreased by 61% (% area at risk) and 54% (% left ventricular mass) in the etanercept group (n =8) compared to saline (n=9, P<0.05). This was concordant with an etanercept-mediated 9-fold decrease in leukocyte accumulation within ischemically injured myocardium. TNFα antagonism decreases malignant ventricular tachyarrhythmias and may relate to partial protection of normal βARK-mediated desensitization of β-adrenergic receptors. TNFα sequestration also decreases infarct size in an occlusion/reperfusion model of myocardial ischemia.

All dogs with a documented infarct by EKG and visual inspection were included in the groups. Any dog without an apparent infarct was re-inspected for collateral vessels that were not apparent because of the limited field of surgery during coronary artery ligation. In either case, those dogs without apparent infarct were not included in the study.

Figure 16A:
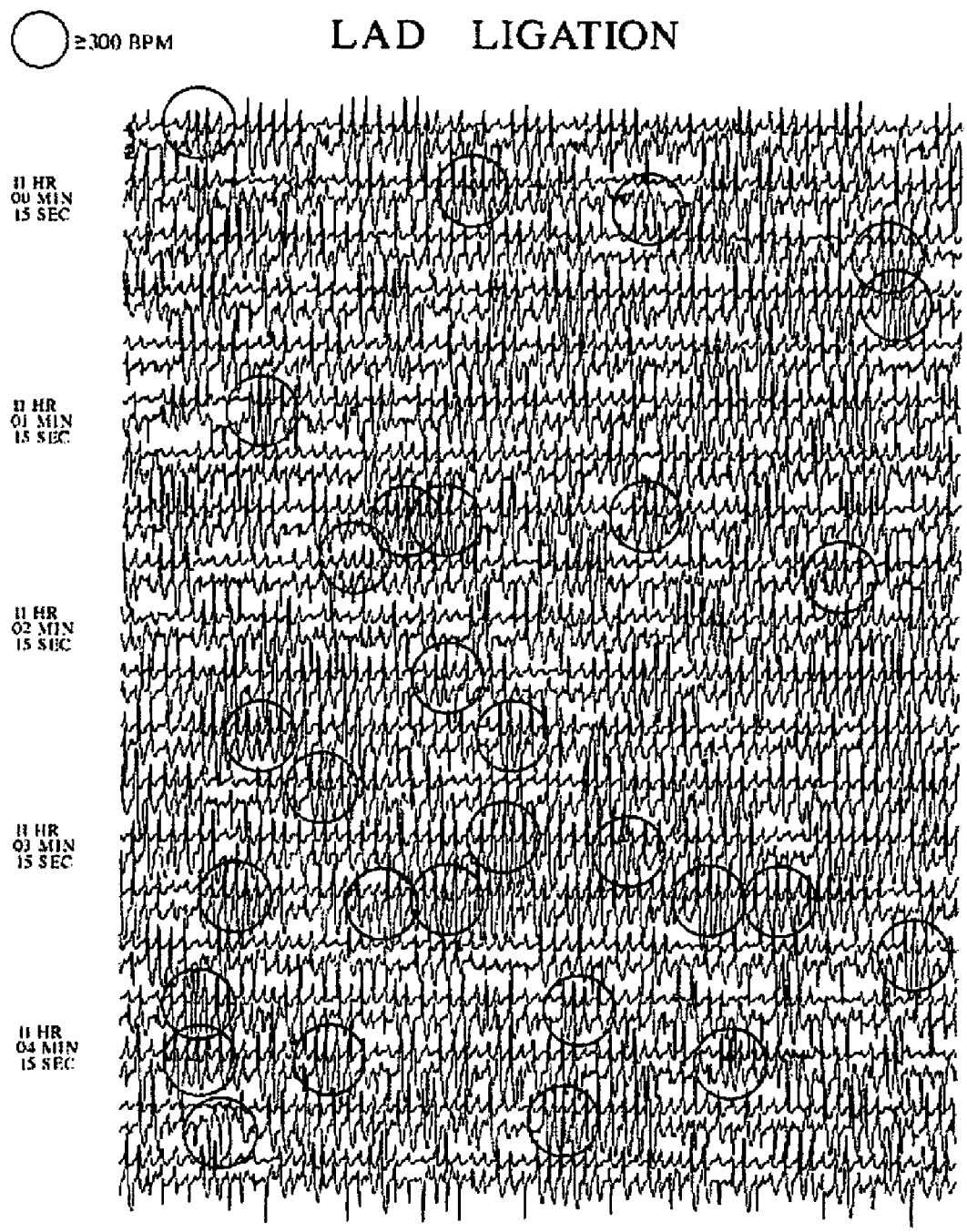
FIG. 16A shows an individual EKG tracing from a control dog, 11-hours after LAD ligation. All rapid ventricular triplets (≧300 bpm) are circled. An EKG tracing recorded beginning 11 hr 30 min after LAD ligation is shown in FIG. 16B for an etanercept-treated dog. Note the slower idioventricular heart rate and the absence of rapid triplets in the etanercept-treated dog.
Figure 16B:
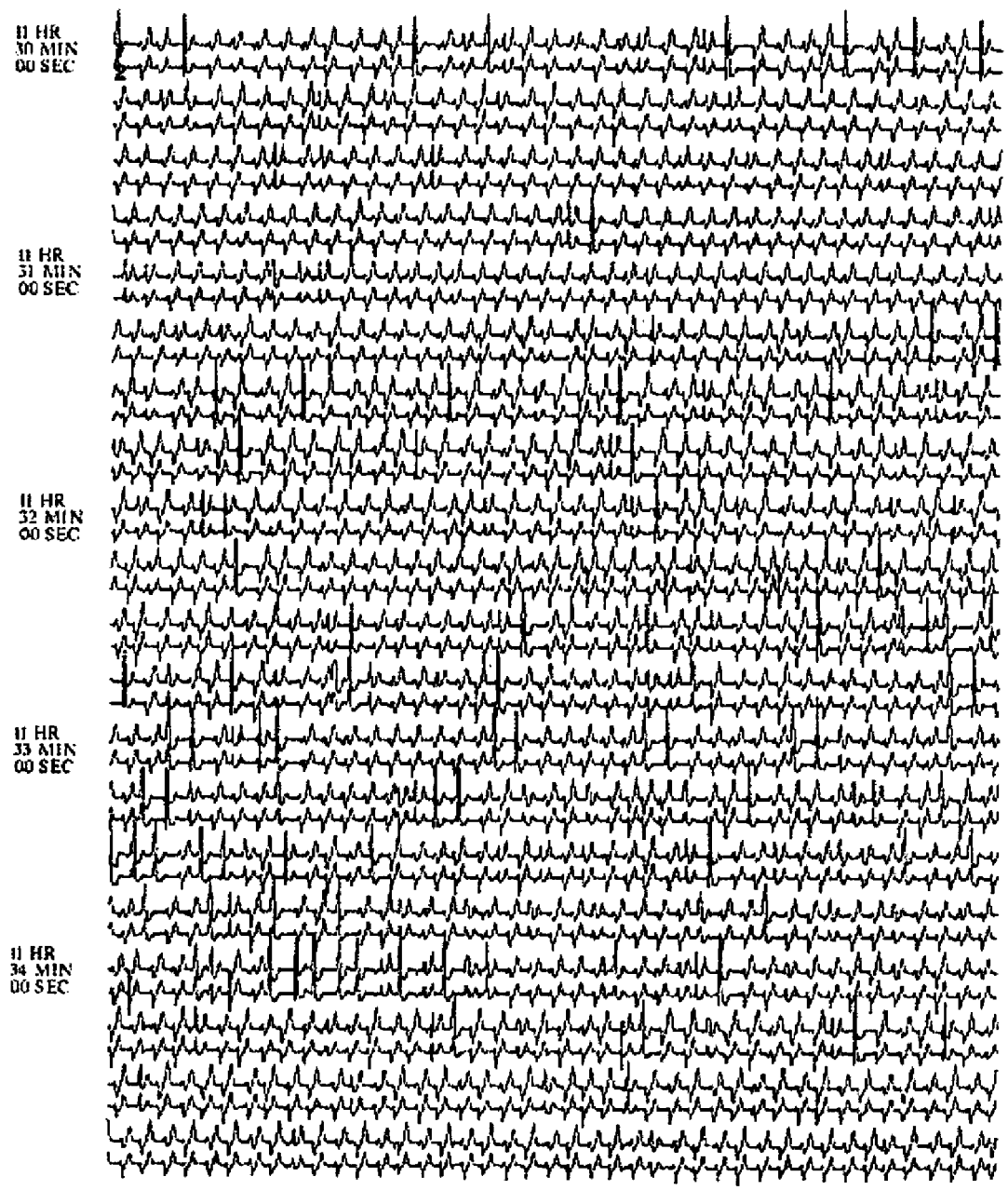
FIG. 16 illustrates EKG recordings of representative saline and etanercept-treated dogs following LAD ligation.
Figure 17A:
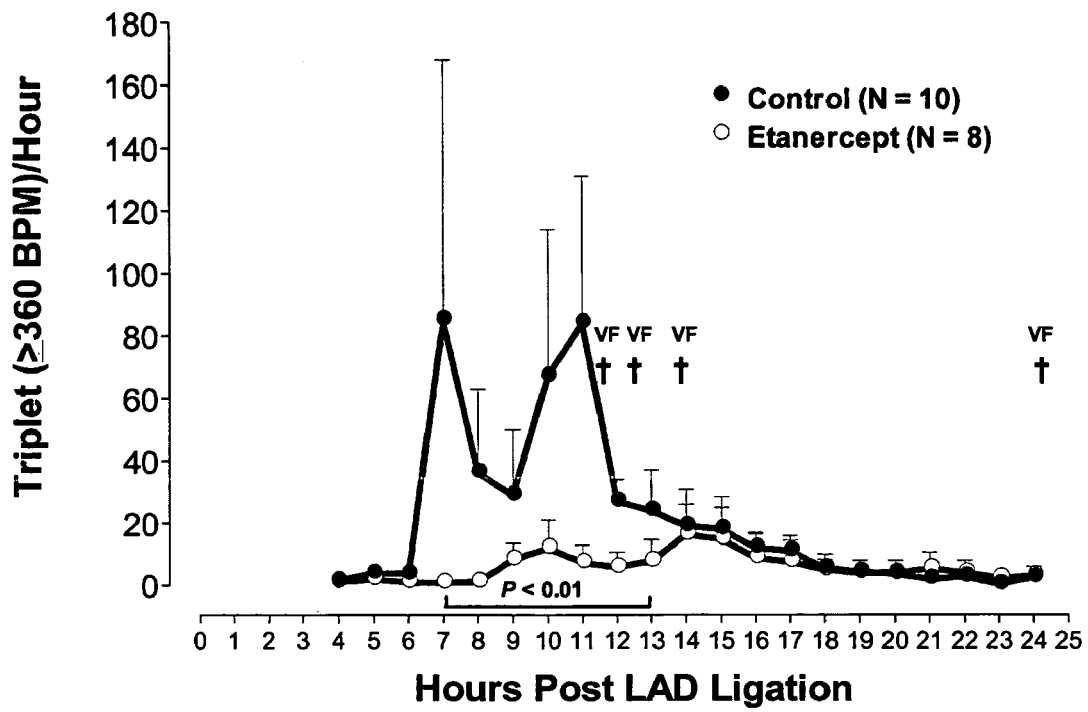
FIG. 17A shows the incidence (mean±SEM) of very rapid ventricular triplets (≧360 bpm) per hour for control (closed circles, n=10) and etanercept-treated (open circles, n=8) groups. The times of death of four dogs in the control: group are marked with † (VF, ventricular fibrillation). The two groups had equivalent numbers of very rapid triplets after the three dogs at greatest risk had died.
Figure 17B:
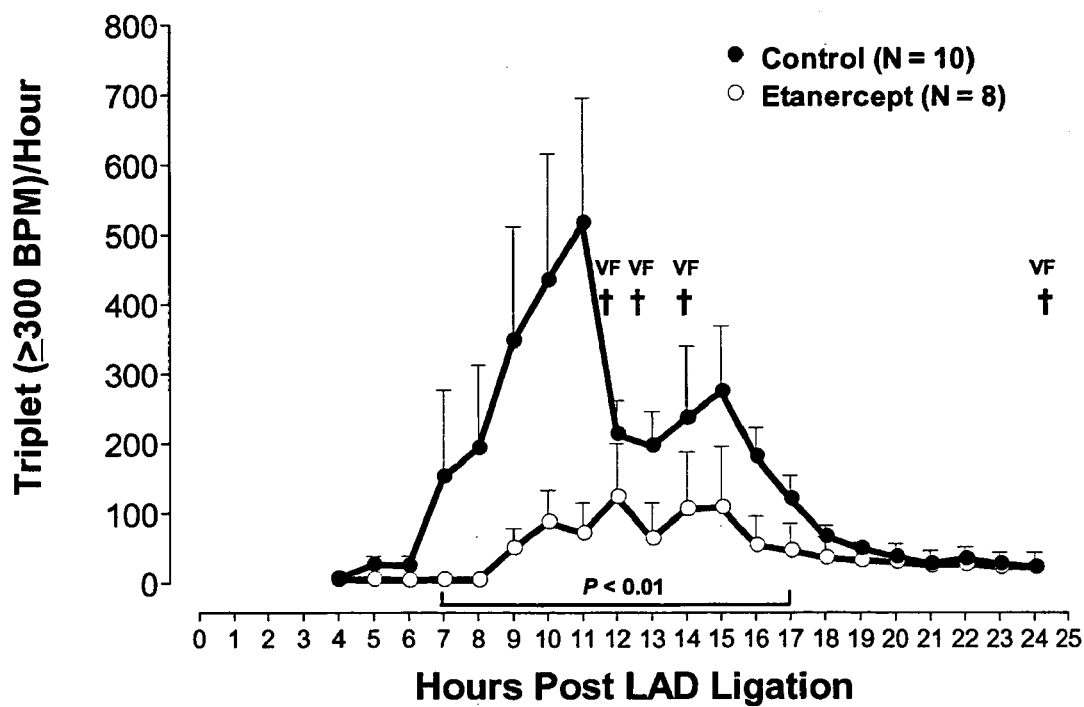
FIG. 17B demonstrates all of the rapid triplets (≧300 bpm) for the two groups. The saline control animals generally had a significantly greater number of total triplets (≧300 bpm) throughout the time period.

In the 24-hr Infarct (Model 1) Studies, each control and etanercept pretreated animal was monitored for ventricular arrhythmias using a Holter 2-lead recording for the duration of time following LAD ligation. EKG recording following LAD ligation demonstrated an increased number of rapid (≧300 bpm) ventricular triplets in the saline-treated dogs (FIG. 16A). The etanercept-treated dogs demonstrated a slower idioventricular heart rate and decreased rapid triplets (FIG. 16B). Analysis of each recording revealed a decreased average frequency of the more dangerous very rapid (≧360 bpm) ventricular triplets in the etanercept group (6±1/hr, n=8) compared to saline (21±6/hr, n=10, P<0.05) from 4-24 hours (FIG. 17A). In the saline control group, 4 animals died at 11-24 hours post ligation. As expected, these animals contributed significantly to the incidence of very rapid, malignant triplets and as each died, the incidence for the remaining animals dropped. The etanercept-treated animals also had a significantly lower average frequency of total rapid (≧300 bpm) ventricular triplets (45±8/hr, n=8) than the saline control animals (152±32/hr, n=10, P<0.05) (FIG. 17B).

Figure 18:
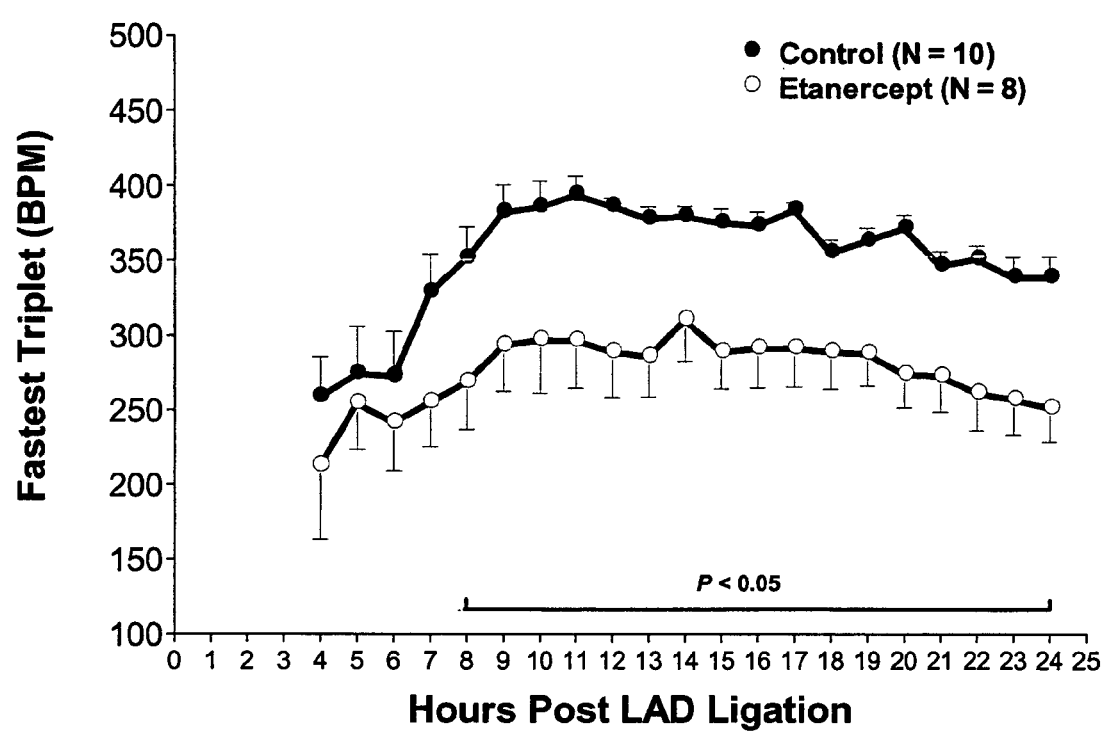
FIG. 18 illustrates the mean intrinsic rate (bpm) for the fastest ventricular triplet observed in each dog during each hour for the 4 to 24 hr period following LAD ligation in control (closed circles, n=10) and etanercept-treated (open circles, n=8) animals. The difference in the mean maximal triplet rates (mean±SEM) between the two groups was significant from hours 8-24 (P<0.05). The saline control group consistently had the faster triplets compared to the etanercept group, which would put them at greater risk for developing monomorphic ventricular tachycardia and subsequent ventricular fibrillation.
Figure 19:
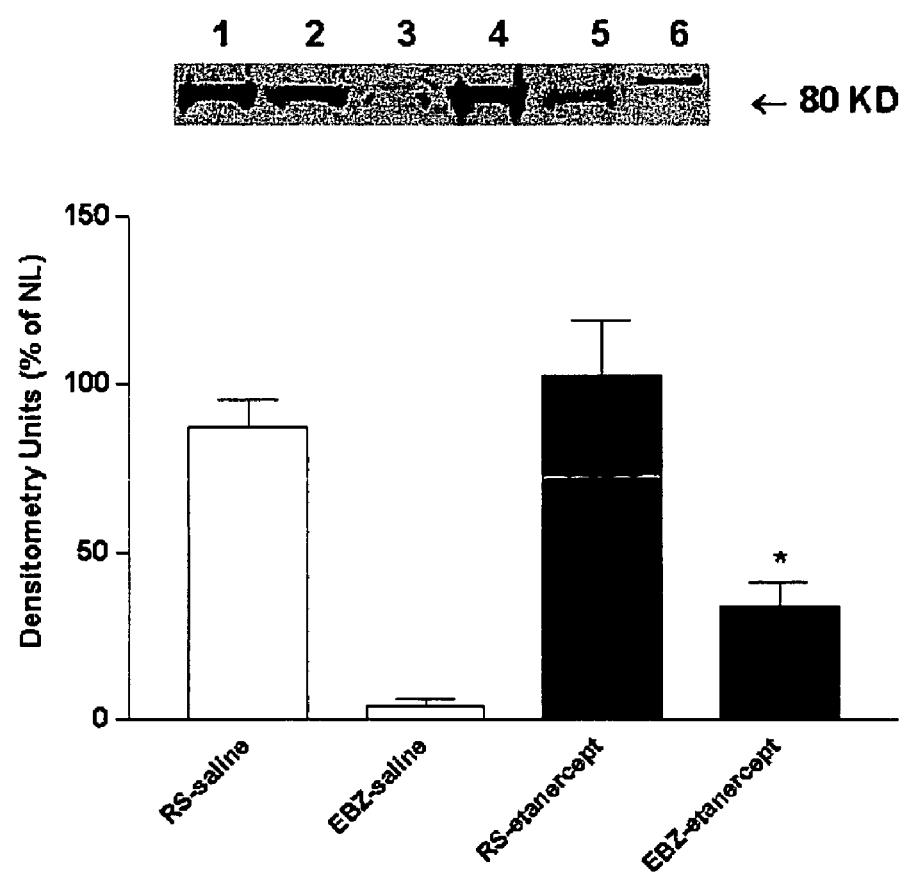
FIG. 19 contains an immunoblot of β-adrenergic receptor kinase (βARK) from unoperated control and 24-hr LAD ligated animals. Lane 1, unoperated control; lane 2, remote site (RS) of saline-treated ligated dog; lane 3; subepicardial border zone (EBZ) of saline-treated ligated dog; lane 4, RS of etanercept-treated ligated dog; lane 5, EBZ of etanercept-treated ligated dog; lane 6, purified βARK. Blots shown are representative of 5 experiments. Bar graph represents relative intensities of βARK expressed as a percentage of unoperated control (100%). Bars represent means±SEM of 5 separate experiments. *P<0.05 vs. EBZ-saline.

Malignant ventricular triplets frequently lead into ventricular fibrillation and SCD. These usually occur in this model with intrinsic rates of 300-400 bpm, and those above 360 bpm are especially dangerous (Patterson et al., 1986). A significant reduction in the fastest rate observed for such triplets in each animal per hour also was observed in the etanercept group (FIG. 18). It is of interest that the intrinsic rate for these particularly dangerous triplets in the control group rose to significance by the 8th hr after LAD ligation and remained high until the 24th-hr even after 3 animals had died. There was no significant change in the etanercept-treated animals.

βARK immunoblots were used to estimate βARK expression (Yu et al., 2000). As shown in FIG. 19, βARK was decreased in the EBZ compared with RS in both saline and etanercept groups at 24-hr. When expressed as percentage of unoperated control tissue, the EBZ in the saline group had a marked drop of βARK protein to 4.3±9.2%, while the etanercept pretreated group dropped only to 33.8±7.2% (P<0.01, n=5); thus representing an 8-fold salvage of βARK expression in EBZ tissue (FIG. 19).

Figure 20:
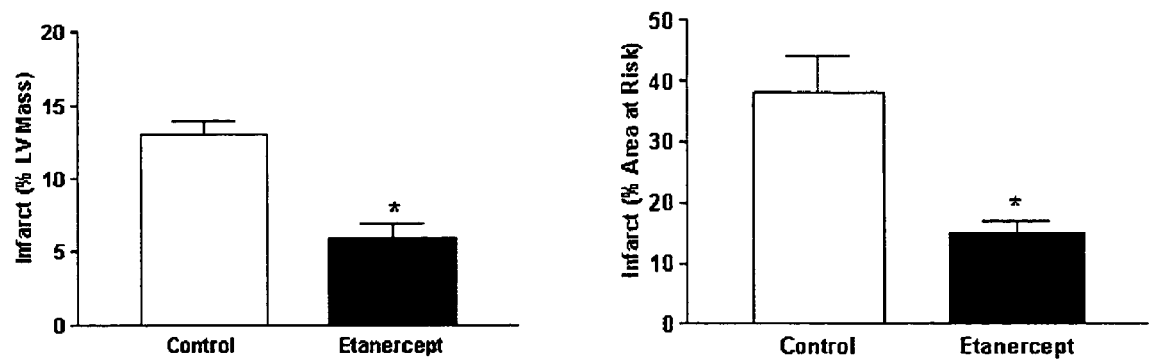
FIG. 20 illustrates infarct size of the model 2 (2-hr occlusion/4-hr reperfusion) animals pretreated with saline (n=9) or etanercept (n=8). Infarct size is expressed as % area at risk (left) or % left ventricular mass (right) (mean±SEM). *P<0.05 vs. saline control.

In the infarct size (Model 2) studies, infarct size was measured as described above and expressed both as % area at risk (AR) and as left ventricular mass (LV). In the etanercept group, infarct size was significantly decreased (15±2% AR and 6±1% LV, n=8) compared to saline (38±6% AR and 13±1% LV, n=9, P<0.05) (FIG. 20). These represent a 61% (AR) or 54% (LV) decrease respectively in infarct size in the etanercept group compared to saline.

Figure 21:
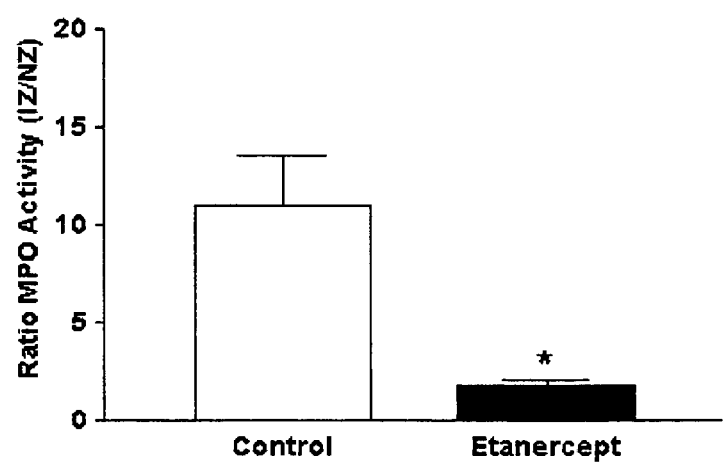
FIG. 21 illustrates leukocyte uptake in tissues from the model 2 animals pretreated with etanercept or saline. Leukocyte uptake is measured by myeloperoxidase (MPO) activity and expressed as the ratio of ischemic zone (IZ) to normal zone (NZ) (mean±SEM, n=7). P<0.01 vs. saline control.

Leukocyte infiltration, as estimated by the myeloperoxidase ratio of ischemic to normal tissue, was significantly decreased in the etanercept group (1.8±0.2) compared to the saline group (11±2.6, P<0.01, n=7) (FIG. 21). No significant difference in calculated oxygen requirement (double product) was present between control and etanercept-treatment groups (data not shown).

TNFα, a potent and ubiquitous cytokine, is released locally in response to myocardial ischemia and may mediate in part the intense inflammatory response observed in post-infarct/ischemic myocardial tissues leading to abnormal tissue function and apoptosis (Gurevitch et al., 1996; Frangogiannis et al., 1998; Irwin et al., 1999). This inflammatory response in the EBZ apparently is associated with, or concurrent to, a state of heightened adrenergic activity and/or hypersensitivity since these tissues have an increased risk for rapid ectopy (Dangman et al., 1988), rapid ventricular tachyarrhythmias and SCD (Patterson et al., 1986; Patterson et al., 1991; Patterson et al., 1991). Etanercept is a recombinant human TNF receptor conjugated to a human heavy chain IgG Fc fragment, capable of binding and inactivating both TNFα and TNFβ. This pharmacologic probe was used to examine the potential effects of TNFα sequestration on EP events in 24-hr LAD-ligated model 1 animals. This canine model incorporates an elevated sympathetic nervous system tone, features rapid ventricular ectopy triggering a spontaneous lethal event, and possesses a reentrant substrate capable of sustaining a rapid ventricular arrhythmia. This has been supported by demonstration that desensitization of β-adrenergic receptors by treatment with β-blockade (Patterson et al., 1986) or by prior left autonomic stellectomy (Patterson et al., 1991) markedly reduces the occurrence of malignant tachyarrhythmias and SCD over a 24-hr period. These outcome data demonstrate an inhibitory effect on βAR activity and SCD following acute myocardial infarction similar to those observed in human studies (Hjalmarson et al., 1981; Hjalmarson et al., 1997).

In humans, there is an association of increased ventricular premature contractions and/or runs of non-sustained ventricular tachycardia with SCD (Bigger et al., 1984; Ruberman et al., 1977). Our model 1 24-hr-ligated canine acute infarction model also demonstrates these parameters; and characteristically demonstrates a high frequency of short triplet bursts of rapid ventricular beats with an intrinsic rate >360/min which are relatively easy to quantify (Patterson et al., 1986; Patterson et al., 1991). Both the incidence and the maximum intrinsic rate of these rapid ventricular triplets, a form of non-sustained ventricular tachycardia, were reduced significantly in the animals with etanercept treatment. This significant reduction in the rate and incidence of rapid ventricular triplets was similar to changes previously observed in this model with a β-AR antagonist or prior left stellate ganglionectomy. These previous data demonstrate a major role for activation of the β-agonist/signal transduction system in this animal model of SCD. Provocative ventricular pacing at 24-hr post LAD ligation was not performed so that ventricular fibrillation would not be provoked, thereby avoiding the need for electrical defibrillation that might alter kinase expression. Therefore, a quantitative estimate of electrophysiologic changes in the reentrant substrate capable of supporting sustained tachycardia in the two groups was not made.

Rapid monomorphic sustained ventricular tachycardia (385±13 bpm) degenerating to ventricular fibrillation at 11-24 hours post ligation was observed in four saline-treated control dogs while no etanercept-treated dogs developed sustained ventricular tachycardia or fibrillation. These data project a reduced incidence of sudden death following etanercept treatment.

Changes in βARK activity are inversely reflected by β-AR sensitivity (Koch et al., 1995; Ungerer et al., 1996; Ping et al., 1997). Changes of βARK activity might be expected to produce an altered cellular electrophysiologic response to β-AR agonists, although this relationship has not been previously reported. Since ischemia is known to markedly diminish the endogenous β-AR desensitizer βARK in the heart and brain (Yu et al., 2000; Theilade et al., 2003; Lombardi et al., 2004), the impact of etanercept pretreatment on βARK expression was examined. βARK expression was markedly decreased in the saline pretreated EBZ tissues compared to RS control tissue taken from non-ischemic left ventricular tissue and also compared to sham-operated control ventricular tissues. These data confirm those published earlier using a similar animal model (Yu et al., 2000). As demonstrated in FIG. 19, pretreatment of these animals with etanercept led to significantly increased protection against loss of βARK. This salvage of βARK by etanercept treatment, although modest, was associated with important electrophysiologic consequences during the 24-hr period following LAD coronary artery ligation. Enzyme activity of greater than 10% of total activity is frequently sufficient to maintain a normal function in many systems. It is possible that the approximately 34% expression of βARK by immunoblot retains sufficient activity to partially protect against βAR hypersensitivity. The best estimate of this capacity was reported by Rockman et al. (1998), who crossbred transgenic mice to produce animals expressing 100%, 50% and 25% of control βARK activity. The βARK deficient mice had a normal lifespan and a modest increase in cardiac β-AR sensitivity to the β-agonist isoproterenol. Those with only 25% of βARK activity had a limited increase in β-adrenergic sensitivity that was disproportionately less than would be anticipated by having only 25% βARK activity. There are other possible protective explanations including alterations resulting in decreased $Ca^{2+}$ loading of the cells, from changes in $K^+$ channel function, or from decreased "inflammatory" conditions; but there are no specific data relating to each of these or to other TNFα effects comparable to its impact on the known role of βARK desensitization of catecholamine activity present in this model.

The 2-hr occlusion/4-hr reperfusion model 2 dog was chosen to study infarct development. Analysis of infarct size in this model is more reproducible since 1) the resultant acute necrosis is greater than observed at the same point with the chronic ligation model and 2) coronary LAD perfusion is largely retained, and vital tissue stains can be differentially perfused to examine several components. Using this model, etanercept pretreatment significantly reduced infarct size by approximately 50% (FIG. 20) expressed as % left ventricular mass or % area at risk. This reduction was associated with a significant decrease in MPO activity as an index of leukocyte infiltration. This supports the concept that a decrease in leukocyte attraction to the region by sequestration of the integrin-activating TNFα results in less secondary release of leukocyte-borne cytokines and diminished inflammatory destruction of tissue. There was no difference in the double product (pulse x mean arterial blood pressure) in the saline treated control animals and those pretreated with etanercept. This suggests that differences in infarct size were not related to changes in cardiac workload and oxygen requirement (Maroko et al., 1971). It is difficult to directly measure infarct size in the model 1 24hr ligation model and at the same time obtain sufficient EBZ tissue for analysis. If there were reduction in infarct size in this model, it was not associated with any observed decrease in the thickness of surviving EBZ tissue. The EBZ tissue in the model 1 dog was carefully excised and a representative strip examined by TTZ staining. Thus, if anything the ischemic tissue would either remain the same or actually increase in volume behind the LAD ligation. This might be expected to increase the frequency of the arrhythmias rather than to reduce them.

Etanercept sequestration of TNFα led to significant protection against electrophysiologic precursors of SCD and to significant reduction in infarct size in their respective dog models. The association of parallel changes in βARK expression suggests that loss of β-AR desensitization by this important protective kinase system may mediate some component of the overall increase in risk brought about by activation of the β-adrenergic system in this critical period. While there is no direct evidence to suggest that the infarct size reduction is or would be related to the observed changes in βARK, there are data to suggest that early β-blockade can reduce infarct size either directly or indirectly (Reimer et al., 1973; Miura et al., 1979; The International Collaborative Study Group, 1984). These changes following β-blockade, however, appear related to a decreased cardiac workload during β-blockade and the protective effects appear to be hemodynamic in nature (Maroko et al., 1971; Becker et al., 1971). As noted above, there were no significant differences in the estimated workload between the etanercept pretreated and saline pretreated animals. It is known that autonomic activation is an important factor inducing βARK expression in cardiac tissue (Iaccarino et al., 1998). The similar increase of βARK expression in the non-ischemic RS tissues in both models supports the notion that LAD-induced autonomic activity was similar in both models. The anti-inflammatory effect of TNFα sequestration may be sufficient in itself to reduce the area of cell apoptosis.

Etanercept has been evaluated in human clinical trials for the treatment of congestive heart failure (Anker et al., 2002). Although no significant benefits upon functional status or survival have been observed, the drug has proven to be otherwise safe for administration in patients with heart failure, many having coronary artery disease.

Effect of IL-1 Inhibition or Proteasome Inhibition on Rapid Ventricular Tachycardia (FIGS. 22-33)

The ubiquitin-dependent proteasome pathway controls gene transcription (Svejstrup, 2002; Lee, et al., 2002; Palombella et al., 1994; Rape et al., 2001; Ostendorff et al., 2002; Polakis, 2000; Aberle et al., 1997; Haupt et al, 1997; Maxwell et al., 1999) and participates to an unknown degree in β-ARK degradation (Penela et al., 1998; Li et al., 2000; Penela et al., 2001; Elorza et al., 2003; Luo et al., 2003). Therefore, the proteasome degradation pathway has been proposed as an alternative mechanism for βARK degradation (Penela et al., 1998). Direct degradation of ubiquinated βARK by the proteasome is enhanced with the stimulation of $β_2$-AR by isoproternol (Penela et al., 1998). The transcription factor, nuclear factor κB (NF-κB) is sequestered in the cytosol by the inhibitory proteins IκB-TNFα and other cytokines activate a specific IκB kinase (IKK) that phosphorylates and thereby identifies IκB for ubiquination and subsequent degradation via the proteasome (Karin et al., 2000; Pye et al., 2003). This proteasome activation of NF-κB by cytokines during myocardial ischemia could facilitate proteasome-mediated degradation of βARK in ischemically injured tissues.

One proposed mechanism by which the proteasome pathway plays an important role in the degradation of β-ARK within injured myocardium involves a direct degradation pathway for ubiquitinated proteins (such as β-ARK) via proteasomes. Direct degradation of the β-adrenergic receptor by the proteasome is enhanced with the stimulation of $β_2$-adrenergic receptors by isoproterenol (Penela et al., 1998). An increased degradation of ubiquitinated β-ARK-1 in ischemically-injured tissues by the proteasome pathway would be consistent with the increased sympathetic tone and elevated catecholamines observed during the 2-24 hr period following coronary artery ligation.

Figure 23:
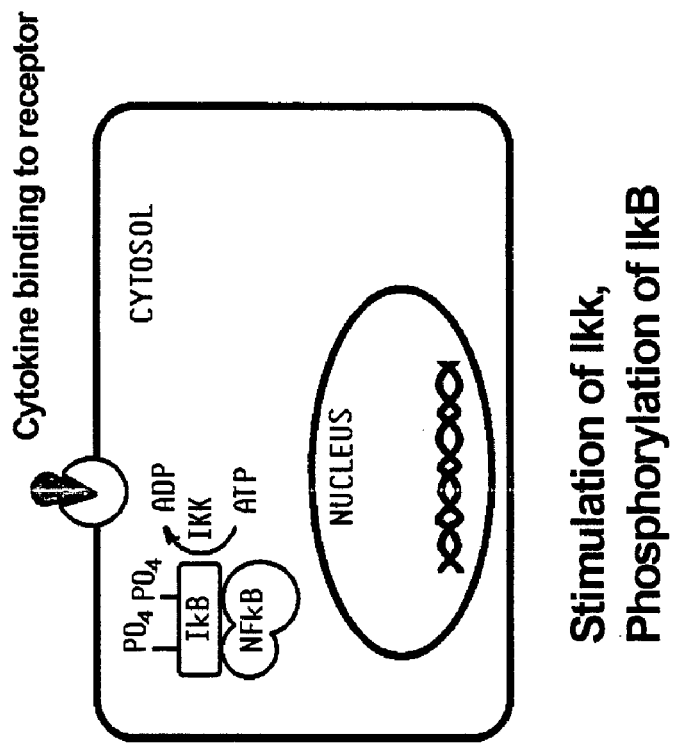
FIGS. 22-25 are graphic depictions of activation of the inducible cytosolic transcription factor, NF-κB by cytokines during myocardial ischemia and infarction. IκB serves as an inhibitory molecule while attached to NF-κB. After activation by a cytokine (TNFα, IL-1, etc.), it is phosphorylated and then subject to multiple ubiquitinylations. This activates proteasome SF26 and leads to proteasome degradation activity of ubiquitinylated proteins.
Figure 22:
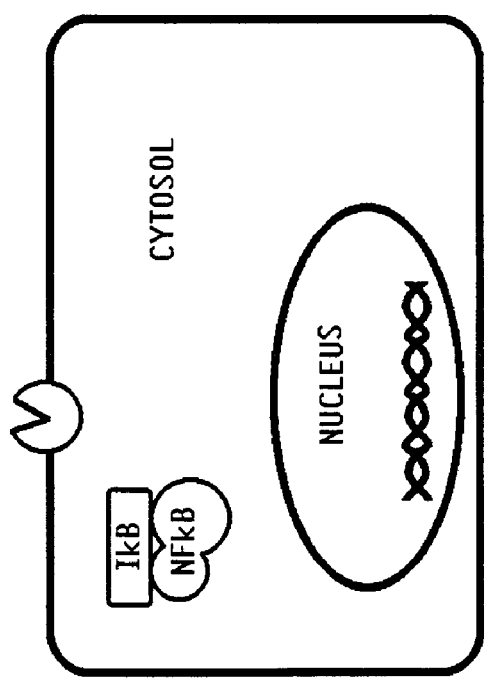
Figure 25:
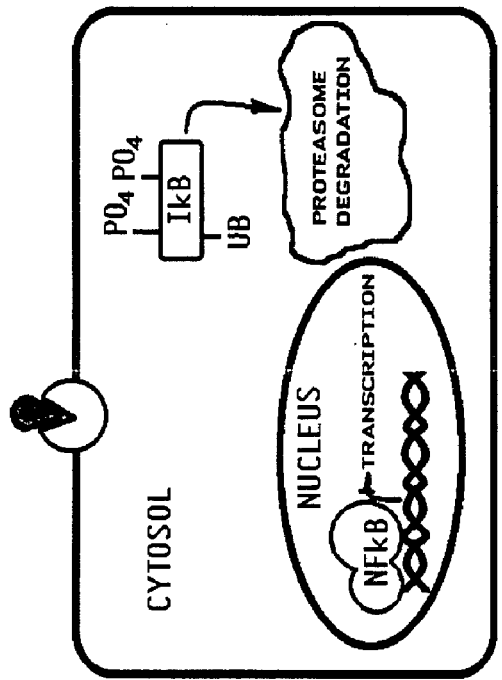
Figure 24:
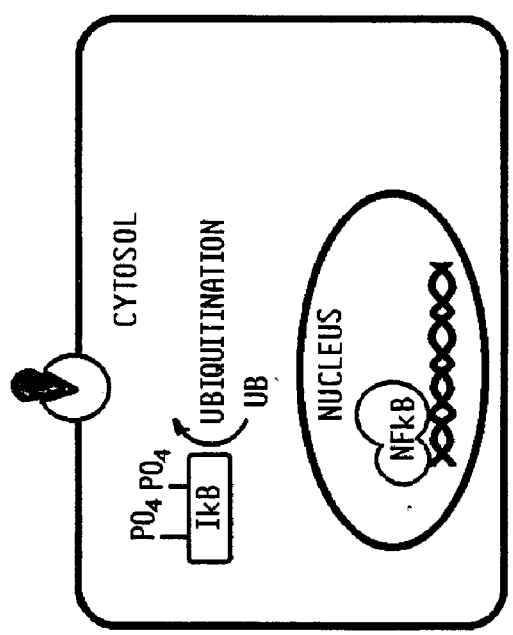

Another mechanism by which the proteasome pathway plays an important role in the degradation of β-ARK within injured myocardium involves activation of the inducible cytosolic transcription factor, NF-κB. In non-stimulated cells, NF-κB is sequestered in the cytosol by an inhibitory protein, IκB (FIG. 22). Treatment of cells with a variety of different cytokines and chemokines (nitric oxide, prostaglandins, TNF-α, interleukins, and lipopolysaccharides)(Reimer et al., 1973; Miura et al., 1979), leads to the activation of a specific IκB kinase (IKK) that phosphorylates specific serine residues of IκB, tagging it for ubiquitination and degradation via the proteasome (Reimer et al., 1973; Miura et al., 1979)(FIG. 23). Sequential phosphorylation, dissociation from NF-κB, ubiquitination (FIG. 24), and proteasome degradation of IκB allows NF-κB to translocate into the nucleus to initiate transcription of a variety of different gene products (FIG. 25). The activation of NF-κB by cytokines during myocardial ischemia and infarction would potentially facilitate the degradation of β-ARK-1 (and other proteins) in ischemically-injured tissues. Reduced proteasome inactivation of IκB (the inhibitory subunit) by a proteasome inhibitor would conversely maintain inhibition of NF-κB by IκB and reduce β-ARK-1 inactivation. This proposed mechanism is supported by the results described herein above using etanercept pre-treatment prior to coronary artery ligation in the dog.

Figure 26A:
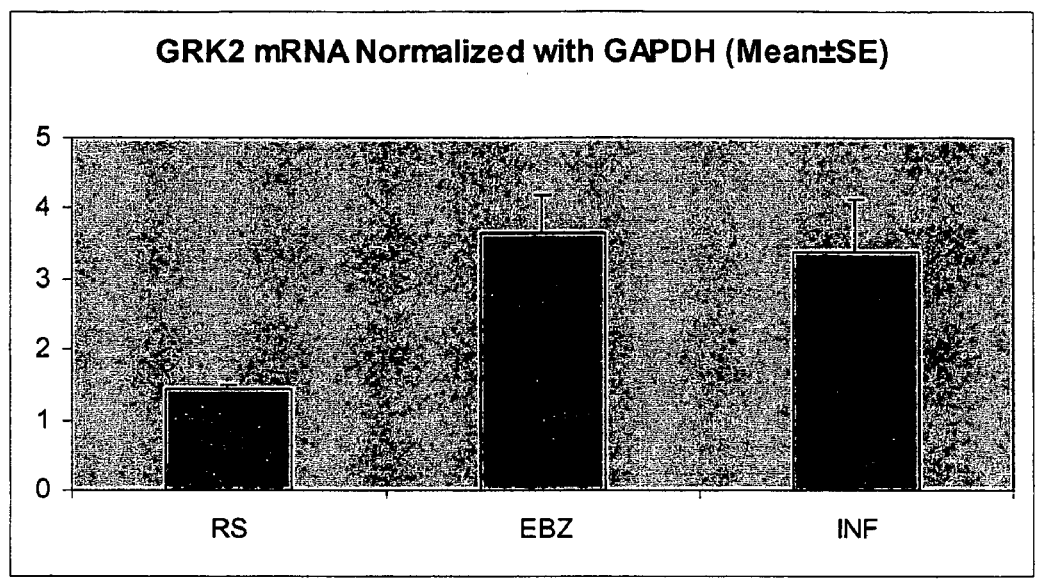
FIG. 26 illustrates data obtained from real-time RT-PCR experiments examining the effect of acute ischemia on GRK2 (β-ARK) and GRK5 transcription using 18S and GAPDH as housekeeping genes. The RT-PCR data demonstrate similar increases rather than decreases after 24 hours of ischemia in both β-ARK and GRK5 transcription in EBZ and in infarct tissue compared with RS tissue.
Figure 26B:
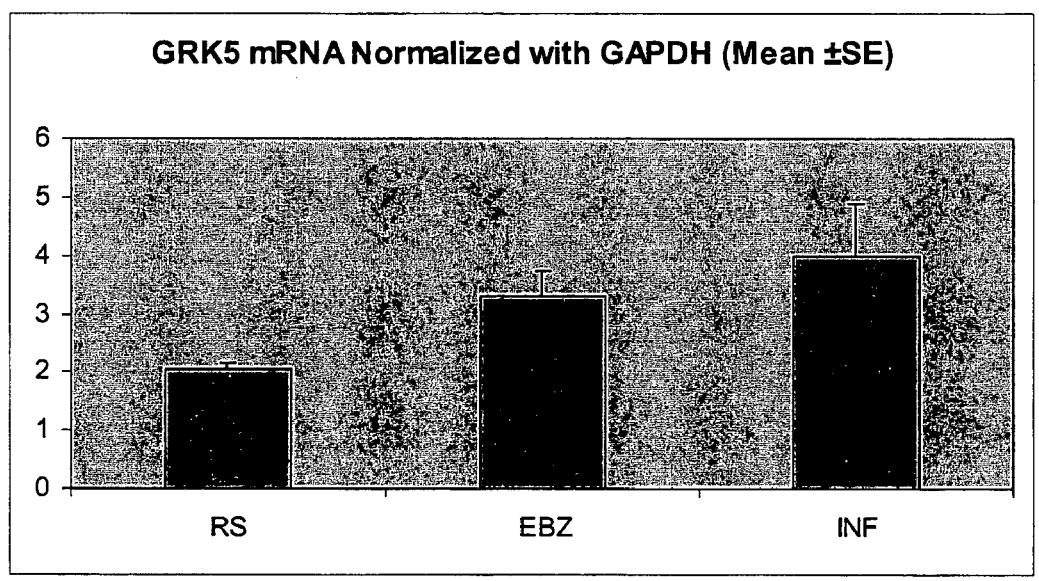

Real-time RT-PCR has been used herein to examine the effect of acute ischemia on β-ARK and GRK5 transcription using 18S and GAPDH as housekeeping genes. Preliminary RT-PCR data demonstrated similar increases rather than decreases after 24 hours of ischemia in both β-ARK and GRK5 transcription in EBZ and in infarct tissue compared with RS tissue (FIG. 26). The results were consistent and demonstrated similar changes in β-ARK and GRK5 transcription. This increase and similarity in effects on both β-ARK and GRK5 transcription do not reflect the observed changes of β-ARK and GRK5 expression. Although there is a marked decrease in β-ARK expression by 6 hours lasting up to 96 hours, there is an increase in GRK5. Although there could be increased nuclear "runoff" of the β-ARK1 mRNA to account for the decrease after ligation and ischemia, there are no data to date that β-ARK and GRK5 have markedly differing transcriptional runoff patterns (Pitcher et al., 1998; Krupnick et al., 1998; Bunemann et al., 1999), the changes in β-ARK and GRK5 mRNA are parallel, and yet protein expression is markedly different.

Figure 27:
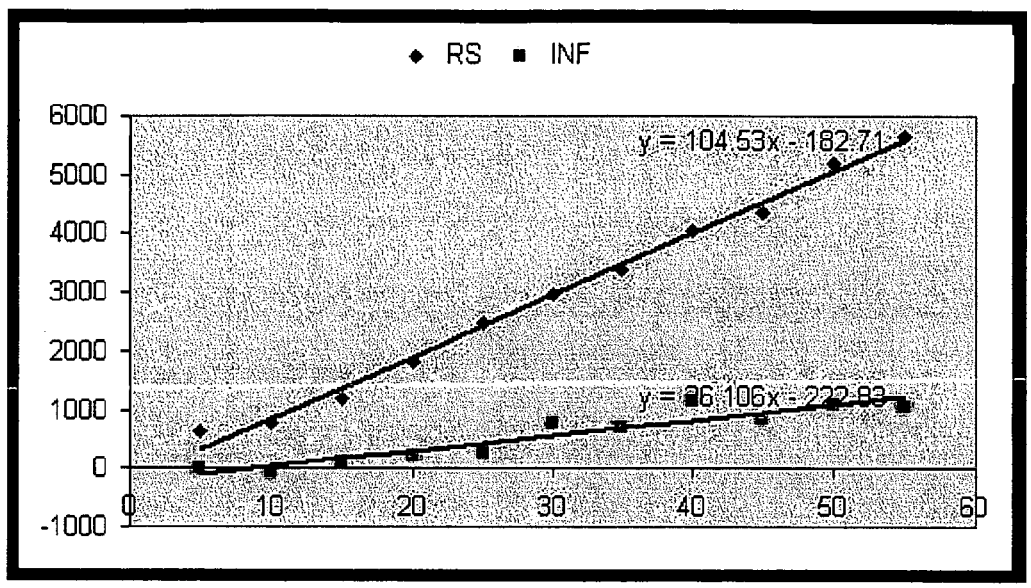
FIG. 27 illustrates proteasome chymotrypsin-like peptidase activity in myocardial RS and INF tissues from a 6-hr infarcted dog. The slope is an estimate of the proteasome activity. Equal concentrations of protein (150 ug) were assayed, so the infarct tissue has 25% of RS tissue proteasome activity.
Figure 28:
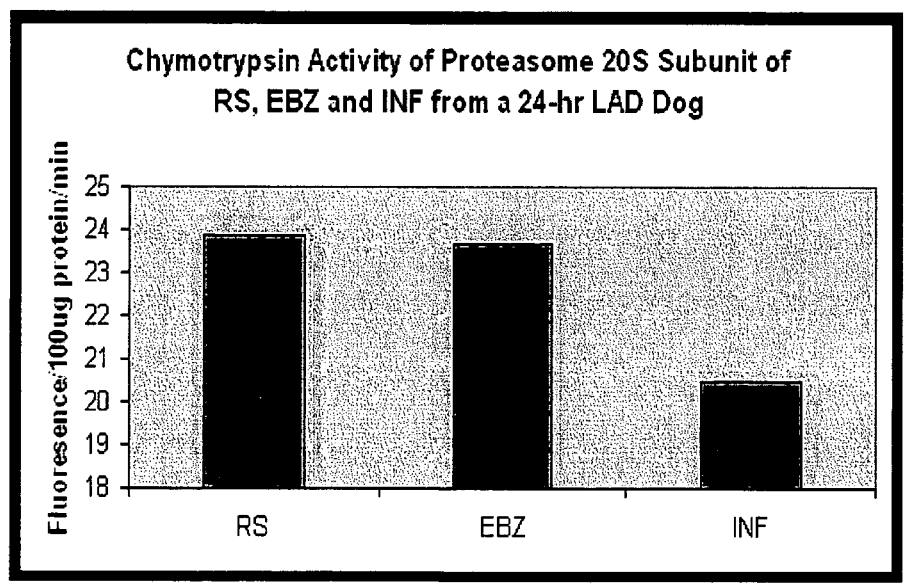
FIG. 28 illustrates proteasome activity measured in remote site (RS), subepicardial border zone (EBZ) and infarct tissue (INF) 24-hr after LAD ligation in a single dog.
Figure 29:
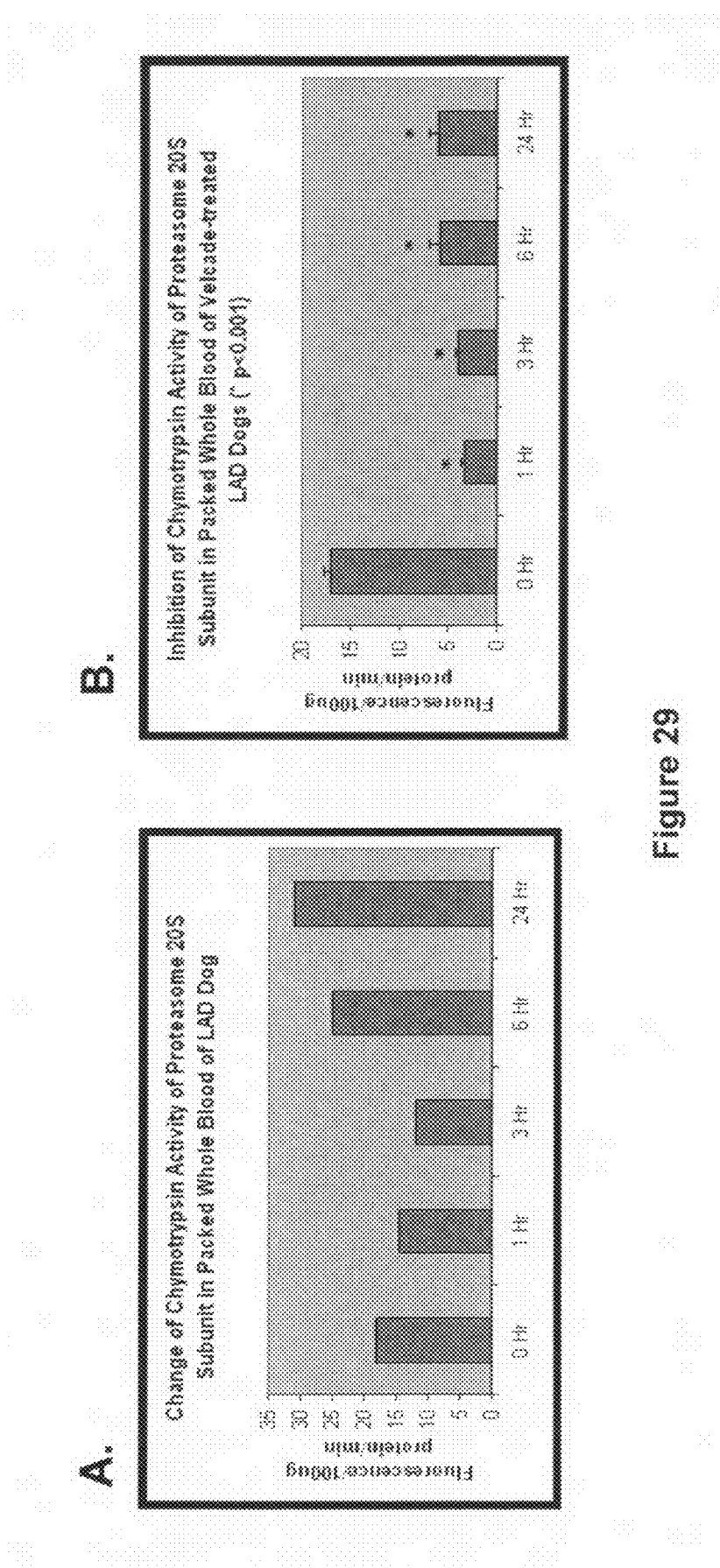
FIG. 29A (left panel) shows the effect of anesthesia and ischemia on packed whole blood proteasome activity in a single dog treated with a saline (control) injection 1-hr before and 8 hr after LAD ligation. O time is the time of the first injection, and each hr represents the time after injection. 1-hr is the time of ligation. There is a drop in activity from the time of injection to 3-hr and then a steady rise till 24-hr after injection and 23-hr after LAD ligation.
FIG. 29B (right panel) shows the packed whole blood proteasome activity (mean +/− SEM) for 4 dogs similarly injected with PS341 (VELCADE™) (0.175 mg/kg) at the same intervals as in 29A. There was a significant decrease in proteasome activity 1-hr after the first injection and this remained low for the full 24-hr after injection. (*<P 0.01, n=4)

Proteasome activity has been measured using a non-isotopic fluorescence assay (see below for details) in EBZ, RS and infarct tissues taken 6-hr after LAD occlusion. These preliminary data obtained at 6-hr from a single LAD-ligated dog suggested a decrease in infarct proteasome activity (FIG. 27). Proteasome activity was then measured after 24-hr ligation, which again demonstrated a decrease in proteasome activity in the infarct tissue, but no apparent significant difference between the remote site and EBZ tissue (FIG. 28).

PS-341 is a dipeptide boronic acid that selectively inhibits proteasome activity by interacting with a threonine residue located in its catalytic center. It was used as described herein after to determine the relative importance of the proteasome pathway for GRK degradation and to determine if it alters β-ARK and GRK5 transcription.

Figure 30:
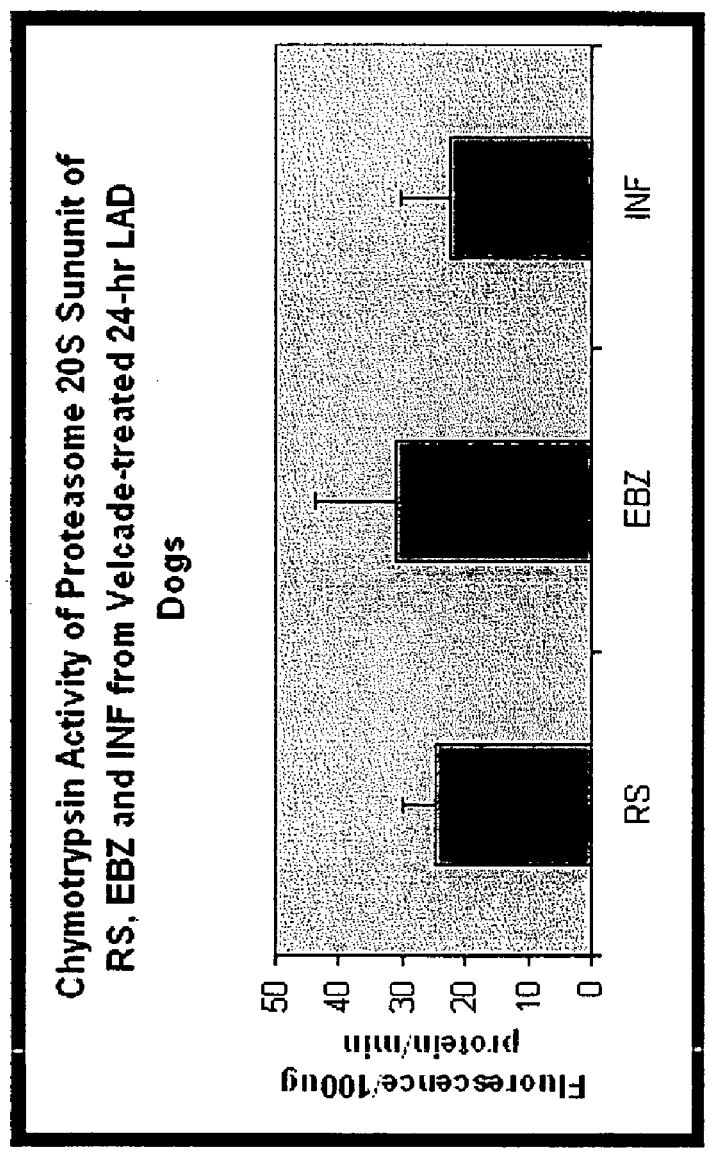
FIG. 30 shows the myocardial tissue's proteasome activity (mean +/− SEM) for the same four dogs injected with PS341 (VECLADE™) (0.175 mg/kg) shown in FIG. 29B. Myocardial samples were obtained 24-hr after the first PS-341 injection and 23-hr after LAD ligation. There was no significant change in proteasome activity between the 3 different tissues. These levels are decreased from control tissues obtained from three other dogs prior to LAD, which averaged 45 FU/100 μg protein/min. There is strong evidence that tissue compartmentalization is present and the myocardial effects of the PS-341 are not proportional to the suppression of proteasome activity observed in packed whole blood cells.

In order to determine if PS341 would suppress tissue proteasome activity, preliminary data has been obtained at 1, 3, 6 and 24-hr after injection of PS-341 (bortezomib, VEL-CADE™) (corresponding times of 0, 2, 5 and 23-hr after LAD ligation) in one saline treated control dog and 4 PS-341-pretreated animals. Whole blood was measured at each time interval (FIGS. 29A and 29B), and ischemic myocardial tissue proteasome activity was measured at the final time interval (FIG. 30).

These data demonstrate that control-animal proteasome activity assays are somewhat difficult for interpretation of the drug pretreated groups. Tissue compartmentalization of PS341 may occur, and measurement of overall proteasome suppression may vary according to the tissue examined. Proteasome activity, even modestly reduced, may not be the rate-limiting step. However, more profound suppression appears to be present in the whole blood tissue, and thus appears to be proportional to the PS341 effects present in the myocardium.

An assay has also been developed herein to estimate β-ARK ubiquination. After identification of the GRK by immunoblot, the gel is stripped, and a validated anti-ubiquitin Ab (Santa Cruz, Inc) is used to stain the proteins. The gel is then scanned to obtain a semiquantitative estimate of β-ARK ubiquination. Using the anti-ubiquitin Ab, a 4-fold increase in general density of the gel in the infarcted tissue has been demonstrated compared to the RS tissue 6-hr after LAD ligation.

To determine the effect of a proteasome inhibitor or a cytokine inhibitor on the development of lethal ventricular tachyarrhythmias and loss of β-ARK expression, (1) 0.0875 mg/kg bortezomib, a proteasome inhibitor, was administered one hour prior and six hours following LAD coronary artery ligation; (2) 10 mg/kg anakinra, an IL-1 inhibitor, was administered one hour prior and 12 hours following LAD coronary artery ligation; or (3) 2 mg/kg etanercept was administered 24 hours and 1 hour prior to LAD coronary artery ligation. These experiments compared the role of proteasome, IL-1 and TNF inhibition on lethal ventricular tachyarrhythmias and myocardial necrosis.

Figure 31B:
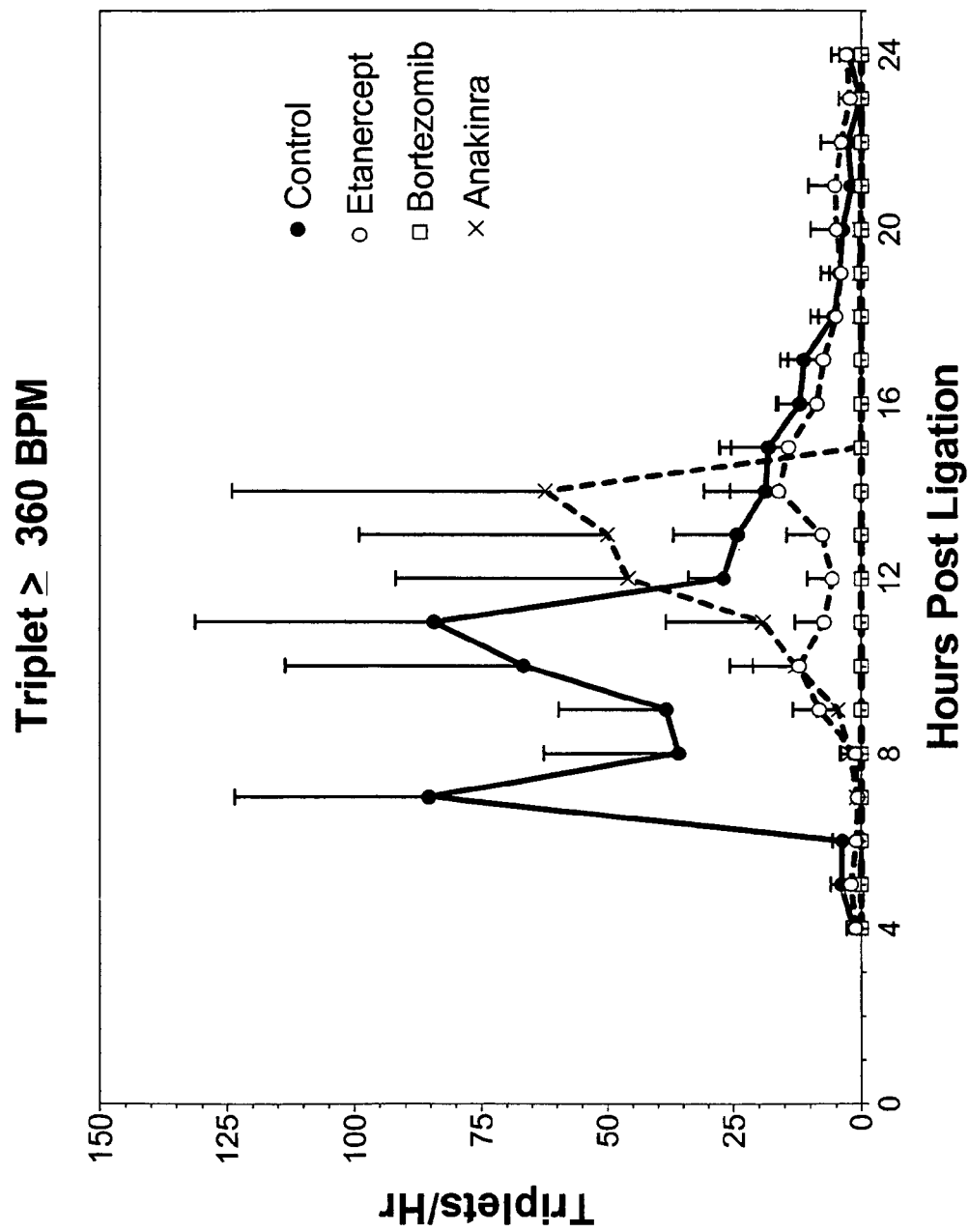
FIG. 31B illustrates all of the very rapid triplets (all ≧360 bpm) for the four groups.

There was a significant descrease in both rapid (>300 bpm; FIG. 31A) and very rapid (>360 bpm; FIG. 31B) in the etanercept and bortezomib treated animals. The difference is especially striking in the bortezomib group.

The control and etanercept groups had equivalent numbers of very rapid triplets after the three dogs at greatest risk had died. The number of rapid triplets in the anakinra group were relatively low until 8 hours after LAD and then rose rapidly despite a second injection at 12 hours (FIG. 31A). The bortezomib group had a marked suppression of rapid triplets, and no (0) rapid (>300 beats/min) were observed.

The saline control animals generally had a significantly greater number of total very rapid triplets (≧360 bpm) throughout the time period (FIG. 31B). The etanercept group had a significant decrease in very rapid triplets, which represent the arrhythmia most likely to degenerate into sustained ventricular tachycardia and subsequent ventricular fibrillation. The bortezomib group again had no triplets in this range, supportive of the marked suppression seen with proteasome inhibition.

Figure 32:
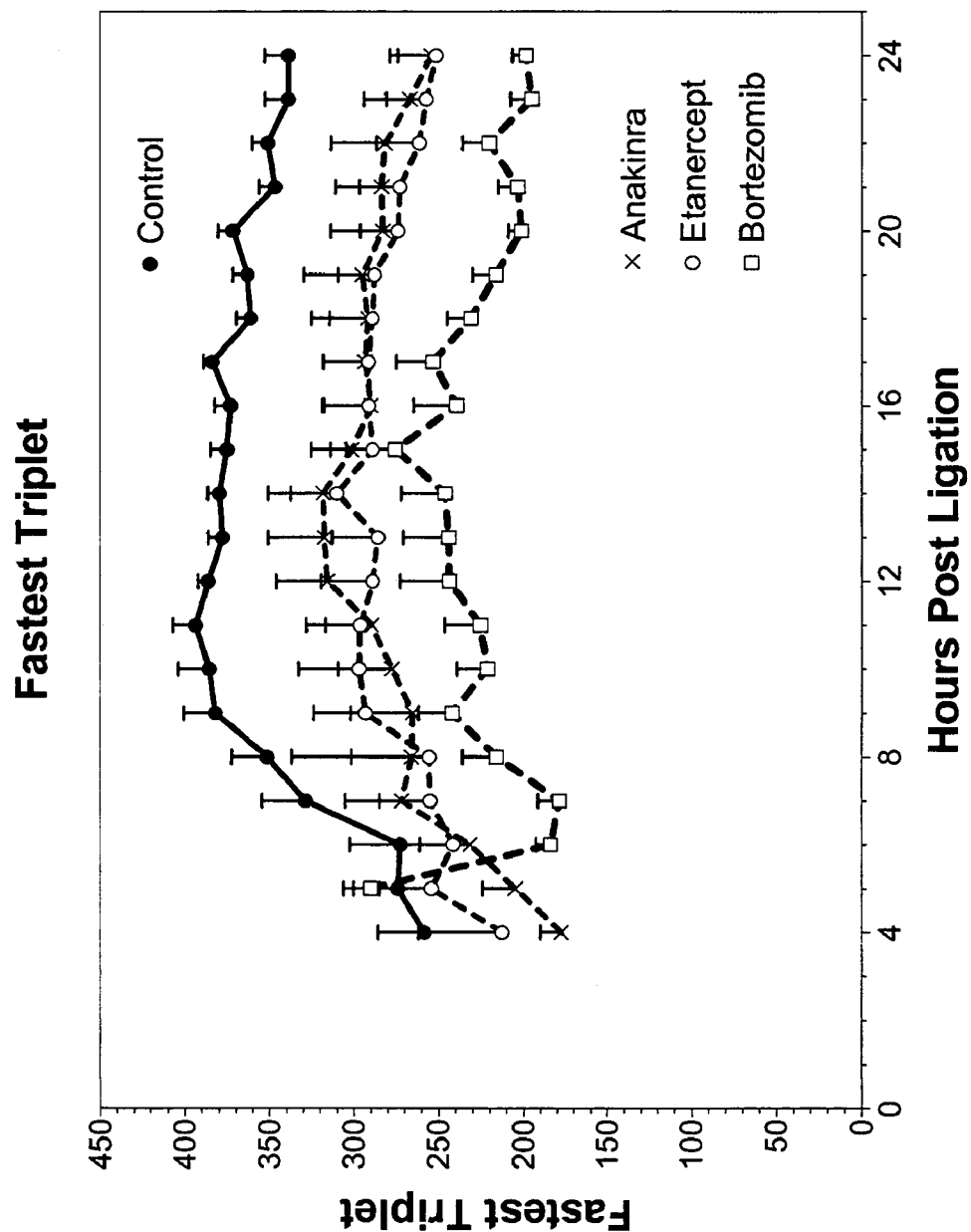
FIG. 32 illustrates the mean ±SEM for the fastest ventricular triplets observed per hour after LAD in the control and treatment groups of FIG. 31. The mean intrinsic rate (bpm) for the fastest ventricular triplet observed in each dog during each hour for the 4 to 24 hour period following LAD ligation in control, anakinra, etanercept, and bortezomib treated animals.

FIG. 32 illustrates the fastest ventricular triplets observed per hour after LAD. The difference in the mean maximal triplet rates (mean±SEM) between the control and etanercept groups was significant from hours 8-24 (P<0.05). The saline control group consistently had the faster triplets compared to the etancercept group, which would put them at greater risk for developing monomorphic ventricular tachycardia and subsequent ventricular fibrillation. There was no significant difference between etancercept and anakinra, but there was a marked decrease in bortezomib compared to all other groups.

Figure 33:
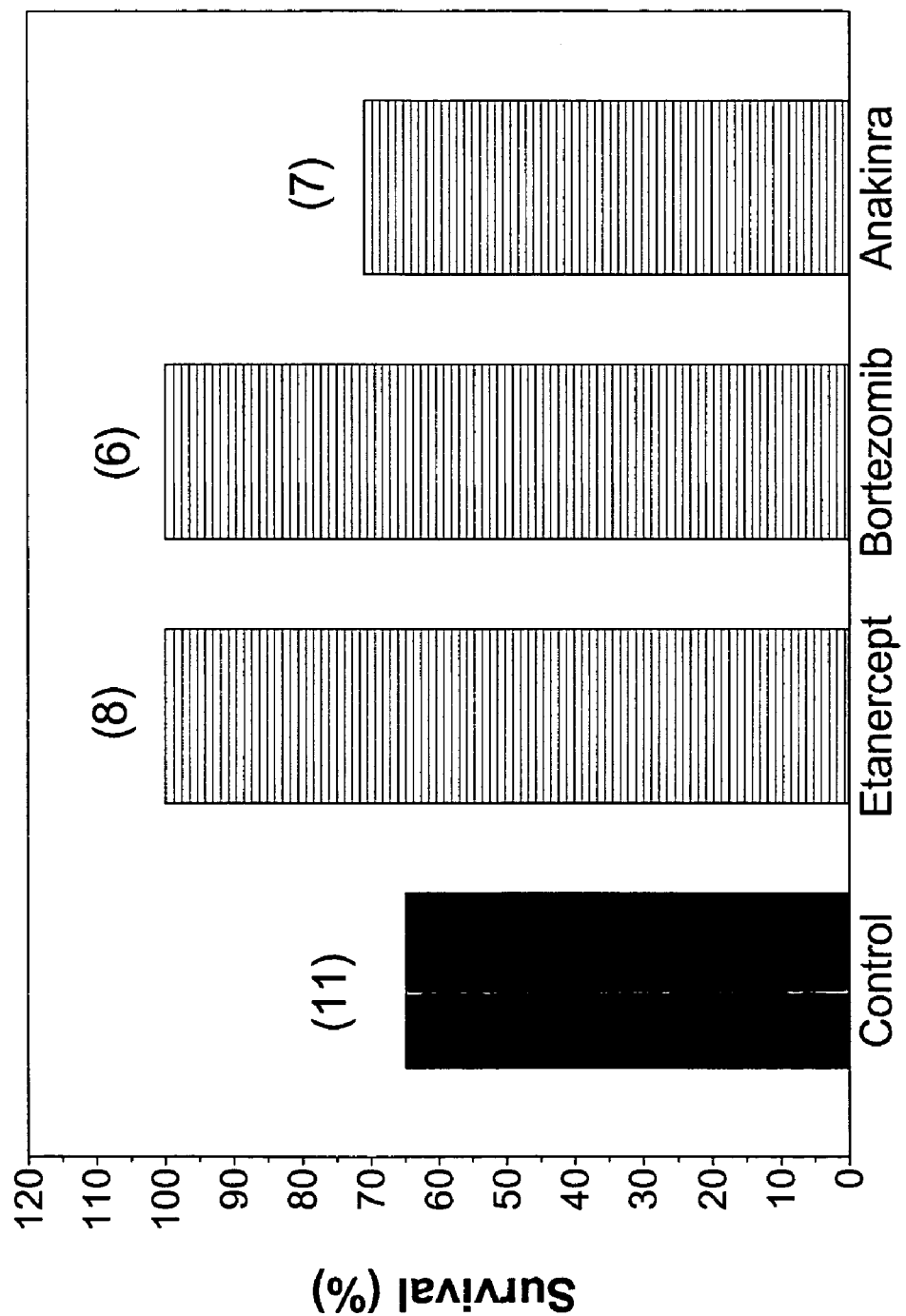
FIG. 33 illustrates preliminary mortality data for the control and treatment groups of FIG. 31.

None of the animals pretreated with etanercept or bortezomib have died compared to control and Anakinra (FIG. 33). A total of 4 of 10 control dogs died from the development of monomorphic sustained ventricular tachycardia and resultant ventricular fibrillation, and one dog died in the Anakinra group (1 of 7). No dogs have died in the etancercept (0 of 8) and bortezomib (0 of 6) groups.

Figure 34:
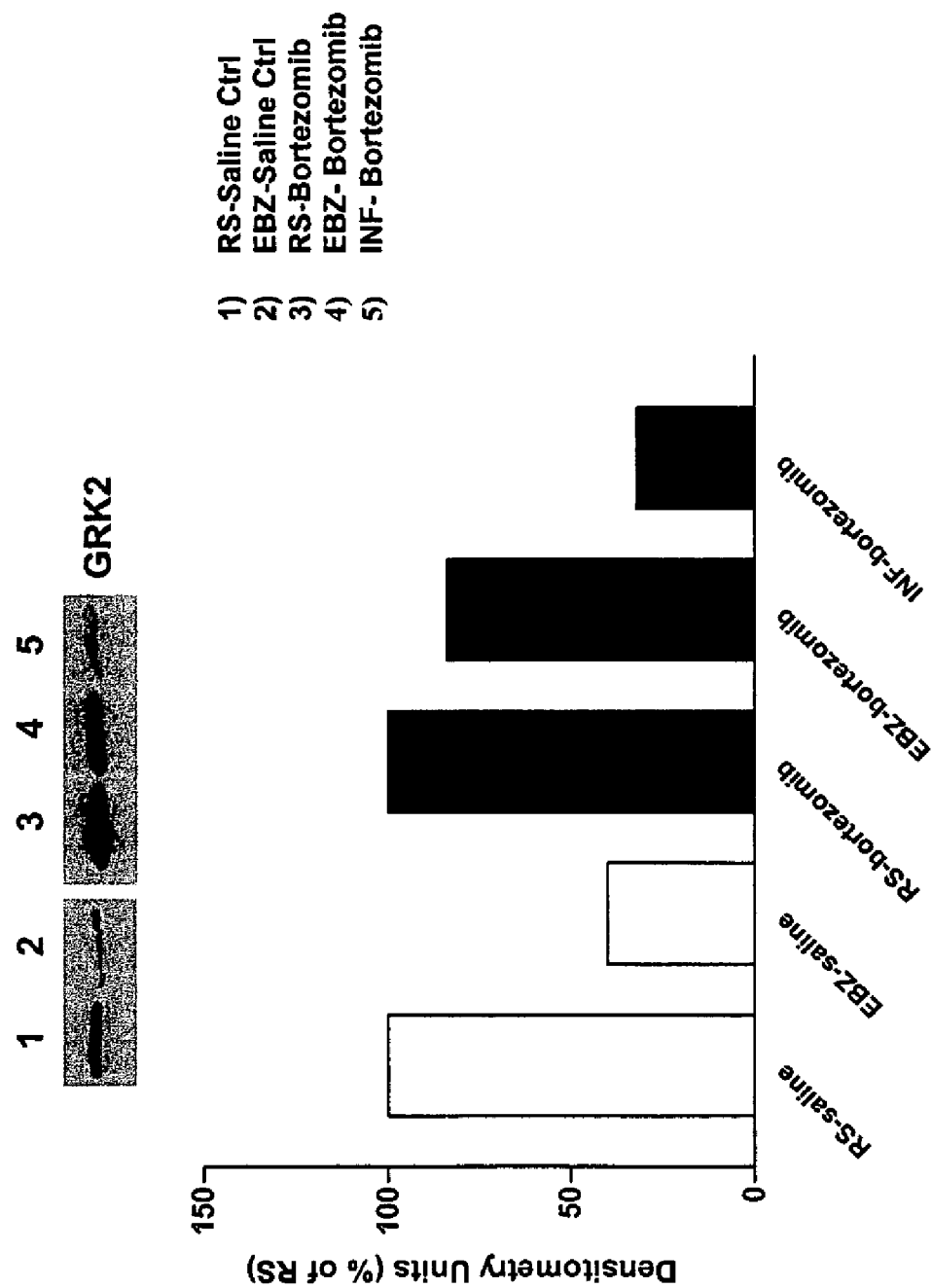
FIG. 34 is a representative Western immunoblot of βARK levels in a control dog and a bortezomib pretreated dog after LAD. There was significant protection against loss of GRK2 expression in the bortezomib treated animal compared to its saline control.

FIG. 34 illustrates that bortezomib also prevents loss of β-ARK in NS and EBZ tissues. There was the expected loss of EBZ βARK in the saline pretreated 24-hour infarcted dog compared to its RS (LCX) non-ischemic tissue (100% densitometry units). A marked protection against loss of βARK protein was observed in the bortezomib pretreated animal.

Thus, the experiments presented herein have demonstrated the prevention of sustained monomorphic ventricular tachycardia via cytokine inhibition or proteasome inhibition that results in protection against substantial loss of β-ARK expression and/or activity.

Materials and Methods

Ischemic Dog Models: All animal studies were performed following protocol approval by the VAMC and OUHSC Institutional Animal Care and Use Committees. The numbers of animals were approved for each group subject to achievement of a significant difference from control with a P<0.05. Only mongrel male dogs without evidence for heart worms or other identifiable diseases were used to avoid the confounding effects of a variable increase in collateral coronary artery flow that can be associated with possible prior pregnancy or systemic illness. Two different canine ischemic myocardium models were chosen; one for each experiment with attention to the specific parameters to be measured.

Model 1: Electrophysiologic correlates of myocardial infarction over a 24-hr period. Eighteen 15-22 kg male mongrel dogs were anesthetized with IV sodium pentobarbital (30 mg/kg). A cuffed endotracheal tube was inserted and the animals were ventilated with room air using a volume-cycled respirator. Each dog had a two-step ligation of the LAD, at the level of the tip of the left atrial appendage, to decrease early (1-2 hr) ventricular fibrillation. The dogs were extubated and allowed to awaken in a temperature-controlled, humidified small animal post-operative recovery unit. They were given nalbuphine 0.2 mg/kg for post-operative analgesia. During the 2-24 hr period following LAD ligation, Holter monitoring was performed and the two-lead EKG was recorded on magnetic tape. Dogs were re-anesthetized with sodium pentobarbital at 24-hr. The thoracotomy was reopened and the heart was removed and perfused with ice-cold Tyrode's buffer via the left main coronary artery. The outer 0.5-1.5 mm EBZ tissue overlying the infarct was shaved and a longitudinal sample of tissue from the LAD region was stained with triphenyltetrazolium chloride (0.1%) to determine viability of the EBZ. Triphenyltetrazolium (TTZ) forms a brick-red precipitate in the presence of active intracellular dehydrogenases, delineating vital tissue. Non-viable tissues are not stained and remain a pale color. Remote site (RS) control tissue was obtained from a superior portion of the lateral left ventricle perfused by the left circumflex coronary artery. Tissue samples from the RS, the EBZ and the infarct tissue were dissected rapidly on an ice-cold surface, placed in freezer vials, and frozen in liquid nitrogen. These samples were then stored at −70° C. for later assay. This model was chosen since studies have demonstrated that SCD predictably occurs in 25-33% of these animals during the 6-24-hr interval following LAD ligation in this canine model of myocardial infarction (Patterson et al., 1991).

EKG Analysis: Full disclosure EKG records were obtained at 10 mm/sec for the entire 2-24 hour post-occlusion period. All measurements and calculations were made by direct visual observation and manual counting.

Model 2: Acute changes in infarct size. Seventeen 15-22 kg male mongrel dogs were anesthetized and respired as described above. Body temperature was maintained using a temperature-controlled operative table bed and fluid replacement. Two EKG leads (L-II and V-3) and arterial pressure (left femoral) were continuously monitored during the experiment. Each had a 2-hr duration occlusion of the LAD coronary artery and the LAD ligation was then released. After 4 hours of reperfusion, the heart was removed and rinsed with room-temperature Tyrode's solution. Cannulae were placed into the proximal aorta and into the LAD artery at the site of occlusion for perfusion with Evans blue (0.1%) and TTZ (0.1%), respectively, at equal pressure (80 mmHg).

The area at risk of infarction was delineated by its red color (surviving myocardium) or a pale color (infarct) with the remaining heart stained by Evan's blue. The heart was then sliced to provide a 5 mm thick section parallel to the AV groove. After storage overnight in buffered formalin, infarcted tissue, surviving myocardium within the anatomic area at risk of infarction, and left ventricle outside the area at risk of infarction were separated using a scalpel blade. Infarct mass, area at risk of infarction, left ventricular mass, and total heart mass were determined gravimetrically.

Normal Control Dog Model: Cardiac tissues were obtained from 3 unstressed control dogs. These hearts were removed within 10 minutes of pentobarbital anesthesia to minimize stress-induced release of catecholamines.

Anti-TNFα Treatment: A dosage of 2 mg/kg hTNFR:Fc (supplied as etanercept, Amgen, Inc, Thousand Oaks, Calif.) or saline were injected IV into a forepaw vein at 24-hr and again 1-hr prior to LAD ligation. No side effects of this injection were observed in any dog. This dosage was used after consultation with the pharmaceutical corporate pharmacology section and based on unpublished internal data that this dosage would provide maximal sequestration of tissue and circulating TNFα.

Western Blot Analysis: Assessment of βARK content was conducted using standard SDS-PAGE and immunoblot techniques. Samples containing 100 µg of protein from myocardial extracts were electrophoresed using 10% SDS-PAGE and transferred to nitrocellulose membranes. The membrane was incubated with monoclonal anti-βARK (Upstate Biotechnology, Inc, Lake Placid, N.Y.), followed by exposure to peroxidase-linked anti-mouse IgG. Antibody binding was detected by a chemiluminescent method (ECL, Amersham Biosciences Corp, Piscataway, N.J.). Quantification of immunoreactive proteins was performed by densitometric scanning and with Image QuaNT software (Molecular Dynamics).

Calculated Oxygen Requirement and Leukocyte Infiltration: The animal's oxygen requirement was estimated by calculation of the double product (heart rate x mean arterial pressure). The myocardial activity of myeloperoxidase (MPO), an enzyme occurring virtually exclusively in neutrophils, was determined by using a modification of the method of Bradley (Mullane et al., 1985). Change in absorbance was measured spectrophotometrically in the supernatants of homogenized myocardium. One unit of MPO is defined as the quantity of enzyme hydrolyzing 1 mmol of peroxide per minute at 25° C.

Statistical Analysis: Data are expressed as the mean±SEM. Differences between normally distributed groups were determined with a 2-tailed Student's t test. Studies involving multiple comparisons were analyzed using a one-way ANOVA followed by a Bonferroni post-test. Non-normally distributed EKG data were analyzed at individual time points using the Mann-Whitney non-parametric test. Significance was ascribed to P values <0.05.

β-ARK, Proteasome and Ubiquitin Expression Assays: β-ARK, ubiquitinated β-ARK and proteasome in EBZ and RS tissues was determined by Western blot analysis. Samples were adjusted after protein concentration was assayed (BCA, Pierce Chemicals) to provide identical loads. 100 µg protein was combined with equal volume of SDS sample buffer, and electrophoresed on a 10% polyacrylamide gel. The blocked membranes were incubated with mouse anti β-ARK monoclonal antibody (Santa Cruz Biotechnology, Santa Cruz, Calif.) for 1-h at room temperature followed by anti-mouse IgG coupled to horseradish peroxidase and developed using an ECL western blotting kit (Amersham). The bands were scanned, stripped and reprobed with mouse anti-ubiquitin antibody (Santa Cruz Biotechnology, Santa Cruz, Calif.). The membrane was rescanned, stripped a second time and reprobed with rabbit anti-proteasome 20S C2 subunit polyclonal antibody (A.G. Scientific, Inc. CA). A separate control gel was included that was similarly treated, but reprobed with the identical Ab and band quality and density compared to the previous data obtained before stripping. Quantitation of immunoreactive bands was performed by densitometric scanning using ImageQuant software (Molecular Dynamics).

Proteasome activity: Activity was determined by proteasome chymotrypsin-like peptidase activity assay. Both cardiac (all groups) and whole blood cell (groups 4 and 5) proteasome activity was assayed. 30 mg frozen cardiac tissue was powdered in liquid nitrogen and sonicated in 0.5 ml buffer. Samples were then centrifuged for 30 min at 10,000 g at 4° C. and the supernatant was used for the assay. For preparing whole blood cell, heparinized blood was washed one time with saline and twice with cold PBS. The cells were lysed with EDTA (5 mM, pH 8.0) for 1 hr and centrifuged at 6600 g for 10 min at 4° C. and the supernatant was used for the assay. 0.4 mM Suc-Ala-Ala-Phe-MAC (Bachem California) was used as substrate. The assay was run with and without MG-231 (Calbiochem; 10 µM) to specifically inhibit proteasome activity. The time course for fluorescence was measured using a VICTOR3 Multilabel Counter (Perkin Elmer, Inc) at time 0 and every 5 min for 1 h to estimate the MAC liberated (excitation 380 nm, emission 460 nm). Slopes and intercepts were calculated using Microsoft Excel. Final results were expressed as fluorescence units/µg protein/min.

β-ARK and GRK5 mRNA transcription: β-ARK levels were determined using real-time quantitative RT-PCR. Total RNA was extracted from 30 mg frozen tissue using QIAGEN's (Valencia, Calif.) RNeasy® Fibrous Tissue Mini kit. The concentration of RNA was determined by spectrometer. cDNAs were created using an Invitrogen (Carlsbad, Calif.) Superscript™ First-Strand Synthesis System with 1 µg of. Real-time PCR amplification mixtures (15 µl) contained 50 ng template cDNA (2 µl), 2× SYBR Green Master Mix (7.5 µl) (Applied Biosystems) and 1 µM forward and reverse primer. Reactions were run on an ABI PRISM 7700 Sequence Detector (Applied Biosystems, Foster City, Calif.). Optimal cycling conditions for these assays comprise 10 min polymerase activation at 95° C. and 40 cycles at 95° C. for 15 sec and 60° C. for 60 sec, 95° C. for 15 sec, 60° C. for 20 sec, 95° C. for 15 sec with ramp time of 20 min. Each gene assay included triplicates of the cDNA reaction, a no-template control reaction and a RNA control reaction. Three controls were used, including two accepted ischemia-relevant housekeeping genes 18S and GAPDH, and GRK5 whose protein expression, contrary to β-ARK, does not decrease with the ischemia at 24 hours. The primer sequences for β-ARK, GRK5, 18S and GAPDH are in Table II. The sizes of these PCR products approximate 100 bp.

TABLE II

Primers used for detection of β-ARK, GRK5, 18S and GADPDH

| Primer | Nucleotide sequence | |
|---|---|---|
| 18S (internal control) | | |
| Forward | 5'TTCGGAACTGAGGCCATGAT3' | (SEQ ID NO:1) |
| Reverse | 5'TTTCGCTCTGGTCCGTCTTG3' | (SEQ ID NO:2) |

TABLE II-continued

Primers used for detection of β-ARK, GRK5, 18S and GADPDH

| Primer | Nucleotide sequence | |
|---|---|---|
| GAPDH (internal control) | | |
| Forward | 5'CAGTGACACCCACTCTTCCA3' | (SEQ ID NO:3) |
| Reverse | 5'CCGGTTGCTGTAGCCAAATT3' | (SEQ ID NO:4) |
| β-ARK | | |
| Forward | 5'ACCAGGAACTCTACCGCAACTTT3' | (SEQ ID NO:5) |
| Reverse | 5'TTTTCTTGCGGGCCTCCATT3' | (SEQ ID NO:6) |
| GRK5 (homolog control) | | |
| Forward | 5'GGATGTTGGACCCTCCCTTCATT3' | (SEQ ID NO:7) |
| Reverse | 5'ACGCCTTTCACGGTGGAGAA3' | (SEQ ID NO:8) |

Real time RT/PCR data was analyzed using Microsoft Excel software. The data was normalized with each internal control and then expressed as percentage change relative to the RS values.

Thus, in accordance with the present invention, there has been provided a method of the prevention and/or termination of malignant ventricular tachyarrhythmia, particularly ventricular fibrillation due to an increased number of ventricular triplets using a composition that inhibits substantial loss of β-ARK activity and/or expression that fully satisfies the objectives and advantages set forth herein above. Although the invention has been described in conjunction with the specific drawings, experimentation, results and language set forth herein above, it is evident that many alternatives, modifications, and variations will be apparent to those skilled in the art. Accordingly, it is intended to embrace all such alternatives, modifications and variations that fall within the spirit and broad scope of the invention.

REFERENCES

The following references, to the extent that they provide exemplary procedural or other details supplementary to those set forth herein, are specifically incorporated herein by reference in their entirety as though set forth herein particular.

1. Aberle H, Bauer A, Stappert J, Kispert A, Kemler R. β-catenin is a target for the ubiquitin-proteasome pathway. EMBO J 1997;16:3797-3804.
2. Adams J, Palombella V J, Sausville E A, Johnson J, Destree A, Lazarus D D, Maas J, Pien C S, Prakash S, Elliott P J. Proteasome inhibitors: a novel class of potent and effective antitumor agents. Cancer Res. 1999;59(11): 2615-22.
3. Akhter S A, Milano C A, Shotwell K F, Cho M C, Rockman H A, Lefkowitz R J, Koch W J. Transgenic mice with cardiac overexpression of $\alpha_{1\beta}$-receptors. J Biol Chem 1997; 272(34):21253-21259.
4. Anker S D, Coats A J S: How to RECOVER from RENAISSANCE? The significance of the results of RECOVER, RENAISSANCE, RENEWAL and ATTACH. Int J of Cardiol 2002;86:121-130.
5. Arnaud C, Joyeux-Faure M, Bottari S, Godin-ribuot D and Ribuot C, Heat stress triggers protein kinase C-epsilon translocation. Arch. Mal. Coeur Vaiss. 2003; 96: 411.
6. β-Blocker Heart attack Trial Research Group. A randomized trial of propranolol in patients with acute myocardial infarction. JAMA 1982; 247:1707-1713.
7. Becker L C, Fortuin N J, Pitt B. Effect of ischemia and antiangina drugs on the distribution of radioactive microspheres in the canine left ventricle. Circ Res 1971; 28:263-269.
8. Benovic J L, Strasser, R H, Caron M G, Lefkowitz R J. β-adrenergic receptor kinase: identification of a novel protein kinase that phosphorylates the agonist-occupied form of the receptor. Proc Natl Acad Sci USA 1986;83: 2797-2801.
9. Bigger J T, Fleiss J L, Kleiger R, et al. The relationships among ventricular arrhythmias, left ventricular dysfunction, and mortality in the 2 years after myocardial infarction. Circulation 1984; 69:250-258
10. Bristow M R, Hershberger R E, Port J D, Minobe W, Rasmussen R. $\beta_1$ and $\beta_2$-adrenergic receptor-mediated adenylate cyclase stimulation in nonfailing and failing human ventricular myocardium. Mol Pharmacol 1989;35: 295-303.
11. Bunemann M, Hosey M M. G-protein coupled receptor kinases as modulators of G-protein signaling. J Physiol 1999;517:5-23.
12. Cameron J S, Dersham G H, Han J. Effects of epinephrine on the electrophysiologic properties of Purkinje fibers surviving myocardial infarction. Am Heart J 1982;104: 551-560
13. Chandrasekar B, Freeman G L. Induction of nuclear factor κB and activation of protein 1 in postischemic myocardium. FEBS Left 1997;401:30-34.
14. Choi D J, Koch W J, Hunter J J, Rockman H A. Mechanism of β-adrenergic receptor desensitization in cardiac hypertrophy is increased β-adrenergic receptor kinase. J Biol Chem 1997;272(27):17223-17229.
15. Chuang T T, LeVine H III, DeBlasi A. Phosphorylation and activation of β-adrenergic receptor kinase by protein kinase C. J Biol Chem 1995;270(31):18660-18665.
16. Dangman K H, Dresdner K P Jr., Zaim S. Automatic and triggered impulse initiation in canine subepicardial ventricular muscle cells from border zones of 24-hour transmural infarct. Circulation 1988;78:1020-1030.
17. Dorn G W 2nd, Souroujon M C, Liron T. Chen C H, Gray M O, Zhou H Z, Csukai M, Wu G, Lorenz J N, Mochly-Rosen D. Sustained in vivo cardiac protection by a rationally designed peptide that causes epsilon protein kinase C translocation. Proc Natl Acad Sci U S A 1999; 96(22):12798-12803.
18. Drazner M H, Peppel K C, Dyer S, Grant A O, Koch W J, Lefkowitz R J. Potentiation of β-adrenergic signaling by adenoviral-mediated gene transfer in adult rabbit ventricular myocytes. J Clin Invest 1997;99:288-296.
19. De Ferrari G M, Salvati P. Grossoni M, Ukmar G, Vaga L, Patrano C, Schwartz P: Pharmacologic modulation of the autonomic nervous system in the prevention of sudden cardiac death. Astudy with propranolol, methacholine, and oxotremorine in conscious dogs with healed myocardial infarction. J Am Coll Cardiol 1993;21:283-290
20. D'Acquisto F, May M J, Ghosh S: Inhibition of nuclear factor Kappa B: An emerging theme in anti-inflammatory therapies. Mol Interven 2002;2:22-35

21. Elorza A, Penela. P, Sarnago S, Mayor F Jr. MAPK-dependent degradation of G protein-coupled receptor kinase 2. J Biol Chem. 2003;278(31):29164-73.
22. Entman M L, Smith C W. Postreperfusion inflammation: a model for reaction to injury in cardiovascular disease. *Cardiovasc Res* 1994;28: 1301-1311.
23. Euler D E, Nattel S, Spear, J F, Moore, E N, Scanlon, P J: Effect of sympathetic tone on ventricular arrhythmias during circumflex coronary occlusion. Am J Physiol 1985; 249:H1045-1050
24. El-Sherif N, Gough W B, Zeiler R H, Mehra R: Triggered ventricular rhythms in 1-day old myocardial infaction in the dog. Circ Res 1983; 566-579
25. Frangogiannis N G, Lindsey M L, Michael L H, Youker K A, Bressler R B, Mendoza L H, Spengler R N: Resident cardiac mast cells degranulate and release preformed TNF alpha, initiating the cytokine cascade in experimental canine myocardial ischemia/reperfusion. *Circulation* 1998; 98:699-710
26. Gainetdinov R R, Bohn L M, Walker J K, Laporte S A, Macrae A D, Caron M G, Lefkowitz R J, Premont R T. Muscarinic supersensitivity and impaired receptor desensitization in G protein-coupled receptor kinase 5-deficient mice. Neuron 1999;24(4):1029-1036.
27. Gillum R F. Sudden coronary death in the United States: 1980-1985. *Circulation* 1989; 79:756-765.
28. Gurevitch J, Frolkis I, Yuhas Y, et al. Tumor necrosis factor alpha is released from the isolated heart undergoing ischemia and reperfusion. *J. Am. Coil Cardiol* 1996; 28:247-252
29. Hammond H K, Roth D A, Insel P A, Ford C E, White F C, Maisel A S, Ziegler M G, Bloor C M. Myocardial β-adrenergic receptor expression and signal transduction after chronic volume-overload hypertrophy and circulatory congestion. Circulation 1992;85:269-280.
30. Harris A S, Estandia A, Tillotson R F: Ventricular ectopic thythms and ventricular fibrillation following cardiac sympathetctomy and coronary occlusion. Am J Physiol 1951; 165:505-512.
31. Hartzell H C: Regulation of cardiac ion channels by catecholamines, acetylcholine, and second messanger systems. Prog Biophys Mol Biol 1988;52:165-247
32. Haupt Y, Maya R, Kazaz A, Oren M. Mdm2 promotes the rapid degradation of p53. Nature 1997;387:296-299.
33. Herskowitz A, Choi S, Ansari M, Wesselingh S. Cytokine mRNA expression in postischemic/reperfusion myocardium. Am J pathol 1995;146:419-428.
34. Hjalmarsson A, Herlitz J, Malek I, et al.: Effect on mortality of metoprolol in acute myocardial infaction. A double blind randomized trial. *Lancet* 1981; 2:823-827
35. Hjalmarson A. Effects of beta blockade on sudden cardiac death during acute myocardial infarction and the postinfarction period. *Am J Cardiol* 1997;80:35J-39J
36. Iaccarino G, Tomhave E D, Lefkowitz R J, Koch W J. Reciprocal in vivo regulation of myocardial G protein-coupled receptor kinase expression by β-adrenergic receptor stimulation and blockade. Circulation 1998;98: 1783-1789.
37. Iesaka Y, Nogami A, Aonuma K, et al. Prognostic signicanance of sustained monomorphic tachycardia induced by programmed ventricular stimulation using up to triple extrastimuli in survivors of acute myocardial infarction. *Am J Cardiol* 1990; 65:1057-1063.
38. Irwin M W, Mak S, Mann D L, Qu R, Penninger J M, Yan A, Dawood F, Wen W-H, Shou Z, Liu P: Tissue expression and immunolocalization of tumor necrosis factor alpha in postinfarction dysfunctional myocardium. *Circulation* 1999; 99:1492-1498.
39. Isenberg G, Belardinelli L. Ionic basis for the antagonism between adenosine and isoproterenol on isolated mammalian myocytes. *Circ Res* 1984; 55:309-325.
40. Joyeux M, Baxter G F, Thomas D L, Ribuot C and Yellon D M, Protein kinase C is involved in resistance to myocardial infarction induced by heat stress. *J. Mol. Cell. Cardiol.* 1997; 29(12):3311-3319
41. Karin M, Ben-Neriah Y. Phosphorylation meets ubiquitination. The control of NF-κB activity. *Annu Rev Immunol* 2000; 18:621-663.
42. Kaumann A J, Aramendia P: Prevention of ventricular fibrillation induced by coronary ligation. *J Parmacol Exp Ther* 1968; 164:326-332.
43. Kempf F C, Josephson M E. Cardiac arrest recorded on ambulartory electrocardiograms. *Am J Cardiol* 1984; 53:1577-1582.
44. Kleiger R E, Miller p, Bigger J T, et al. Decreased heart rate variability and its association with increased mortality after acute myocardial infarction. Am I Cardiol 1987; 59:256-262.
45. Kleiman R B, Miller J M, Buxton A E, et al.: Prognosis following sustain ventricular tachycardia occurring after myocardial infarction. *Am J Cardiol* 1988; 62:528-533.
46. Koch W J, Rockman H A, Samama P, Hamilton R A, Bond R A, Milano C A, Lefkowitz R J. Cardiac function in mice overexpressing the beta-adrenergic receptor kinase or a beta ARK inhibitor. Science 1995;268(5215): 1350-1353.
47. Krupnick J G, Benovic J L. The role of receptor kinases and arrestins in G protein-coupled receptor regulation. Annu Rev Pharmacol Toxicol 1998;38:289-319.
48. Kukeilka G L, Smith C W, Maning A M, Yonker K A, Micheal K H, Entman M L. Induction of interleukin synthesis in the myocardium. Circulation 1995;92:1866-1875.
49. La Rovere M T, Specchia G, Mortara A, Schwartz P J. Baroreflex sensitivity, clinical correlates, and cardiovascular mortality among patients with a first myocardial infarction. Circulation 1988;78:816-824.
50. La Rovere M T, Pinna G D, Hohnloser S H, et al. Baroflex sensitivity and heart rate variability in the identification of patients at risk for life-threatening arrhythmias. Circulation 2001; 103:2072-2077.
51. Lee K B, Wang D, Lippard S J, Sharp P A. Transcription-coupled and DNA damage-dependent ubiquitination of RNA polymerase II in vitro. Proc Natl Acad Sci USA 2002;99:4239-4244.
52. Le Marec H, Deangman K H, Deanilo P, Rosen M R. An evaluation of automaticity and triggered activity in the canine heart one to four days after myocardial infarction. *Circulation* 1985; 71:1224-1236.
53. Li J G, Bonovic J L, Lin-Chen L Y. Mechanisms of agonist-induced down-regulation of the human kappa-opioid receptor: internalization is required for down-regulation. Mol Pharmacol. 2000; 58(4):795-801.
54. Liu G S, Cohen M V, Mochly-Rosen D, Downey J M. Protein kinase C-epsilon is responsible for the protection of preconditioning in rabbit cardiomyocytes. J Mol Cell Cardiol 1999;31(10):1937-1948.
55. Liu Z, Miers W R, Wei L, Barrett E J. The ubiquitin-proteasome proteolytic pathway in heart vs skeletal muscle: effects of acute diabetes. Biochem Biophys Res Commun. 2000;276(3):1255-60.

56. Luo J, Benovic J L. G protein-coupled receptor kinase interaction with Hsp90 mediates kinase maturation. J Biol Chem. 2003;278(51):50908-14.
57. Liberthson R R, Nagel E L, Hirschman J C et al. Pathophysiologic observations in prehospital ventricular fibrillation and sudden cardiac death. Circulation 1974; 49:790-797.
58. Lombardi M S, van den Tweel E, Kavelaars A, et al. Hypoxia/ischemia modulates G protein coupled receptor kinase 2 and beta-arrestin 1 levels in the neonatal rat brain. Stroke 2004; 35:981-986.
59. Malliani a, Schwartz P J, Zanchetti A. Neural mechanisms in life-threatening arrhythmias. Am Heart J 1980; 100:705-715.
60. Maroko P R, Kiekshus J K, Sobel B E, et al. Factors influencing infarct size following experimental coronary artery occlusions. Circulation 1971; 43:67-82.
61. Maxwell P H, at al. The tumor suppressor protein VHL targets hypoxia-inducible factors for oxygen-dependent proteolysis. Nature 1999;399:271-275.
62. Mich E, Zimdahl W T, Egan R W, Hsia T W, Anderson M, David J. Experimental prevention of sudden death from acute coronary artery occlusion in the dog. Am Heart J 1955; 30:483-599.
63. Miura M, Thomas R, Ganz W, et al. The effect of delay in propranolol administration on reduction of myocardial infarct size after experimental coronary artery occlusion in dogs. Circulation 1979; 59:1148-1157.
64. Moss A J, Davis H T, DeCamilla J, et al. Ventricular ectopic beats and their relation to sudden and nonsudden cardiac death after myocardial infarction. Circulation 1979; 60:998-1003.
65. Mullane K M, Kraemer R, Smith B. Myeloperoxidase activity as a quantitative assessment of neutrophil infiltration into ischemic myocardium. J Pharmacol Methods 1985; 14:157-167.
66. Olsson G, Rehnqvist N, Sjogren A, Erhardt L, Lundman T. Long-term treatment with metoprolol after myocardial infarction: effect on 3 year mortality and morbidity. J Am Coll Cardiol 1985; 5:1428-1437.
67. Opitz C F, Mitchell G F, Pfeffer M A, Pfeffer J M. Arrhythmias and death after coronary artery occlusion in the rat, continuous telemetric ECG monitoring in conscious, untethered rats. Circulation 1995;92(2):253-261.
68. Oppermann M, Diverse-Pierluissi M, Drazner M H, Dyer S A, Freedman N J, Peppel K C, Lefkowitz R J. Monoclonal antibodies reveal receptor specificity among G-protein-coupled receptor kinases. Proc Natl Acad Sci USA 1996;93:7649-7654.
69. Ostendorff H P, et al. Ubiquitination-dependent cofactor exchange on LIM homeodomain transcription factors. Nature 2002;416:99-103.
70. Palombella V J, Rando O J, Godberg A L, Maniatis T. the ubiquitin-proteasome pathway is required for processing the. NF-κB1 precursor protein and the activation of NF-κB. Cell 1994;78:773-785.
71. Panidis I P, Morganroth J. Sudden death in hospitalized patients: cardiac rhythm disturbances detected by ambulartory electrocardiographic monitoring. J Am Coll Cardiol 1983; 2:798-805.
72. Patterson E, Holland K, Eller B T, and Lucchesi B R: Ventricular fibrillation resulting from ischemia at a site remote from previous myocardial infarction: A conscious canine model of sudden coronary death. Am J Cardiol 1982;50:1414-1423.
73. Patterson E and Lucchesi B R: Antifibrillatory actions of d,l-nadolol in a conscious canine model of sudden coronary death. J Cardiovasc Pharmacol 1983;5:737-744.
74. Patterson E, Scherlag B J, Lazzara R. Mechanism of prevention of sudden death by nadolol: differential actions on arrhythmia triggers and substrate after myocardial infarction in the dog. J Am Coll Cardiol 1986;8:1365-1372
75. Patterson E, Scherlag B J, Lazzara R. Arrhythmias in the canine heart two to twenty-four hours after myocardial infarction. In Electrophysiology and Pharmacology of the Heart. Dangman K H and Miura D S, editors. Marcel Dekker, Inc., New York. 1991:301-330.
76. Patterson E, Scherlag B J, Lazzara R. Prevention of spontaneous sustained ventricular tachycardia in the postinfarction dog by left stellate ganglionectomy. J Cardiovasc Electrophysiol 1991;2:238-248.
77. Patterson E, Yu X, Kem D C: Beta-adrenergic receptor desensitization and loss of Iks current, 24 hrs following coronary artery ligation in the dog. PACE 2002;25:672A.
78. Penela P, Ruiz-Gomez A, Castano J G, Mayor F, Jr. Degradation of the G-protein-coupled receptor kinase 2 by the proteasome pathway. J Biol Chem 1998;273: 35238-35244.
79. Penela P, Elorza A, Sarnago S, Mayor F Jr. Beta-arrestin- and c-Src-dependent degradation of G-protein-coupled receptor kinase 2. EMBO J. 2001;20(18):5129-38.
80. Ping P, Geizer-Bell R, Roth D A, Kiel D, Insel P A, Hammond H K. Reduced β-adrenergic receptor activation decreases G-protein expression and β-adrenergic receptor kinase activity in porcine heart. J Clin Invest 1995;95: 1271-1280.
81. Ping P, Zhang J, Huang S, Cao X, Tang X L, Li RC, Zheng Y T, Qiu Y, Clerk A, Sugden P, Han J, Bolli R. PKC-dependent activation of p46/p54 JNKs during ischemic preconditioning in conscious rabbits. Am J Physiol 1999;277(5 Pt 2):H1771-85.
82. Ping P. Anzai T, Gao M, et al. Adenylyl cyclase and G protein receptor kinase expression during development of heart failure. Am J Physiol 1997;273(2 Pt 2):H707-17.
83. Pitcher J A, Freedman N J, Lefkowitz R J. G protein-coupled receptor kinases. Annu Rev Biochem 1998;67: 653-692.
84. Polakis P. Wnt signaling and cancer. Genes Dev 2000; 14:1837-1851.
85. Pye J, et al. Proteasome inhibition ablates activation of NF-κB in myocardial reperfusion and reduces reperfusion injury. Am J Physiol Heart Circ Physiol 2003;284:H919-H926.
86. Rape M, et al. Mobilization of processed, membrane-tethered SPT23 transcription factor by CDC48 (UFD1/NPL4), a ubiquitin-selective chaperone. Cell 2001;107: 667-677.
87. Rearon R E: Propranolol in the prevention of ventricular fibrillation due to experimental coronary artery occlusion. Am J Cardiol 1967;20:222-228.
88. Reimer K A, Rasmussen M M, Jennings R B. Reduction by propranolol of myocardial necrosis following temporary coronary occlusion in dogs. Circ Res 1973;33:353-363.
89. Rockman H A; Choi D J, Akhter S A, Jaber M, Giros B, Lefkowitz R J, Caron M G, Koch W J. Control of myocardial contractile function by the level of beta-adrenergic receptor kinase 1 in gene-targeted mice. J Biol Chem 1998;273(29):18180-18184.

90. Rockman H A, Koch W J, Lefkowitz R J. Cardiac function in genetically engineered mice with altered adrenergic receptor signaling. Am J Physiol 1997;272: H1553-H1559.
91. Ruberman W, Weinblatt E, Goldberg J D, et al. Ventricular premature beats and mortality after myocardial infarction. N Engl J Med 1977;297:750-757.
92. Salomon Y, Londos C, Rodbell M A: A highly sensitive adenylate cyclase assay. *Anal Biochem* 1974; 58:541-548.
93. Scherlag B J, Patterson E, Lazzara R: Seasonal variation in sudden cardiac death after experimental myocardial infarction. J Electrocardiol 1990;23:223-230.
94. Schwartz P J, Stone H L: Left stellectomy in the prevention of ventricular fibrillation caused by acute myocardial ischemia in conscious dogs with anterior myocardial infarction. Circulation 1980;62:1256-1265.
95. Schwartz P J, Vanoli E: Cardiac arrhythmias elicited by interaction between acute myocardial ischemia and sympathetic hyperactivity: A new experimental model for the study of antiarrhythmic drugs. J Cardiovasc Pharmacol 1981;3:1251-1259.
96. Steinberg S F, Zhang H, Pak E, Pagnotta G, Boyden P A. Characteristics of the β-adrenergic receptor complex in the epicardial border zone of the 5-day infarcted canine heart. Circulation 1995;91:2824-2833.
97. Svejstrup, J Q. Mechanisms of transcription-coupled DNA repair. Nature Rev Mol Cell Biol 2002;3:21 -29.
98. Theilade J, Strom C, Christiansen T, et al. Differential G protein receptor kinase 2 expression in compensated hypertrophy and heart failure after myocardial infarction in the rat. *Basic Res Cardiol* 2003;98:97-103.
99. The International Collaborative Study Group. Reduction of infarct size with the early use of timolol in acute myocardial infarction. N Engl J Med 1984;310:9-15.
100. Tiruppathi C, Yan W. Sandoval R, Naqvi T, Pronin A N, Benovic J, Malik A B. G protein-coupled receptor kinase-5 regulates thrombin-activated signaling in endothelial cells. Proc Natl Acad Sci USA 2000;97:7440-7445.
101. Torre-Amione G, kapadia S, Lee J, et al. Tumor necrosis factor-alpha and tumor necrosis factor receptors in the failing human heart. *Circulation* 1996;93:704-711.
102. Ungerer M, Kessebohm K, Kronsbein K, et al. Activation of β-adrenergic receptor kinase during myocardial ischemia. *Circ Res* 1996;79:455-460.
103. Vaddi K, Nicolini F A, Mehta P, Mehta J L. Increased secretion of tumor necrosis factor-alpha and interferon-gamma by mononuclear leukocytes in patients with ischemic heart disease: relevance in superoxide anion generation. Circulation 1994;90:694-699.
104. Vanoli E, De Ferrari G M, Stramba-Badiale M, Hull Jr S S, Foreman R D, Schwartz P J: Vagal stimulation and prevention of sudden death in conscious dogs with healed myocardial infarction. Circ Res 1991;68:1471-1481.
105. Yamada K A, Corr P B. Effects of β-adrenergic receptor activation on intracellular calcium and membrane potential in adult cardiac myocytes. J Cardiovasc Electrophysiol 1992;3:209-224.
106. Yamashita N, Hoshida S, Nishida M, Igarashi J, Aoki K, Hori M et al., Time course of tolerance to ischemia-reperfusion injury and induction of heat shock protein 72 by heat stress in the rat heart. *J. Mol. Cell. Cardiol.* 1997; 29(7): 1815-1821.
107. Youker K A, Hawkins H K, Michael L. Molecular evidence for induction of intracellular adhesion molecule-1 (ICAM-1) in the viable border zone associated with ischemia-reperfusion injury of the dog heart. *Circulation* 1994;89:2736-2746.
108. Yu X, Zhang M, Kyker K E, Patterson E, Benovic J L, Kem D C. Ischemic inactivation of G-protein coupled receptor kinase and altered desensitization of canine cardiac β-adrenergic receptors. Circulation 2000;102(20): 2535-2540.
109. Yu X, Patterson E, Kem D C. Etanercept protection from TNFα-induced reduction of β-adrenergic receptor kinase, rapid ventricular tachyarrhythmias and infarct size reduction in canine models of myocardial infarction. 85th Annual Meeting of the Endocrine Society June 19-22.2003, Philadelphia.
110. Yu X, Patterson E, Huang S, Kem D C. Etanercept Protection from TNFα-induced Reduction of β-Adrenergic Receptor Kinase, Rapid Ventricular Tachyarrhythmias and Infarct Size Reduction in Canine Models of Myocardial Infarction. 2004, submitted to J Pharmacol Exp Ther.
111. Yu X, Patterson E, Kem D C. Reduced β-adrenergic receptor kinase in ischemic subepicardial border zone in the 24-hr infarcted dog. AHA Scientific Conference on Molecular, Integrative, and Clinical Approaches to Myocardial Ischemia, August 2001, Seattle, Wash.
112. Zehender M, Utzolino S, Furtwangler A, Kasper W, Meinertz T, Just H. Time course and interrelation of reperfusion-induced ST changes and ventricular arrhythmias in acute myocardial infarction. Am J Cardiol 1991; 68:1138-1142.

What is claimed is:

1. A method of treating sustained monomorphic ventricular tachycardia in a patient following myocardial ischemia, wherein the patient is experiencing acute myocardial infarction, the method comprising the step of:

administering to the patient an effective amount of a composition comprising bortezomib, wherein the composition inhibits substantial loss of at least one of beta-adrenergic receptor kinase activity and beta-adrenergic receptor kinase expression, and wherein the administration of the composition reduces the occurrence of sustained monomorphic ventricular tachycardia.

2. The method of claim 1, wherein the administration of the composition results in the inhibition of the degradation of beta-adrenergic receptor kinase in response to myocardial ischemia.

3. The method of claim 1, wherein the administration of the composition results in a retention of at least about 10% of beta-adrenergic receptor kinase activity under non-ischemic conditions.

4. The method of claim 1, wherein the administration of the composition results in a retention of at least about 20% of beta-adrenergic receptor kinase activity under non-ischemic conditions.

5. The method of claim 1, wherein the administration of the composition results in a retention of at least about 30% of beta-adrenergic receptor kinase activity under non-ischemic conditions.

6. The method of claim 1, wherein the administration of the composition results in a retention of at least about 40% of beta-adrenergic receptor kinase activity under non-ischemic conditions.

7. The method of claim 1, wherein the administration of the composition results in a retention of at least about 50% of beta-adrenergic receptor kinase activity under non-ischemic conditions.

* * * * *

UNITED STATES PATENT AND TRADEMARK OFFICE
CERTIFICATE OF CORRECTION

PATENT NO. : 7,348,305 B2  Page 1 of 1
APPLICATION NO. : 10/927616
DATED : March 25, 2008
INVENTOR(S) : David C. Kem and Eugene S. Patterson It is certified that error appears in the above-identified patent and that said Letters Patent is hereby corrected as shown below:

In the Specification:
 Column 7, line 42: Delete "menentioned" and replace with -- mentioned --.
 Column 32, line 36: Delete "Left" and replace with -- Lett --.
 Column 33, line 46: After "Ansari" delete "M," and replace with -- AA, --.
 Column 35, line 22: Delete "M," and replace with -- AA, --.
 Column 37, line 39: Delete "kapadia" and replace with -- Kapadia --.

Signed and Sealed this

Fifteenth Day of July, 2008

JON W. DUDAS
*Director of the United States Patent and Trademark Office*

SEQUENCE LISTING

```
<160> NUMBER OF SEQ ID NOS: 8

<210> SEQ ID NO 1
<211> LENGTH: 20
<212> TYPE: DNA
<213> ORGANISM: artificial sequence
<220> FEATURE:
<223> OTHER INFORMATION: primer - 18S (internal control) forward

<400> SEQUENCE: 1
ttcggaactg aggccatgat                                            20
```

<210> SEQ ID NO 2
<211> LENGTH: 20
<212> TYPE: DNA
<213> ORGANISM: Artificial Sequence
<220> FEATURE:
<223> OTHER INFORMATION: primer - 18S (internal control) reverse primer

<400> SEQUENCE: 2
tttcgctctg gtccgtcttg					20

<210> SEQ ID NO 3
<211> LENGTH: 20
<212> TYPE: DNA
<213> ORGANISM: Artificial Sequence
<220> FEATURE:
<223> OTHER INFORMATION: primer - GAPDH (internal control) forward
      primer

<400> SEQUENCE: 3
cagtgacacc cactcttcca					20

<210> SEQ ID NO 4
<211> LENGTH: 20
<212> TYPE: DNA
<213> ORGANISM: Artificial Sequence
<220> FEATURE:
<223> OTHER INFORMATION: primer - GAPDH (internal control) reverse
      primer

<400> SEQUENCE: 4
ccggttgctg tagccaaatt					20

<210> SEQ ID NO 5
<211> LENGTH: 23
<212> TYPE: DNA
<213> ORGANISM: Artificial Sequence
<220> FEATURE:
<223> OTHER INFORMATION: primer - beta-ARK forward primer

<400> SEQUENCE: 5
accaggaact ctaccgcaac ttt				23

<210> SEQ ID NO 6
<211> LENGTH: 20
<212> TYPE: DNA
<213> ORGANISM: Artificial Sequence
<220> FEATURE:
<223> OTHER INFORMATION: primer - beta-ARK reverse primer

<400> SEQUENCE: 6
ttttcttgcg ggcctccatt					20

<210> SEQ ID NO 7
<211> LENGTH: 23
<212> TYPE: DNA
<213> ORGANISM: Artificial Sequence
<220> FEATURE:
<223> OTHER INFORMATION: primer - GRK5 (homolog control) forward primer

<400> SEQUENCE: 7
ggatgttgga ccctcccttc att				23

```
<210> SEQ ID NO 8
<211> LENGTH: 20
<212> TYPE: DNA
<213> ORGANISM: Artificial Sequence
<220> FEATURE:
<223> OTHER INFORMATION: primer - GRK5 (homolog control) reverse primer

<400> SEQUENCE: 8
acgcctttca cggtggagaa                                              20
```